US008604185B2

(12) United States Patent
Gerber et al.

(10) Patent No.: US 8,604,185 B2
(45) Date of Patent: Dec. 10, 2013

(54) INHIBITORS OF ANGIOPOIETIN-LIKE 4 PROTEIN, COMBINATIONS, AND THEIR USE

(75) Inventors: Hanspeter Gerber, San Francisco, CA (US); Napoleone Ferrara, San Francisco, CA (US); Xiao Huan Liang, Redwood City, CA (US)

(73) Assignee: Genentech, Inc., South San Francisco, CA (US)

( * ) Notice: Subject to any disclaimer, the term of this patent is extended or adjusted under 35 U.S.C. 154(b) by 517 days.

(21) Appl. No.: 12/820,122

(22) Filed: Jun. 21, 2010

(65) Prior Publication Data

US 2011/0311524 A1    Dec. 22, 2011

Related U.S. Application Data

(62) Division of application No. 11/185,215, filed on Jul. 19, 2005, now Pat. No. 7,740,846.

(60) Provisional application No. 60/589,782, filed on Jul. 20, 2004.

(51) Int. Cl.
    *C07H 21/04*    (2006.01)

(52) U.S. Cl.
    USPC ............................................. 536/24.5; 435/5

(58) Field of Classification Search
    None
    See application file for complete search history.

(56) References Cited

U.S. PATENT DOCUMENTS

| 4,816,567 | A | 3/1989 | Cabilly et al. |
|---|---|---|---|
| 5,521,073 | A | 5/1996 | Davis et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,571,894 | A | 11/1996 | Wels et al. |
| 5,587,458 | A | 12/1996 | King et al. |
| 5,625,126 | A | 4/1997 | Lonberg et al. |
| 5,633,425 | A | 5/1997 | Lonberg et al. |
| 5,641,756 | A | 6/1997 | Robinson |
| 5,641,870 | A | 6/1997 | Rinderknecht et al. |
| 5,650,490 | A | 7/1997 | Davis et al. |
| 5,661,016 | A | 8/1997 | Lonberg et al. |
| 5,750,373 | A | 5/1998 | Garrard et al. |
| 5,814,464 | A | 9/1998 | Davis et al. |
| 6,348,350 | B1 * | 2/2002 | Goddard et al. .............. 435/325 |
| 6,372,491 | B1 | 4/2002 | Goddard et al. |
| 6,455,496 | B1 | 9/2002 | Goddard et al. |
| 6,475,753 | B1 | 11/2002 | Ruben et al. |
| 6,582,959 | B2 | 6/2003 | Kim |
| 6,627,741 | B2 | 9/2003 | Brewer et al. |
| 6,673,545 | B2 | 1/2004 | Faris et al. |
| 6,703,020 | B1 | 3/2004 | Thorpe et al. |
| 6,884,879 | B1 | 4/2005 | Baca et al. |
| 7,371,384 | B2 | 5/2008 | Gerber |
| 2002/0119463 | A1 | 8/2002 | Faris et al. |
| 2003/0055006 | A1 | 3/2003 | Siemeister et al. |
| 2003/0065151 | A1 | 4/2003 | Ruben et al. |
| 2003/0143732 | A1 * | 7/2003 | Fosnaugh et al. .............. 435/325 |
| 2003/0170891 | A1 * | 9/2003 | McSwiggen .................. 435/366 |
| 2003/0190317 | A1 | 10/2003 | Baca et al. |
| 2003/0199058 | A1 | 10/2003 | Baker et al. |
| 2003/0203409 | A1 | 10/2003 | Kim |
| 2003/0206899 | A1 | 11/2003 | Ferrara et al. |
| 2003/0207348 | A1 | 11/2003 | Shimkets et al. |
| 2003/0207350 | A1 | 11/2003 | Baker et al. |
| 2003/0207351 | A1 | 11/2003 | Baker et al. |
| 2003/0207352 | A1 | 11/2003 | Baker et al. |
| 2003/0207353 | A1 | 11/2003 | Baker et al. |
| 2003/0207356 | A1 | 11/2003 | Baker et al. |
| 2003/0207357 | A1 | 11/2003 | Baker et al. |
| 2003/0207359 | A1 | 11/2003 | Baker et al. |
| 2003/0207360 | A1 | 11/2003 | Baker et al. |
| 2003/0207371 | A1 | 11/2003 | Baker et al. |
| 2003/0207374 | A1 | 11/2003 | Baker et al. |
| 2003/0207375 | A1 | 11/2003 | Baker et al. |
| 2003/0207376 | A1 | 11/2003 | Baker et al. |
| 2003/0207389 | A1 | 11/2003 | Baker et al. |
| 2003/0207422 | A1 | 11/2003 | Baker et al. |
| 2003/0207423 | A1 | 11/2003 | Baker et al. |
| 2003/0207424 | A1 | 11/2003 | Baker et al. |
| 2003/0207425 | A1 | 11/2003 | Baker et al. |

(Continued)

FOREIGN PATENT DOCUMENTS

| CN | 1315451 | 10/2001 |
|---|---|---|
| CN | 1343725 | 4/2002 |
| CN | 1343725 A | 4/2002 |
| EP | 0 666 868 B1 | 4/2002 |
| JP | 2000-308488 | 11/2000 |
| WO | WO 93/11161 | 6/1993 |
| WO | WO 93/16185 | 8/1993 |
| WO | WO 94/10202 | 5/1994 |
| WO | WO 96/30046 | 10/1996 |
| WO | WO 98/45331 | 4/1998 |

(Continued)

OTHER PUBLICATIONS

Yoshida, et al. (2002, J. Lipid Res., v.43:1770-1772).*
Notice of Opposition filed in European Patent Application 05790352.8 (now granted patent EP1771474B1) dated Nov. 10, 2010.
Kerbel, Tumor angiogenesis: past, present and the near future. Carcinogenesis 21: 505515 (2000).
Kim et al., Distinct Response of Experimental Neuroblastoma to Combination Antiangiogenic Strategies. Journal of Pediatric Surgery 37: 518-522 (2002).

(Continued)

*Primary Examiner* — Laura B Goddard
*Assistant Examiner* — Meera Natarajan
(74) *Attorney, Agent, or Firm* — Carol Fang; Jeffery P. Bernhardt; Arnold & Porter LLP

(57) ABSTRACT

Modulators of angiopoietin-like 4 protein are provided along with methods for their use in the treatment of diseases and pathological conditions. Combinations of ANGPTL4 antagonists and other therapeutics, e.g., anti-cancer agents, and methods of their use in the treatment of mammals susceptible to or diagnosed with cancer, or with relapse tumor growth or relapse cancer cell growth are also provided.

4 Claims, 16 Drawing Sheets

(56) References Cited

U.S. PATENT DOCUMENTS

| | | |
|---|---|---|
| 2003/0207426 A1 | 11/2003 | Baker et al. |
| 2003/0207427 A1 | 11/2003 | Baker et al. |
| 2003/0208055 A1 | 11/2003 | Baker et al. |
| 2003/0215451 A1 | 11/2003 | Ferrara et al. |
| 2003/0219885 A1 | 11/2003 | Baker et al. |
| 2004/0133357 A1 | 7/2004 | Zhong et al. |
| 2004/0249141 A1 | 12/2004 | Goddard et al. |
| 2005/0112126 A1 | 5/2005 | Baca et al. |
| 2005/0123925 A1 | 6/2005 | Ashkenazi et al. |
| 2005/0233361 A1 | 10/2005 | Clerc et al. |
| 2005/0239706 A1 | 10/2005 | Backhed et al. |
| 2006/0222645 A1 | 10/2006 | Lee et al. |

FOREIGN PATENT DOCUMENTS

| | | |
|---|---|---|
| WO | WO 99/15654 | 9/1998 |
| WO | 98/45331 | 10/1998 |
| WO | WO 98/45332 | 10/1998 |
| WO | WO 99/32515 | 7/1999 |
| WO | WO 99/45135 | 9/1999 |
| WO | WO 99/66041 | 12/1999 |
| WO | WO 99/67382 | 12/1999 |
| WO | WO 00/72801 A2 | 5/2000 |
| WO | WO 00/52165 | 9/2000 |
| WO | WO 00/61629 | 10/2000 |
| WO | WO 01/53486 A1 | 11/2000 |
| WO | WO 01/02429 A2 | 1/2001 |
| WO | WO 01/05825 A2 | 1/2001 |
| WO | WO 01/05971 A2 | 1/2001 |
| WO | WO 01/53455 A2 | 7/2001 |
| WO | WO 01/54477 A2 | 8/2001 |
| WO | WO 01/57188 A2 | 8/2001 |
| WO | WO 01/77151 A2 | 10/2001 |
| WO | WO 02/077013 A2 | 10/2002 |
| WO | WO 02/101039 A1 | 12/2002 |
| WO | WO 03/000865 A2 | 1/2003 |
| WO | WO 03/010205 A1 | 2/2003 |
| WO | WO 03/025138 A2 | 3/2003 |
| WO | WO 03/040329 A2 | 5/2003 |
| WO | WO 03/040330 A2 | 5/2003 |
| WO | WO 03/048185 A2 | 6/2003 |
| WO | WO 03/060071 A2 | 7/2003 |
| WO | WO 2005/012359 A2 | 2/2005 |
| WO | WO 2005/044853 A2 | 5/2005 |
| WO | WO 2006/014678 A2 | 2/2006 |
| WO | WO 2006/014729 A2 | 2/2006 |

OTHER PUBLICATIONS

Fan et al., In vitro evaluation of combination chemotherapy against human tumor cells (Review). Oncol. Rep. 5: 1035-1042 (1998).
Hurwitz et al., Bevacizumab plus Irinotecan, Fluorouracil, and Leucovorin for Metastatic Colorectal Cancer. The New England Journal of Medicine 350: 2335-2342 (2004).
Verheul et al., Combination oral antiangiogenic therapy with thalidomide and sulindac inhibits tumour growth in rabbits. British Journal of Cancer 79: 114-118 (1999).
Schiffelers et al., Cancer siRNA therapy by tumor selective delivery with ligandtargeted sterically stabilized nanoparticle. Nucleic Acids Research 32 (2004) (Published Online).
Kennett, Antibodies to target integrins expressed on tumor vasculature. Current Opinion in Oncologic, Endocrine & Metabolic Investigational Drugs 2: 376-380 (2000).
Partial English translation of CN 1343725 A cited in Office Action of Chinese Patent Application No. 200580031689.3.
Eliceiri, et al., "The role of αv integrins during angiogenesis: insights into potential mechanisms of action and clinical development", The journal of Clinical Investigation, vol. 103, No. 9, pp. 1227-1230, (1999).
Nejjari, et al., "Expression, Regulation, and function of αV integrins in hepatocellular carcinoma: an in vivo and in vitro study", Hapatology, vol. 36, No. 2, pp. 418-426, (2002).
Yang, et al., "Suppression of the Raf/MEK/ERK signaling cascade and inhibition of angiogenesis by the carboxyl terminus of angiopoietin-like protein 4", Arteriosclerosis, Thrombosis and vascular biology, 28: 835, (2008).
Office Action mailed Jan. 8, 2008—U.S. Appl. No. 11/540,884.
Office Action mailed Jul. 14, 2008 U.S. Appl. No. 11/540,884.
Office Action mailed May 22, 2009 U.S. Appl. No. 11/540,884.
Office Action mailed Dec. 15, 2008—U.S. Appl. No. 11/540,430.
Office Action mailed Jun. 5, 2009—U.S. Appl. No. 11/540,430.
Mesiano et al., "Role of Vascular Endothelial Growth Factor in Ovarian Cancer: Inhibition of Ascites Formation by Immunoneutralization" American Journal of Pathology vol. 153, No. 4 pp. 1249-1256 (1998), XP002373802, ISSN: 0002-9440.
Wei-Ching et al., "Cross Species Vascular Endothelial Growth Factor (VEGF)-Blocking Antibodies Completely Inhibit the Growth of Human Tumor Xenografts and Measure the Contribution of Stromal VEGF" Journal of Biological Chemistry vol. 281, No. 2, pp. 951-960 (2006) XP002373804 ISSN: 0021-9258.
Adamis et al., "Inhibition of Vascular Endothelial Growth Factor Prevents Retinal Ischemia-Associated Iris Neovascularization in a Nonhuman Primate" Arch. Ophthalmology 114(1):66-71 (1996).
Akiyama et al., "Conditional disruption of the peroxisome proliferator-activated receptor gamma gene in mice results in lowered expression of ABCA1, ABCG1, and apoE in macrophages and reduced cholesterol efflux" Molecular & Cellular Biology 22(8):2607-2619 (Apr. 2002).
Anderson, W.F., "Human Gene Therapy" Science 256(5058):808-813 (May 8, 1992).
Asano et al., "Inhibition of tumor growth and metastasis by an immunoneutralizing monoclonal antibody to human vascular endothelial growth factor/vascular permeability factor121" Cancer Research 55(22):5296-5301 (Nov. 15, 1995).
Borgstrom et al., "Complete inhibition of angiogenesis and growth of microtumors by anti-vascular endothelial growth factor neutralizing antibody: novel concepts of angiostatic therapy from intravital videomicroscopy" Cancer Research 56(17):4032-4039 (Sep. 1, 1996).
Byzova et al., "A mechanism for modulation of cellular responses to VEGF: activation of the integrins" Mol Cell 6(4):851-860 (Oct. 2000).
Camenisch et al., "ANGPTL3 stimulates endothelial cell adhesion and migration via integrin alpha vbeta 3 and induces blood vessel formation in vivo" J Biol Chem. 277(19):17281-17290 (May 10, 2002).
Carmeliet and Jain, "Angiogenesis in cancer and other diseases" Nature 407(6801):249-257 (Sep. 14, 2000).
Carmeliet, "Mechanisms of angiogenesis and arteriogenesis" Nature Medicine 6(3):389-395 (Mar. 2000).
Davis et al., "Isolation of angiopoietin-1, a ligand for the TIE2 receptor, by secretion-trap expression cloning" Cell 87(7):1161-1169 (Dec. 27, 1996).
Eliceiri and Cheresh, "Adhesion events in angiogenesis" Curr Opin Cell Biol. 13(5):563-568 (Oct. 2001).
Eliceiri and Cheresh, "The role of alphav integrins during angiogenesis" Mol Med. 4(12):741-750 (Dec. 1998).
Ferrara and Alitalo, "Clinical applications of angiogenic growth factors and their inhibitors" Nat Med. 5(12):1359-1364 (Dec. 1999)
Ferrara and Davis-Smyth, "The Biology of Vascular Endothelial Growth Factor" Endocrine Reviews 18(1):4-25 (1997).
Ferrara and Kerbel, "Angiogenesis as a therapeutic target" Nature 438(7070):967-974 (Dec. 15, 2005).
Ferrara et al., "Discovery and Development of Bevacizumab, an Anti-VEGF Antibody for Treating Cancer" Nature Reviews—Drug Discovery 3:391-400 (May 2004).
Ferrara et al., "The biology of VEGF and its receptors" Nat Med. 9(6):669-676 (Jun. 2003).
Ferrara, N., "Molecular and biological properties of vascular endothelial growth factor" J Mol Med 77527-543 (1999).
Folkman and D'Amore, "Blood vessel formation: what is its molecular basis?" Cell 87(7):1153-1155 (Dec. 27, 1996).

(56) References Cited

OTHER PUBLICATIONS

Fong et al., "SU5416 is a potent and selective inhibitor of the vascular endothelial growth factor receptor (Flk-1/KDR) that inhibits tyrosine kinase catalysis, tumor vascularization, and growth of multiple tumor types" *Cancer Research* 59(1):99-106 (Jan. 1, 1999).
Friedlander et al., "Definition of two angiogenic pathways by distinct alpha v integrins" *Science* 270(5241):1500-1502 (Dec. 1, 1995).
Friedmann, "Gene therapy—a new kind of medicine" *TIBTECH* 11(5):156-159 (May 1993).
Fukumura et al., "Paracrine regulation of angiogenesis and adipocyte differentiation during in vivo adipogenesis" *Circ Res.* (e88-e97) 93(9):1-10 (Oct. 31, 2003).
Ge et al., "Differential regulation and properties of angiopoietin-like proteins 3 and 4" *J Lipid Res.* 46(7):1484-1490 (Jul. 2005).
Ge et al., "Oligomerization and regulated proteolytic processing of angiopoietin-like protein 4" *J Biol Chem.* 279(3):2038-2045 (Jan. 16, 2004).
Ge et al., "Oligomerization state-dependent hyperlipidemic effect of angiopoietin-like protein 4" *J Lipid Res.* 45(11):2071-2079 (Nov. 2004).
Ge Hongfei, et al., "Oligomerization and regulated proteolytic processing of angiopoietin like protein 4" *Diabetes* (2430-PO) 53(Suppl. 2):A576 (Jun. 2004).
Gerber et al., "Complete inhibition of rhabdomyosarcoma xenograft growth and neovascularization requires blockade of both tumor and host vascular endothelial growth factor" *Cancer Research* 60(22):6253-6258 (Nov. 15, 2000).
Goldman et al., "Paracrine expression of a native soluble vascular endothelial growth factor receptor inhibits tumor growth, metastasis, and mortality rate" *Proc Natl Acad Sci U S A.* 95(15):8795-8800 (Jul. 21, 1988).
Goldspiel et al., "Human gene therapy" *Clin Pharm.* 12(7):488-505 (Jul. 1993).
Gong, Dawei et al., "New progress in adipocytokine research" *Current Opinion in Endocrinology and Diabetes* 10(2):115-121 (2003).
Hermann et al., "Angiopoietin-like-4 is a potential angiogenic mediator in arthritis" *Clin Immunol.* 115(1):93-101 (Apr. 2005).
Hesser et al., "Down syndrome critical region protein 1 (DSCR1), a novel VEGF target gene that regulates expression of inflammatory markers on activated endothelial cells" *Blood* 104(1):149-158 (Jul. 1, 2004).
Holash et al., "New model of tumor angiogenesis: dynamic balance betwwen vessel regression and growth mediates by angiopoietins and VEGF" *Oncogene* 18(38):5356-5362 (Sep. 20, 1999).
Hood and Cheresh, "Role of integrins in cell invasion and migration" *Nat Rev Cancer* 2(2):91-100 (Feb. 2002).
Houck et al., "The Vascular Endothelial Growth Factor Family: Identification of a Fourth Molecular Species and Characterization of Alternative Splicing of RNA" *Mol. Endocrinol.* 5(12):1806-1814 (1991).
Hynes and Bader, "Targeted mutations in integrins and their ligands: their implications for vascular biology" *Thromb Haemost.* 78(1):83-87 (Jul. 1997).
Hynes et al., "Integrins in vascular development" *Braz J Med Biol Res.* 32(5):501-510 (May 1999).
Inukai et al., "ANGPTL3 is increased in both insulin-deficient and -resistant diabetic states" *Biochemical and Biophysical Research Communications* 317:1075-1079 (2004).
Ito et al., "Inhibition of angiogenesis and vascular leakiness by angiopoietin-related protein 4" *Cancer Research* 63(20):6651-6657 (Oct. 15, 2003).
Kersten et al., "Characterization of the fasting-induced adipose factor FIAF, a novel peroxisome proliferator-activated receptor target gene" *J Biol Chem.* 275(37):28488-28493 (Sep. 15, 2000).
Kim et al., "Hepatic expression, synthesis and secretion of a novel fibrinogen/angiopoietin-related protein that prevents endothelial-cell apoptosis" *Biochemical Journal* 346(Pt 3):603-610 (Mar. 15, 2000).
Kim et al., "Inhibition of Vascular Endothelial Growth Factor-Induced Angiogenesis Suppresses Tumour Growth in vivo" *Nature* 362:841-844 (Apr. 29, 1993).

Kimura, Metsutoshi et al., "Stimulation of DNA synthesis and proliferation by prostaglandins in primary cultures of adult rat hepatocytes" *European Journal of Pharmacology* 404(3):259-271 (Sep. 2000).
Klagsbrun and D'Amore, "Regulators of angiogenesis" *Ann. Rev. Physiol.* 53:217-239 (1991).
Koishi et al., "Angptl3 regulates Lipid metabolism in mice" *Nat Genet.* 30(2):151-157 (Feb. 2002).
Koster et al., "Transgenic angiopoietin-like (angptl)4 overexpression and targeted disruption of angpt14 and angpt13: regulation of triglyceride metabolism" *Endocrinology* 146(11):4943-4950 (Nov. 2005).
Landegren, "Measurement of cell numbers by means of the endogenous enzyme hexosaminidase. Applications to detection of lymphokines and cell surface antigens" *J Immunol Methods* 67(2): 379-388 (Mar. 16, 1984).
Le Jan et al., "Angiopoietin-like 4 is a proangiogenic factor produced during ischemia and in conventional renal cell carcinoma" *Am J Pathol.* 162(5):1521-1528 (May 2003).
Leung et al., "Vascular Endothelial Growth Factor is a Secreted Angiogenic Mitogen" *Science* 246:1306-1309 (Dec. 1989).
Lin et al., "Antiangiogenic gene therapy targeting the endothelium-specific receptor tyrosine kinase Tie2" *Proc Natl Acad Sci U S A.* 95(15):8829-8834 (Jul. 21, 1998).
Maisonpierre et al., "Angiopoietin-2, a Natural Antagonist for Tie2 that Disrupts in vivo Angiogenesis" *Science* 277:55-60 (Jul. 4, 1997).
Mandard et al., "The direct peroxisome proliferator-activated receptor target fasting-induced adipose factor (FIAF/PGAR/ANGPTL4) is present in blood plasma as a truncated protein that is increased by fenofibrate treatment" *J Biol Chem.* 279(33):34411-34420 (Aug. 13, 2004).
Mandard et al., "The fasting-induced adipose factor/angiopoietin-like protein 4 is physically associated with lipoproteins and governs plasma lipid levels and adiposity" *J Biol Chem.* 281(2):934-944 (Jan. 13, 2006).
Marshall et al., "The role of alpha v-integrins in tumour progression and metastasis" *Semin Cancer Biol.* 7(3):129-138 (Jun. 1996).
Melnyk et al., "Vascular endothelial growth factor promotes tumor dissemination by a mechanism distinct from its effect on primary tumor growth" *Cancer Research* 56(4):921-924 (Feb. 15, 1996).
Millauer, "Dominant-negative inhibition of Flk-1 suppresses the growth of many tumor types in vivo" *Cancer Research* 56(7):1615-1620 (Apr. 1, 1996).
Millauer, "Glioblastoma growth inhibited in vivo by a dominant-negative Flk-1 mutant" *Nature* 367(6463):576-579 (Feb. 10, 1994).
Minn et al., "Genes that mediate breast cancer metastasis to lung" *Nature* 436(7050):518-524 (Jul. 28, 2005).
Mitani et al., "Delivering therapeutic genes—matching approach and application" *TIBTECH* 11(5):162-166 (May 1993).
Morgan and Anderson, "Human gene therapy" *Annu Rev Biochem* 62:191-217 (1993).
Mujumdar et al., "Mechanism of constrictive vascular remodeling by homocysteine: role of PPAR" *Am. J Physiol. Cell Physiol.* 282:C1009-C1015 (May 2002).
Mulligan, "The basic science of gene therapy" *Science* 260(5110):926-932 (May 14, 1993).
Popkov et al., "Human/mouse cross-reactive anti-VEGF receptor 2 recombinant antibodies selected from an immune b9 allotype rabbit antibody library" *J Immunol Methods* 288(1-2):149-164 (May 2004).
Presta et al., "Humanization of an Anti-Vascular Endothelial Growth Factor Monoclonal Antibody for the Therapy of Solid Tumors and Other Disorders" *Cancer Research* 57(2):4593-4599 (Oct. 15, 1997).
Presta et al., "Humanization of an Antibody Directed Against IgE" *J. Immunol.* 151(5):2623-2632 (Sep. 1, 1993).
Procopio et al., "Angiopoietin-1 and -2 coiled coil domains mediate distinct homo-oligomerization patterns, but fibrinogen-like domains mediate ligand activity" *J Biol Chem.* 274(42):30196-30201 (Oct. 15, 1999).
Ramsay, T.G. et al., "Hormonal regulation of postnatal chicken preadipocyte differentiation in vitro" *Comparative Biochemistry and Physiology* Part B(136):245-253 (2003).

(56) References Cited

OTHER PUBLICATIONS

Robinson and Stringer, "The splice variants of vascular endothelial growth factor (VEGF) and their receptors" *J Cell Sci.* 114(5):853-865 (Mar. 2001).
Robinson, "Gene therapy—proceeding from laboratory to clinic" *TIBTECH* 11(5):155 (May 1993).
Rupnick et al., "Adipose tissue mass can be regulated through the vasculature" *Proc Natl Acad Sci USA* 99(16):10730-10735 (Aug. 6, 2002).
Sato, "Molecular diagnosis of tumor angiogenesis and anti-angiogenic cancer therapy" *Int J Clin Oncol.* 8(4):200-206 (Aug. 2003).
Schier et al., "Identification of functional and structural amino-acid residues by parsimonious mutagenesis" *Gene* 169(2):147-155 (Mar. 9, 1996).
Schmuth et al., "Peroxisome proliferator-activated receptor (PPAR)-beta/delta stimulates differentiation and lipid accumulation in keratinocytes" *Journal of Investigative Dermatology* 122:971-983 (2004).
Shimizugawa et al., "ANGPTL3 Decreases Very Low Density Lipoprotein of Lipoprotein Triglyceride Clearance by Inhibition of Lipoprotein Lipase" *The Journal of Biological Chemistry* 277(37):33742-33748 (Sep. 13, 2002).
Shweiki et al., "Induction of vascular endothelial growth factor expression by hypoxia and by glucose deficiency in multicell spheroids: implications for tumor angiogenesis" *Proc Natl Acad Sci USA.* 92(3):768-772 (Jan. 31, 1995).
Siemeister at al., "The pivotal role of VEGF in tumor angiogenesis: molecular facts and therapeutic opportunities" *Cancer Metastasis Rev.* 17(2):241-248 (Jun. 1998).
Siemeister et al., "Two independent mechanisms essential for tumor angiogenesis: inhibition of human melanoma xenograft growth by interfering with either the vascular endothelial growth factor receptor pathway or the Tie-2 pathway" *Cancer Research* 59(13):3185-3191 (Jul. 1, 1999).
Sierra-Honigmann et al., "Biological action of leptin as an angiogenic factor" *Science* 281(5383):1683-1686 (Sep. 11, 1998).
Sims et al., "A Humanized CD18 Antibody Can Block Function Without Cell Destruction" *The Journal of Immunology* 151(4):2296-2308 (Aug. 15, 1993).
Smith et al., "Interaction of integrins alpha v beta 3 and glycoprotein IIb-IIIa with fibrinogen. Differential peptide recognition accounts for distinct binding sites" *J Biol Chem.* 265(21):12267-12271 (Jul. 25, 1990).
Strausberg et al. (MGC Program Team), "Generation and initial analysis of more than 15,000 full-lengh human and mouse cDNA sequences" *Proc. Natl. Acad. Sci. USA* 99(26):16899-16903 (Dec. 24, 2002).
Streit and Detmar, "Angiogenesis, lymphangiogenesis, and melanoma metastasis" *Oncogene* 22(20):3172-3179 (May 19, 2003).
Stupack et al., "Get a ligand, get a life: integrins, signaling and cell survival" *J Cell Sci.* 115(Pt 19):3729-2738 (Oct. 1, 2002).
Suri et al., "Requisite role of angiopoietin-1, a ligand for the TIE2 receptor, during embryonic angiogenesis" *Cell* 87(7):1171-1180 (Dec. 27, 1996).
Tolstoshev, "Gene Therapy, concepts, current trials and future directions" *Annual review of pharmacology and toxicology* 32:573-596 (1993).
Tomayko & Reynolds, "Determination of subcutaneous tumor size in athymic (nude) mice" *Cancer Chemother Pharmacol.* 24(3):148-154 (1989).
Tonini et al., "Molecular basis of angiogenesis and cancer" *Oncogene* 22(42):6549-6556 (Sep. 29, 2003).
Valenzuela et al., "Angiopoietins 3 and 4: diverging gene counterparts in mice and humans" *Proc Natl Acad Sci USA.* 96(5):1904-1909 (Mar. 2, 1999).
Ward et al., "The angiopoietins and Tie2/Tek: adding to the complexity of cardiovascular development" *Semin Cell Dev Biol.* 13(1):19-27 (Feb. 2002).
Warren et al., "Regulation by vascular endothelial growth factor of human colon cancer tumorigenesis in a mouse model of experimental liver metastasis" *J. Clin. Invest.* 95(4):1789-1797 (Apr. 1995).
Wedge et al., "ZD4190: an orally active inhibitor of vascular endothelial growth factor signaling with broad-spectrum antitumor efficacy" *Cancer Research* 60(4):970-975 (Feb. 15, 2000).
Wiesner et al., "Food restriction regulates adipose-specific cytokines in pituitary gland but not in hypothalamus" *J Endocrinol.* 180(3):R1-R6 (Mar. 2004).
Wood et al., "PTK787/ZK 222584, a novel and potent inhibitor of vascular endothelial growth factor receptor tyrosine kinases, impairs vascular endothelial growth factor-induced responses and tumor growth after oral administration" *Cancer Research* 60(8):2178-2189 (Apr. 15, 2000).
Wu and Wu, "Delivery systems for gene therapy" *Biotherapy* 3(1):87-95 (1991).
Xu et al., "Angiopoietin-like protein 4 decreases blood glucose and improves glucose tolerance but induces hyperlipidemia and hepatic steatosis in mice" *Proc Natl Acad Sci USA.* 102(17):6086-6091 (Apr. 26, 2005).
Yang, Jun et al., "Galactosylated alginate as a scaffold for hepatocytes entrapment" *Biomaterials* 23:471-479 (2002).
Yoon et al., "Peroxisome proliferator-activated receptor gamma target gene encoding a novel angiopoietin-related protein associated with adipose differentiation" *Mol Cell Biol.* 20(14):5343-5349 (Jul. 2000).
Yoshida et al., "Angiopoietin-like protein 4 is a potent hyperlipidemia-inducing factor in mice and inhibitor of lipoprotein lipase" *J Lipid Res.* 43(11):1770-1772 (Nov. 2002).
Yu et al., "Inhibition of cardiac lipoprotein utilization by transgenic overexpression of Angptl4 in the heart" *Natl Acad Sci USA.* 102(5):1767-1772 (Feb. 1, 2005).
Zamecnik et al., "Inhibition of Replication and Expression of Human T-Cell Lymphotropic Virus Type III in Cultured Cells by Exogenous Synthetic Oligonucleotides Complementary to Viral RNA" *Proc. Natl. Acad. Sci.* 83:4143-4146 (Jun. 1986).
Zhu H. et al., "Expression and function of hepatocellular carcinoma-related gene pp1158 (NCBI Abstract)" (Oncogene & Related Genes National Laboratory Shanghai Cancer Institute, Shanghai, China) (Mar. 2002).
Wadhwa, et al., Know-how of RNA interference and its applications in research and therapy. *Mutation Research*, 567:71-84 (2004).
GenBank Accession No. BF337379.

* cited by examiner

SEQ. ID NO:1:

```
GCCGAGCTGA GCGGATCCTC ACATGACTGT GATCCGATTC TTTCCAGCGG 50
CTTCTGCAAC CAAGCGGGTC TTACCCCCGG TCCTCCGCGT CTCCAGTCCT 100
CGCACCTGGA ACCCCAACGT CCCCGAGAGT CCCCGAATCC CCGCTCCCAG 150
GCTACCTAAG AGGATGAGCG GTGCTCCGAC GGCCGGGGCA GCCCTGATGC 200
TCTGCGCCGC CACCGCCGTG CTACTGAGCG CTCAGGGCGG ACCCGTGCAG 250
TCCAAGTCGC CGCGCTTTGC GTCCTGGGAC GAGATGAATG TCCTGGCGCA 300
CGGACTCCTG CAGCTCGGCC AGGGGCTGCG CGAACACGCG GAGCGCACCC 350
GCAGTCAGCT GAGCGCGCTG GAGCGGCGCC TGAGCGCGTG CGGGTCCGCC 400
TGTCAGGGAA CCGAGGGGTC CACCGACCTC CCGTTAGCCC CTGAGAGCCG 450
GGTGGACCCT GAGGTCCTTC ACAGCCTGCA GACACAACTC AAGGCTCAGA 500
ACAGCAGGAT CCAGCAACTC TTCCACAAGG TGGCCCAGCA GCAGCGGCAC 550
CTGGAGAAGC AGCACCTGCG AATTCAGCAT CTGCAAAGCC AGTTTGGCCT 600
CCTGGACCAC AAGCACCTAG ACCATGAGGT GGCCAAGCCT GCCCGAAGAA 650
AGAGGCTGCC CGAGATGGCC CAGCCAGTTG ACCCGGCTCA CAATGTCAGC 700
CGCCTGCACC GGCTGCCCAG GGATTGCCAG GAGCTGTTCC AGGTTGGGGA 750
GAGGCAGAGT GGACTATTTG AAATCCAGCC TCAGGGTCT CCGCCATTTT 800
TGGTGAACTG CAAGATGACC TCAGATGGAG GCTGGACAGT AATTCAGAGG 850
CGCCACGATG GCTCAGTGGA CTTCAACCGG CCCTGGGAAG CCTACAAGGC 900
GGGGTTTGGG GATCCCCACG GCGAGTTCTG GCTGGGTCTG GAGAAGGTGC 950
ATAGCATCAC GGGGGACCGC AACAGCCGCC TGGCCGTGCA GCTGCGGGAC 1000
TGGGATGGCA ACGCCGAGTT GCTGCAGTTC TCCGTGCACC TGGGTGGCGA 1050
GGACACGGCC TATAGCCTGC AGCTCACTGC ACCCGTGGCC GGCCAGCTGG 1100
GCGCCACCAC CGTCCCACCC AGCGGCCTCT CCGTACCCTT CTCCACTTGG 1150
GACCAGGATC ACGACCTCCG CAGGGACAAG AACTGCGCCA AGAGCCTCTC 1200
```

FIG._1A

```
TGGAGGCTGG TGGTTTGGCA CCTGCAGCCA TTCCAACCTC AACGGCCAGT 1250
ACTTCCGCTC CATCCCACAG CAGCGGCAGA AGCTTAAGAA GGGAATCTTC 1300
TGGAAGACCT GGCGGGGCCG CTACTACCCG CTGCAGGCCA CCACCATGTT 1350
GATCCAGCCC ATGGCAGCAG AGGCAGCCTC CTAGCGTCCT GGCTGGGCCT 1400
GGTCCCAGGC CCACGAAAGA CGGTGACTCT TGGCTCTGCC CGAGGATGTG 1450
GCCGTTCCCT GCCTGGGCAG GGGCTCCAAG GAGGGGCCAT CTGGAAACTT 1500
GTGGACAGAG AAGAAGACCA CGACTGGAGA AGCCCCCTTT CTGAGTGCAG 1550
GGGGGCTGCA TGCGTTGCCT CCTGAGATCG AGGCTGCAGG ATATGCTCAG 1600
ACTCTAGAGG CGTGGACCAA GGGGCATGGA GCTTCACTCC TTGCTGGCCA 1650
GGGAGTTGGG GACTCAGAGG GACCACTTGG GGCCAGCCAG ACTGGCCTCA 1700
ATGGCGGACT CAGTCACATT GACTGACGGG GACCAGGGCT TGTGTGGGTC 1750
GAGAGCGCCC TCATGGTGCT GGTGCTGTTG TGTGTAGGTC CCTGGGGAC 1800
ACAAGCAGGC GCCAATGGTA TCTGGGCGGA GCTCACAGAG TTCTTGGAAT 1850
AAAAGCAACC TCAGAACAC 1869
```

FIG._1B

SEQ. ID NO:2:

| | | | | | | | | | | | | | | |
|---|---|---|---|---|---|---|---|---|---|---|---|---|---|---|
|Met|Ser|Gly|Ala|Pro|Thr|Ala|Gly|Ala|Ala|Leu|Met|Leu|Cys|Ala|
|1| | | |5| | | | |10| | | | |15|
|Ala|Thr|Ala|Val|Leu|Leu|Ser|Ala|Gln|Gly|Gly|Pro|Val|Gln|Ser|
| | | | |20| | | | |25| | | | |30|
|Lys|Ser|Pro|Arg|Phe|Ala|Ser|Trp|Asp|Glu|Met|Asn|Val|Leu|Ala|
| | | | |35| | | | |40| | | | |45|
|His|Gly|Leu|Leu|Gln|Leu|Gly|Gln|Gly|Leu|Arg|Glu|His|Ala|Glu|
| | | | |50| | | | |55| | | | |60|
|Arg|Thr|Arg|Ser|Gln|Leu|Ser|Ala|Leu|Glu|Arg|Arg|Leu|Ser|Ala|
| | | | |65| | | | |70| | | | |75|
|Cys|Gly|Ser|Ala|Cys|Gln|Gly|Thr|Glu|Gly|Ser|Thr|Asp|Leu|Pro|
| | | | |80| | | | |85| | | | |90|
|Leu|Ala|Pro|Glu|Ser|Arg|Val|Asp|Pro|Glu|Val|Leu|His|Ser|Leu|
| | | | |95| | | | |100| | | | |105|
|Gln|Thr|Gln|Leu|Lys|Ala|Gln|Asn|Ser|Arg|Ile|Gln|Gln|Leu|Phe|
| | | | |110| | | | |115| | | | |120|
|His|Lys|Val|Ala|Gln|Gln|Gln|Arg|His|Leu|Glu|Lys|Gln|His|Leu|
| | | | |125| | | | |130| | | | |135|
|Arg|Ile|Gln|His|Leu|Gln|Ser|Gln|Phe|Gly|Leu|Leu|Asp|His|Lys|
| | | | |140| | | | |145| | | | |150|
|His|Leu|Asp|His|Glu|Val|Ala|Lys|Pro|Ala|Arg|Arg|Lys|Arg|Leu|
| | | | |155| | | | |160| | | | |165|
|Pro|Glu|Met|Ala|Gln|Pro|Val|Asp|Pro|Ala|His|Asn|Val|Ser|Arg|
| | | | |170| | | | |175| | | | |180|
|Leu|His|Arg|Leu|Pro|Arg|Asp|Cys|Gln|Glu|Leu|Phe|Gln|Val|Gly|
| | | | |185| | | | |190| | | | |195|
|Glu|Arg|Gln|Ser|Gly|Leu|Phe|Glu|Ile|Gln|Pro|Gln|Gly|Ser|Pro|
| | | | |200| | | | |205| | | | |210|
|Pro|Phe|Leu|Val|Asn|Cys|Lys|Met|Thr|Ser|Xaa|Gly|Gly|Trp|Thr|
| | | | |215| | | | |220| | | | |225|
|Val|Ile|Gln|Arg|Arg|His|Asp|Gly|Ser|Val|Asp|Phe|Asn|Arg|Pro|
| | | | |230| | | | |235| | | | |240|

FIG._2A

```
Trp Glu Ala Tyr Lys Ala Gly Phe Gly Asp Pro His Gly Glu Phe
            245             250                 255

Trp Leu Gly Leu Glu Lys Val His Ser Ile Thr Gly Asp Arg Asn
            260             265                 270

Ser Arg Leu Ala Val Gln Leu Arg Asp Trp Asp Gly Asn Ala Glu
            275             280                 285

Leu Leu Gln Phe Ser Val His Leu Gly Gly Glu Asp Thr Ala Tyr
            290             295                 300

Ser Leu Gln Leu Thr Ala Pro Val Ala Gly Gln Leu Gly Ala Thr
            305             310                 315

Thr Val Pro Pro Ser Gly Leu Ser Val Pro Phe Ser Thr Trp Asp
            320             325                 330

Gln Asp His Asp Leu Arg Arg Asp Lys Asn Cys Ala Lys Ser Leu
            335             340                 345

Ser Gly Gly Trp Trp Phe Gly Thr Cys Ser His Ser Asn Leu Asn
            350             355                 360

Gly Gln Tyr Phe Arg Ser Ile Pro Gln Gln Arg Gln Lys Leu Lys
            365             370                 375

Lys Gly Ile Phe Trp Lys Thr Trp Arg Gly Arg Tyr Tyr Pro Leu
            380             385                 390

Gln Ala Thr Thr Met Leu Ile Gln Pro Met Ala Ala Glu Ala Ala
            395             400                 405

Ser
406
```

FIG._2B

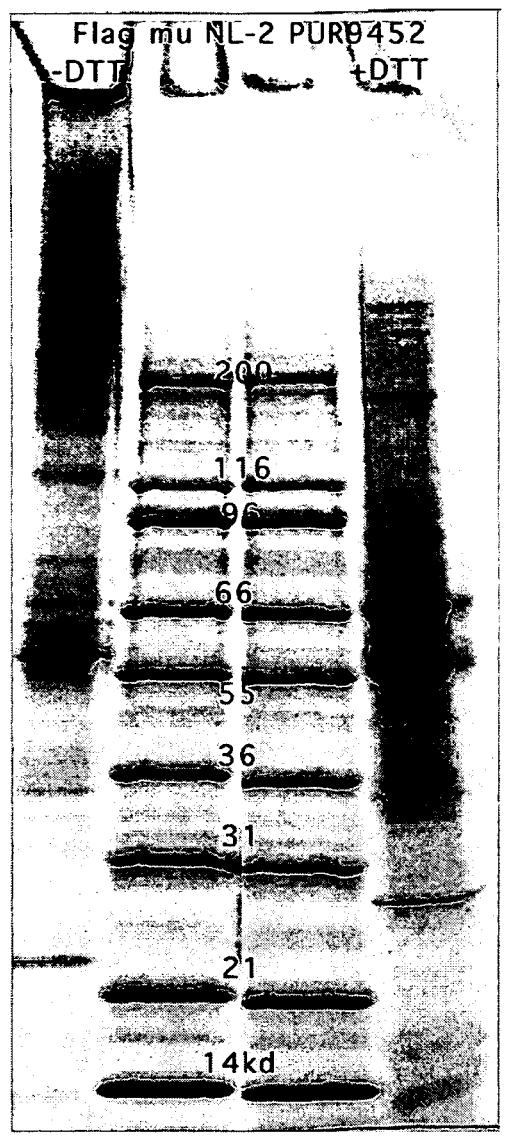
FIG._3A
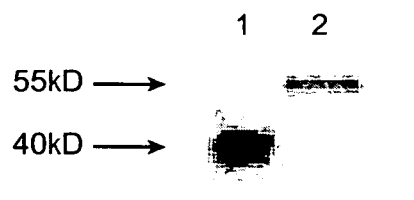
FIG._3B

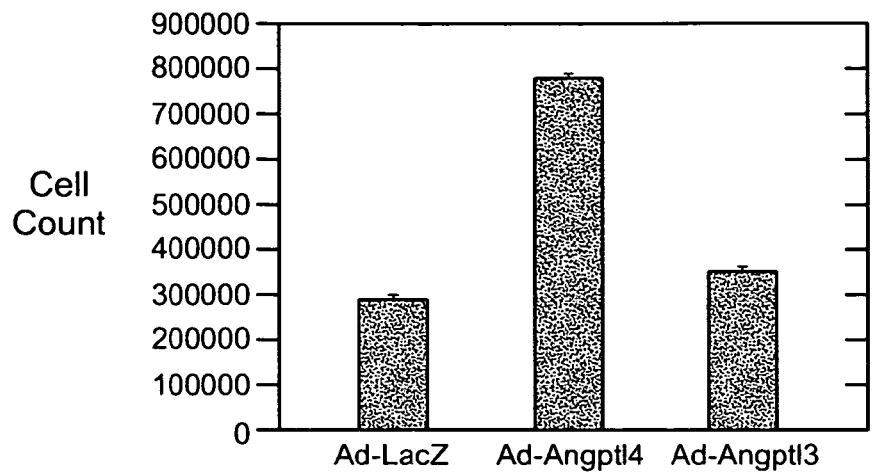
FIG._4A
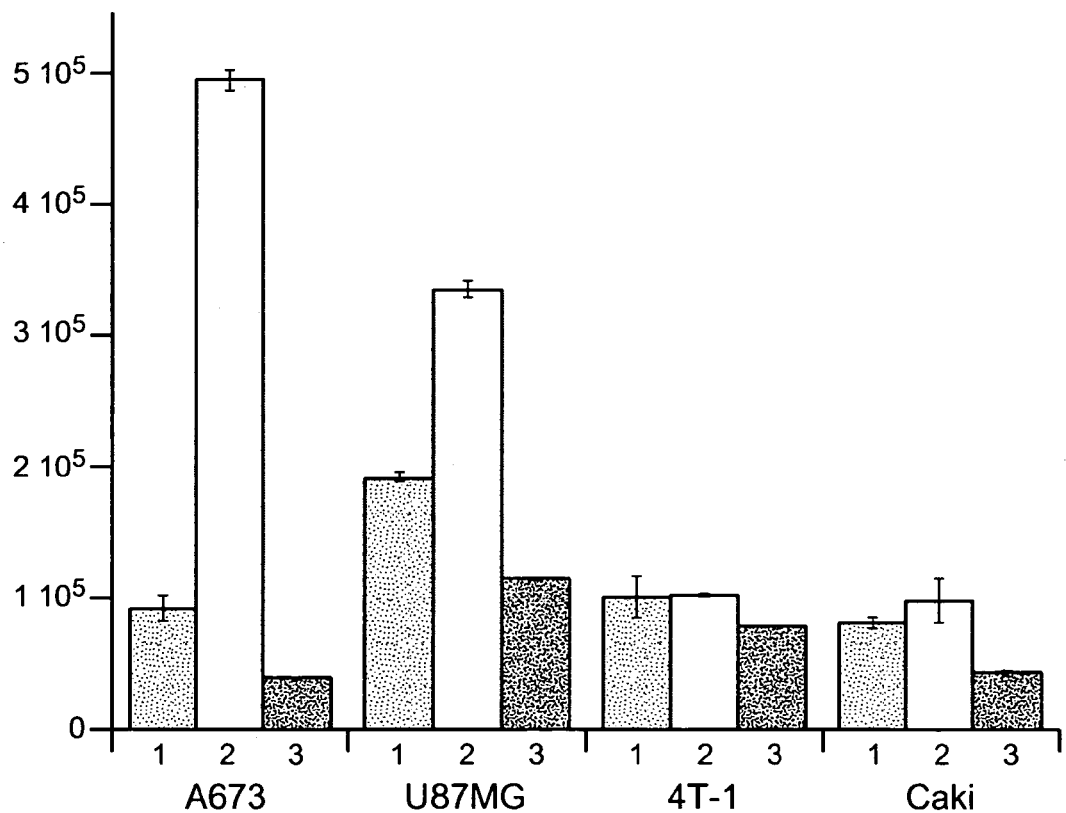
FIG._4B

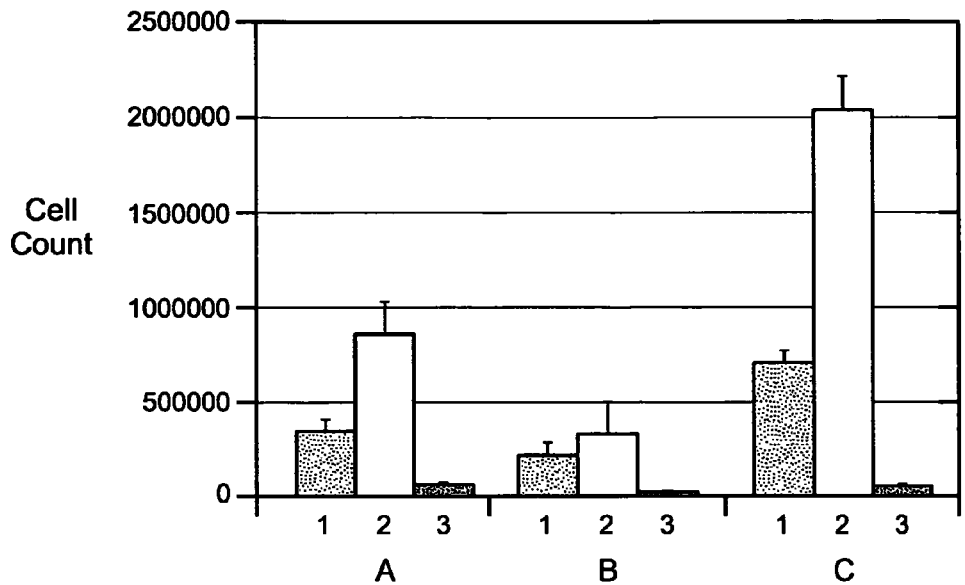
FIG._4C
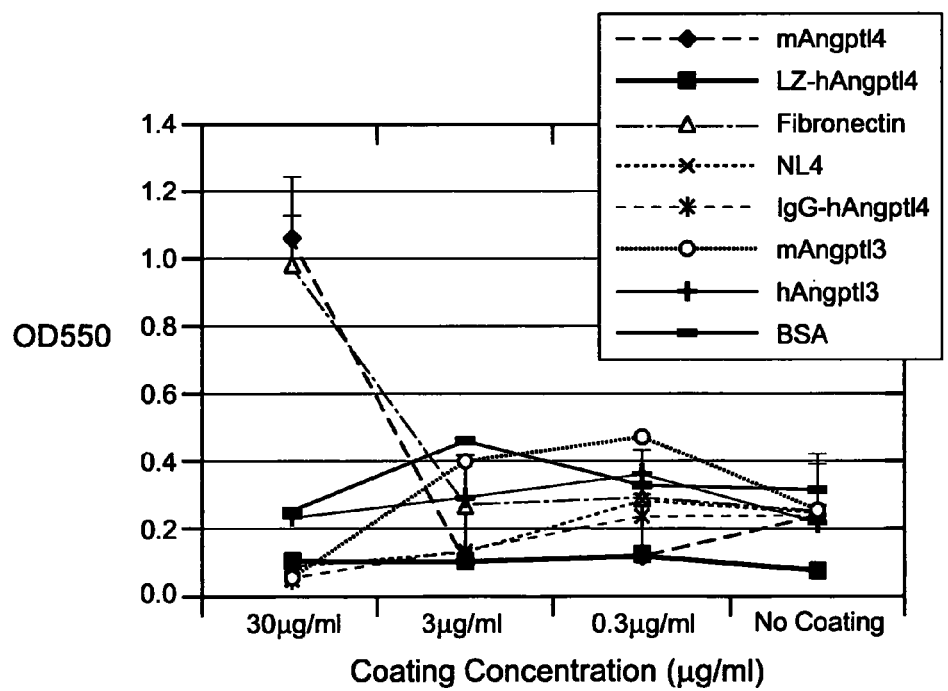
FIG._5

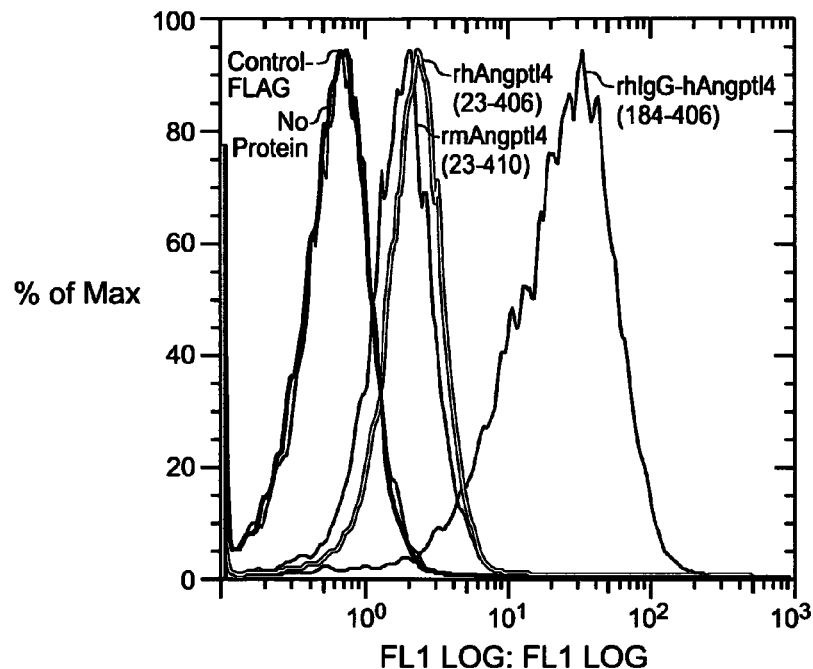
FIG._6A
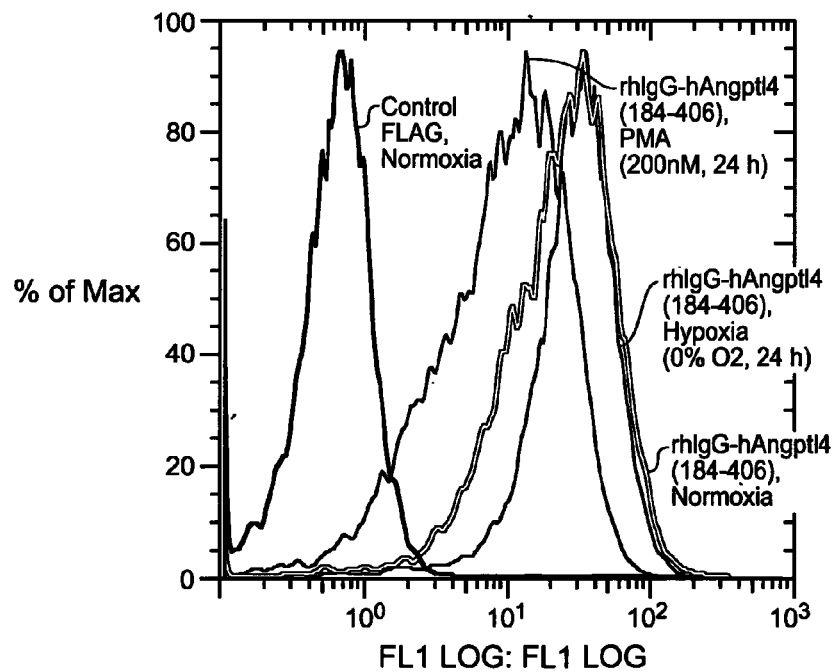
FIG._6B

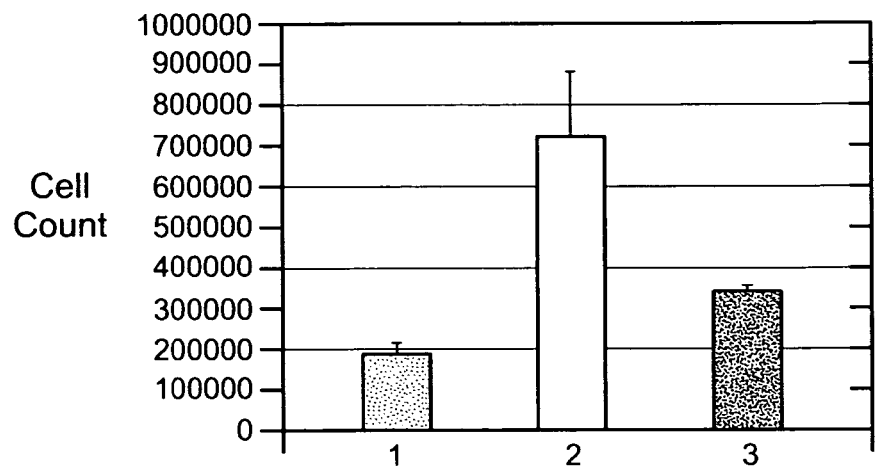
FIG._7A
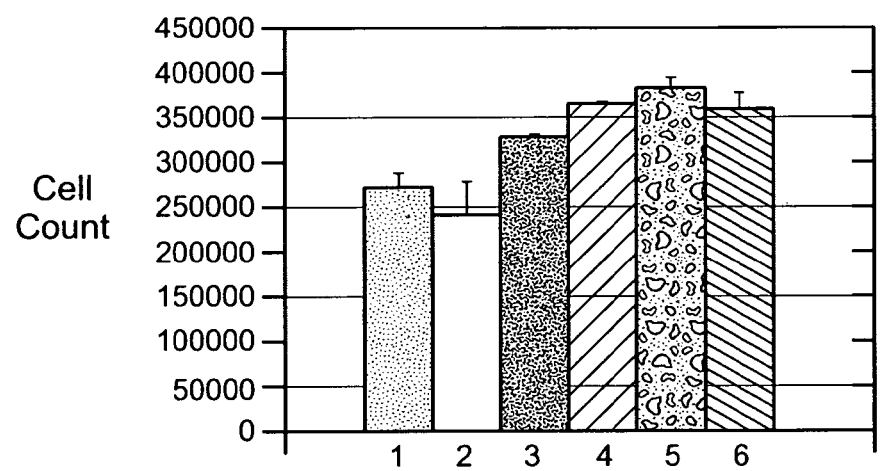
FIG._7B

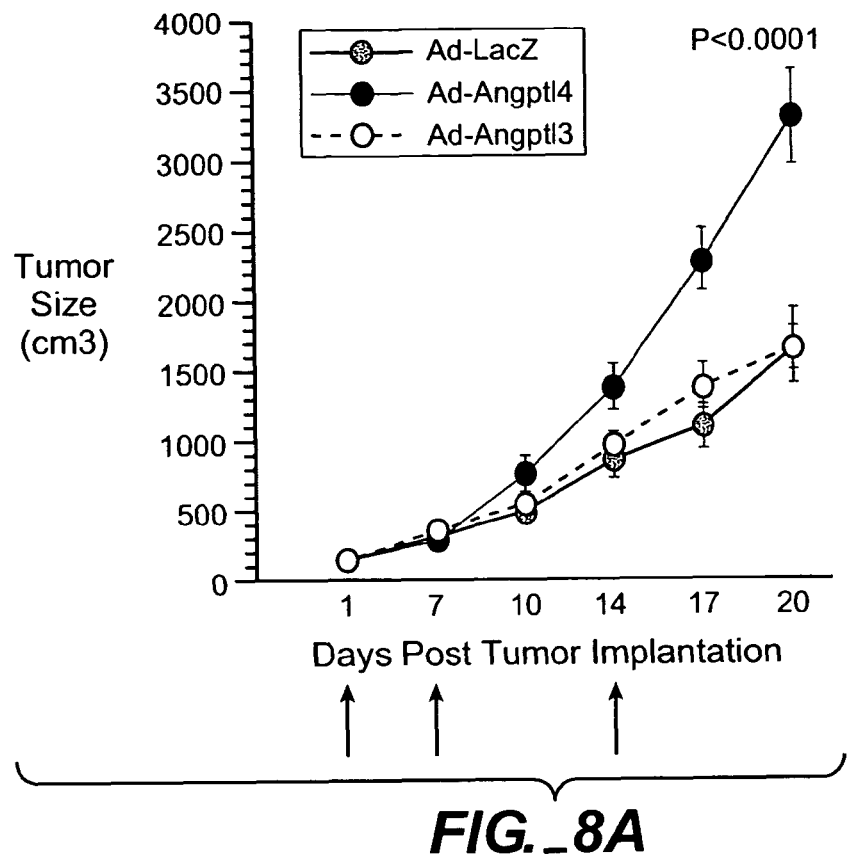
FIG._8A
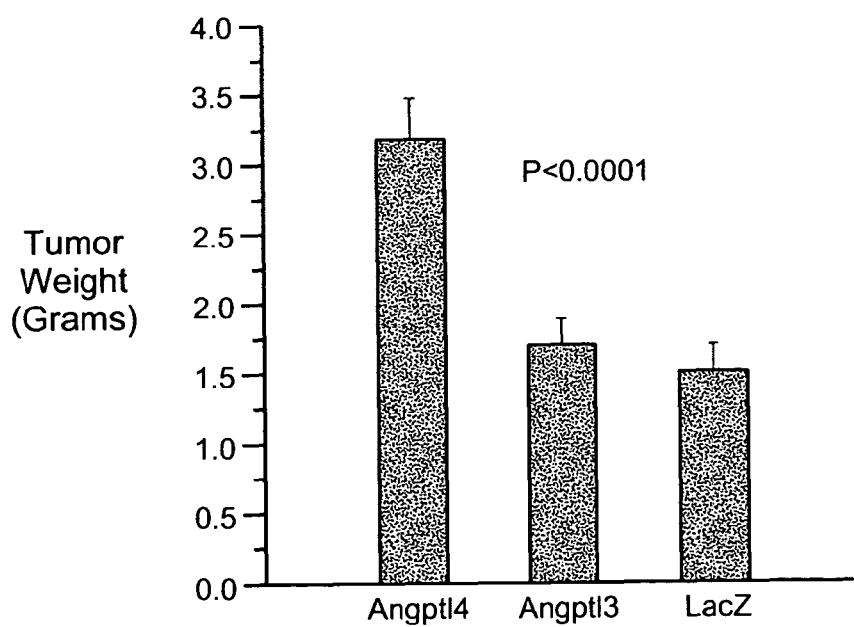
FIG._8B

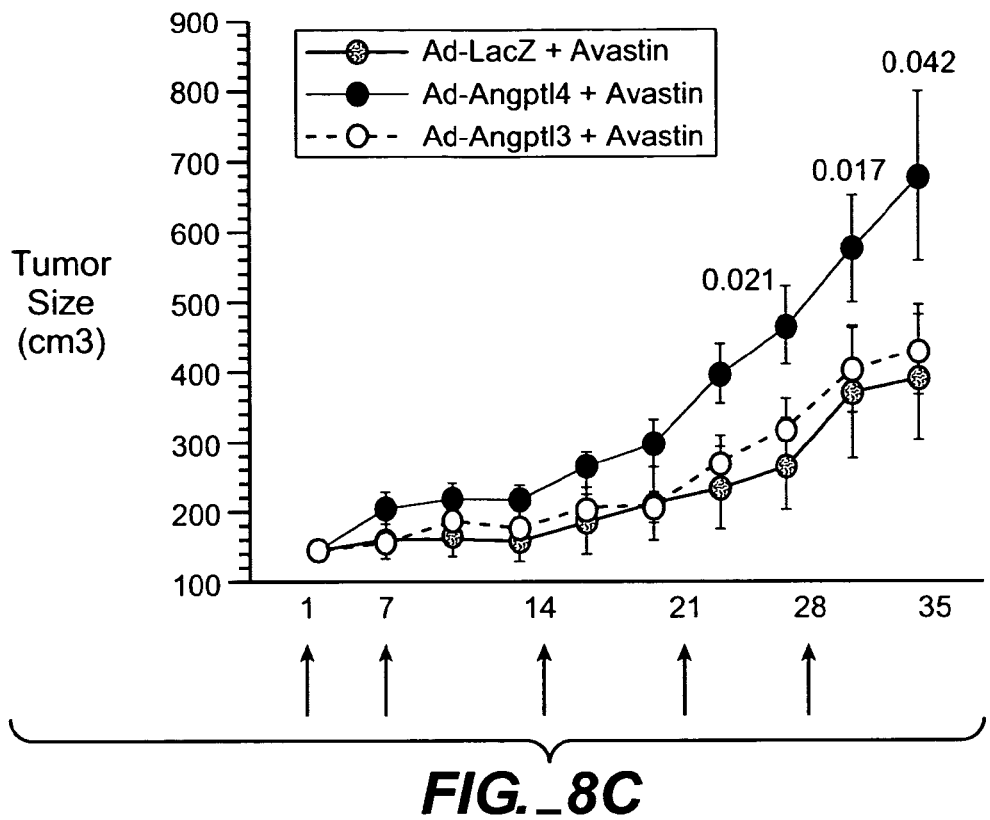
FIG._8C
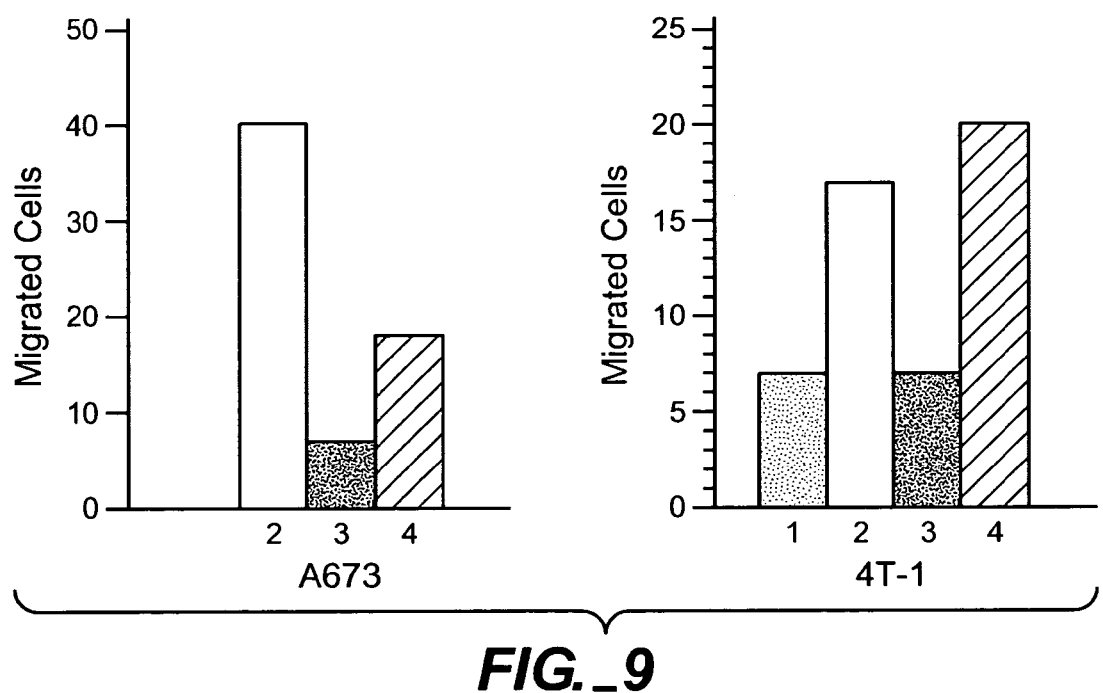
FIG._9

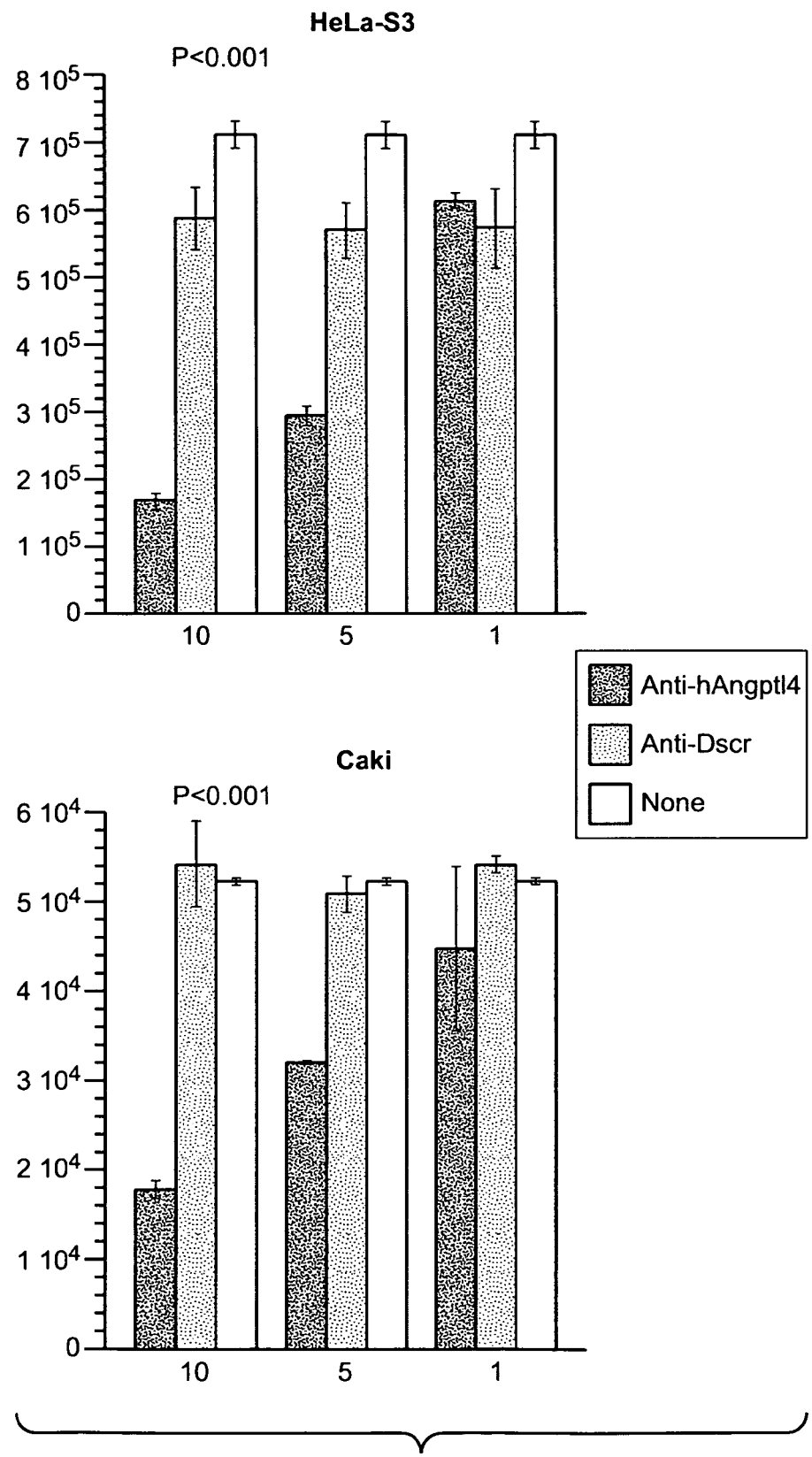
FIG._10A

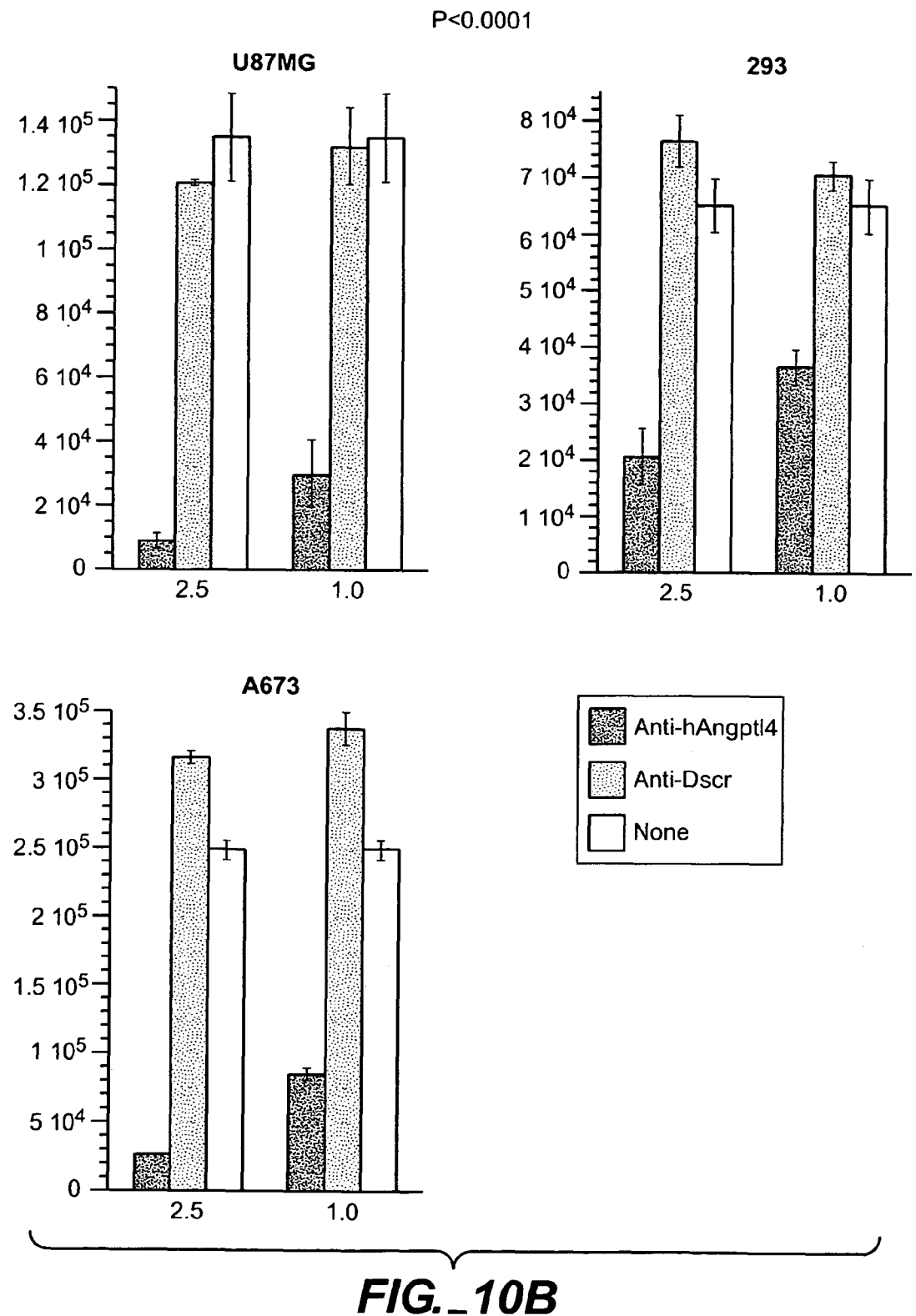
FIG._10B

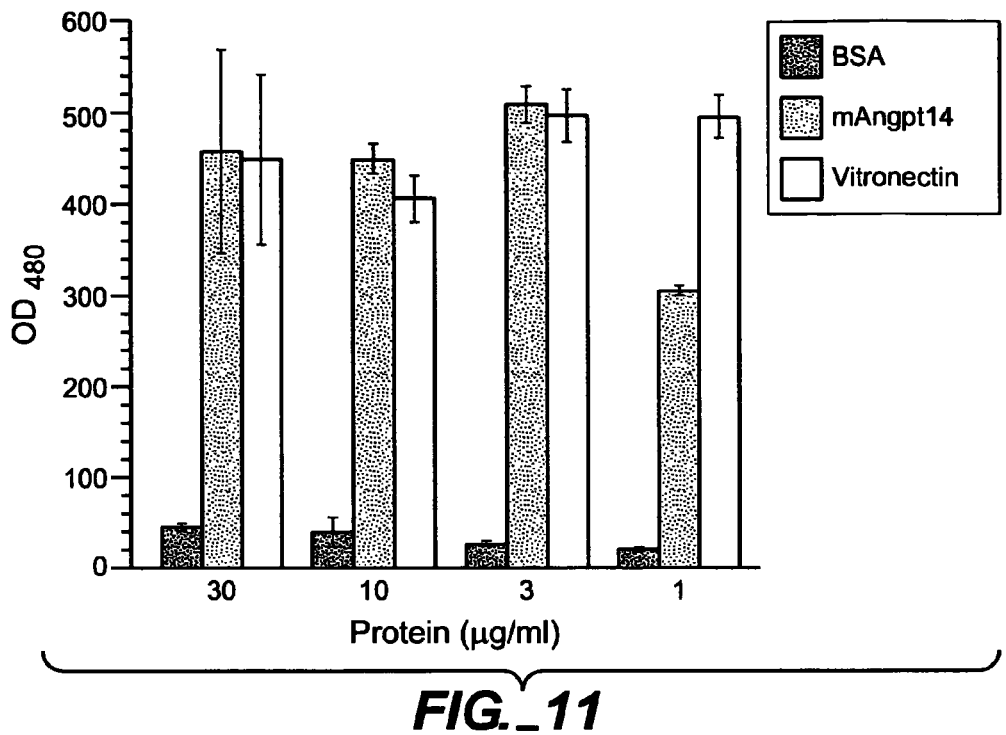
FIG._11
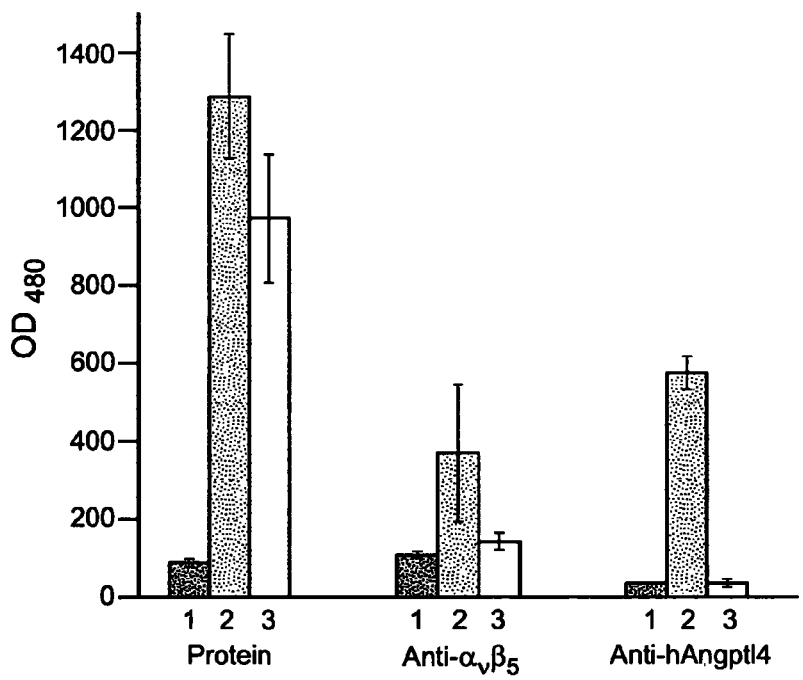
FIG._12

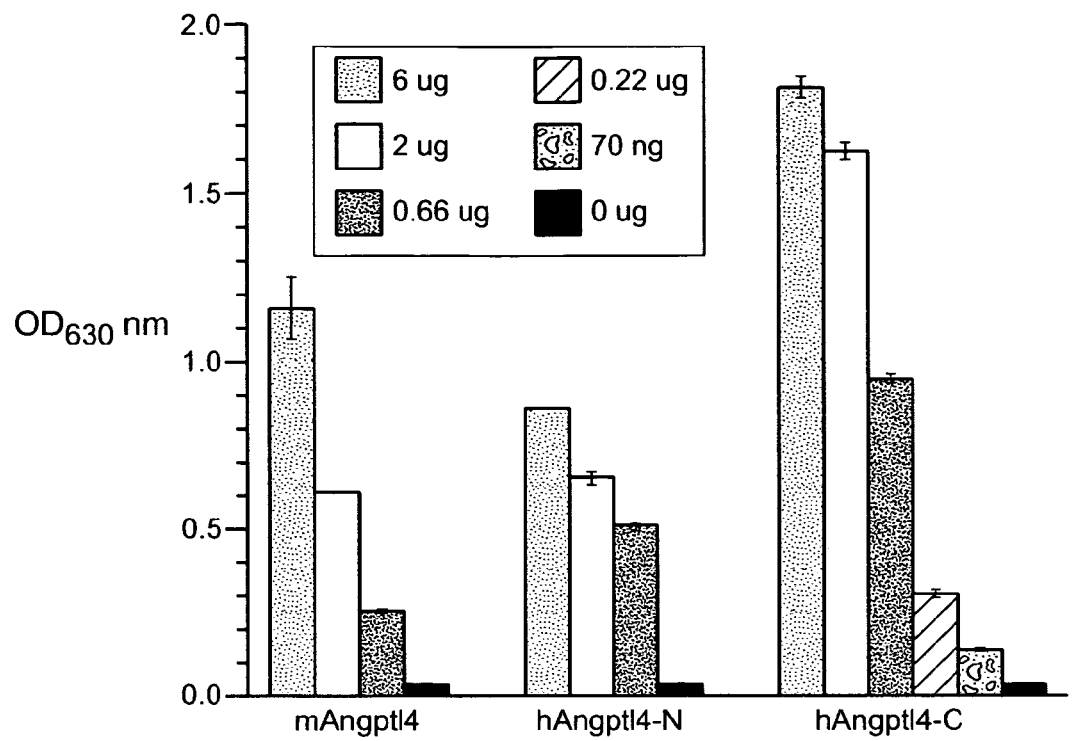
FIG._13A
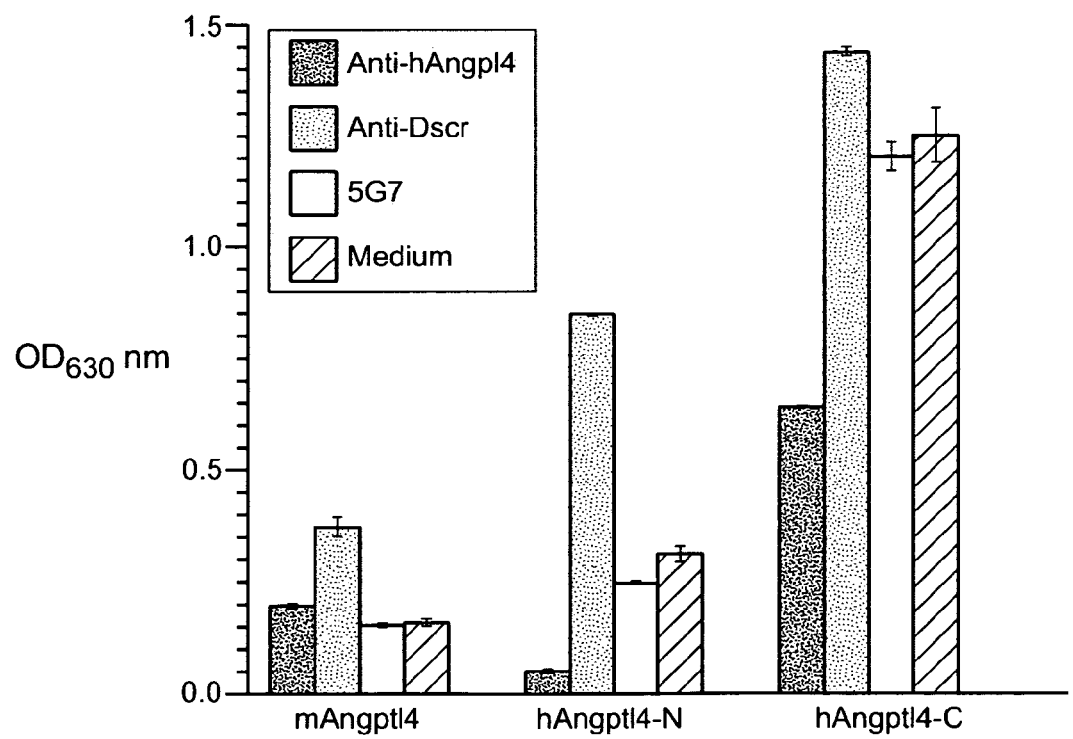
FIG._13B

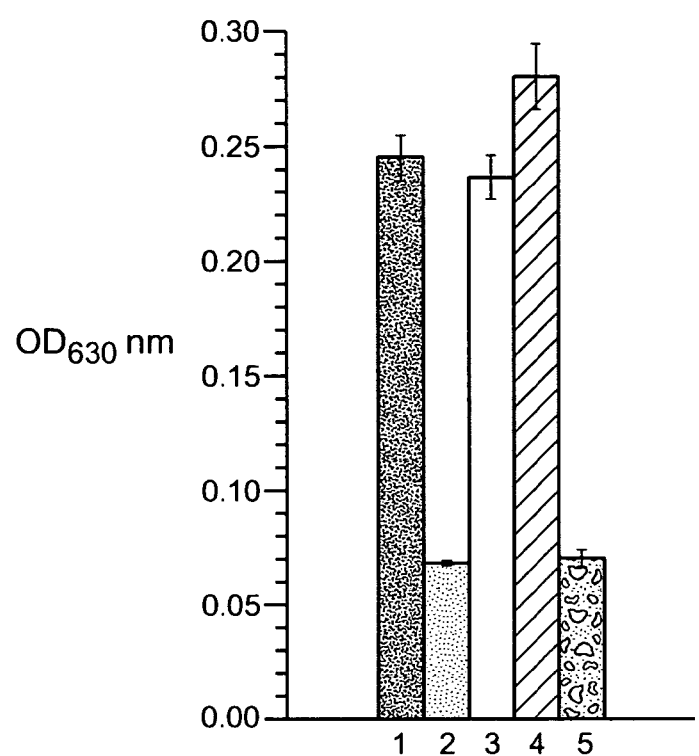
FIG._13C

SEQUENCE LISTING

```
<160> NUMBER OF SEQ ID NOS: 5

<210> SEQ ID NO 1
<211> LENGTH: 1869
<212> TYPE: DNA
<213> ORGANISM: Homo sapiens

<400> SEQUENCE: 1
gccgagctga gcggatcctc acatgactgt gatccgattc tttccagcgg            50
cttctgcaac caagcgggtc ttaccccgg tcctccgcgt ctccagtcct            100
cgcacctgga accccaacgt ccccgagagt ccccgaatcc ccgctcccag           150
gctacctaag aggatgagcg gtgctccgac ggccggggca gccctgatgc           200
tctgcgccgc caccgccgtg ctactgagcg ctcagggcgg acccgtgcag           250
tccaagtcgc cgcgctttgc gtcctgggac gagatgaatg tcctggcgca           300
cggactcctg cagctcggcc aggggctgcg cgaacacgcg gagcgcaccc           350
gcagtcagct gagcgcgctg gagcggcgcc tgagcgcgtg cgggtccgcc           400
tgtcagggaa ccgaggggtc caccgacctc ccgttagccc ctgagagccg           450
ggtggaccct gaggtccttc acagcctgca gacacaactc aaggctcaga           500
acagcaggat ccagcaactc ttccacaagg tgcccagca gcagcggcac            550 ctggagaagc agcacctgcg aattcagcat ctgcaaagcc agtttggcct           600
cctggaccac aagcacctag accatgaggt ggccaagcct gcccgaagaa           650
agaggctgcc cgagatggcc cagccagttg acccggctca caatgtcagc           700
cgcctgcacc ggctgcccag ggattgccag gagctgttcc aggttgggga           750
gaggcagagt ggactatttg aaatccagcc tcagggtct ccgccatttt            800 tggtgaactg caagatgacc tcagatggag gctggacagt aattcagagg           850
cgccacgatg gctcagtgga cttcaaccgg ccctgggaag cctacaaggc           900
ggggtttggg gatccccacg gcgagttctg gctgggtctg gagaaggtgc           950
atagcatcac gggggaccgc aacagccgcc tggccgtgca gctgcgggac           1000
tgggatggca cgccgagtt gctgcagttc tccgtgcacc tgggtggcga            1050
ggacacggcc tatagcctgc agctcactgc acccgtggcc ggccagctgg           1100
gcgccaccac cgtcccaccc agcggcctct ccgtacccct ctccacttgg           1150
```

```
gaccaggatc acgacctccg cagggacaag aactgcgcca agagcctctc    1200
tggaggctgg tggtttggca cctgcagcca ttccaacctc aacggccagt    1250
acttccgctc catcccacag cagcggcaga agcttaagaa gggaatcttc    1300
tggaagacct ggcggggccg ctactacccg ctgcaggcca ccaccatgtt    1350
gatccagccc atggcagcag aggcagcctc ctagcgtcct ggctgggcct    1400
ggtcccaggc ccacgaaaga cggtgactct tggctctgcc cgaggatgtg    1450
gccgttccct gcctgggcag gggctccaag gaggggccat ctggaaactt    1500
gtggacagag aagaagacca cgactggaga agccccctttt ctgagtgcag    1550 gggggctgca tgcgttgcct cctgagatcg aggctgcagg atatgctcag    1600
actctagagg cgtggaccaa ggggcatgga gcttcactcc ttgctggcca    1650
gggagttggg gactcagagg gaccacttgg ggccagccag actggcctca    1700
atggcggact cagtcacatt gactgacggg gaccagggct tgtgtgggtc    1750
gagagcgccc tcatggtgct ggtgctgttg tgtgtaggtc ccctggggac    1800
acaagcaggc gccaatggta tctgggcgga gctcacagag ttcttggaat    1850
aaaagcaacc tcagaacac                                       1869
```

<210> SEQ ID NO 2
<211> LENGTH: 406
<212> TYPE: PRT
<213> ORGANISM: Homo sapiens
<220> FEATURE:
<221> NAME/KEY: Unsure
<222> LOCATION: 221
<223> OTHER INFORMATION: Unknown amino acid

<400> SEQUENCE: 2

```
Met Ser Gly Ala Pro Thr Ala Gly Ala Ala Leu Met Leu Cys Ala
 1               5                  10                  15

Ala Thr Ala Val Leu Leu Ser Ala Gln Gly Gly Pro Val Gln Ser
                20                  25                  30

Lys Ser Pro Arg Phe Ala Ser Trp Asp Glu Met Asn Val Leu Ala
                35                  40                  45

His Gly Leu Leu Gln Leu Gly Gln Gly Leu Arg Glu His Ala Glu
                50                  55                  60

Arg Thr Arg Ser Gln Leu Ser Ala Leu Glu Arg Arg Leu Ser Ala
                65                  70                  75

Cys Gly Ser Ala Cys Gln Gly Thr Glu Gly Ser Thr Asp Leu Pro
                80                  85                  90

Leu Ala Pro Glu Ser Arg Val Asp Pro Glu Val Leu His Ser Leu
                95                  100                 105

Gln Thr Gln Leu Lys Ala Gln Asn Ser Arg Ile Gln Gln Leu Phe
                110                 115                 120

His Lys Val Ala Gln Gln Gln Arg His Leu Glu Lys Gln His Leu
                125                 130                 135

Arg Ile Gln His Leu Gln Ser Gln Phe Gly Leu Leu Asp His Lys
                140                 145                 150

His Leu Asp His Glu Val Ala Lys Pro Ala Arg Arg Lys Arg Leu
                155                 160                 165

Pro Glu Met Ala Gln Pro Val Asp Pro Ala His Asn Val Ser Arg
                170                 175                 180

Leu His Arg Leu Pro Arg Asp Cys Gln Glu Leu Phe Gln Val Gly
                185                 190                 195
```

```
Glu Arg Gln Ser Gly Leu Phe Glu Ile Gln Pro Gln Gly Ser Pro
            200                 205                 210

Pro Phe Leu Val Asn Cys Lys Met Thr Ser Xaa Gly Gly Trp Thr
            215                 220                 225

Val Ile Gln Arg Arg His Asp Gly Ser Val Asp Phe Asn Arg Pro
            230                 235                 240

Trp Glu Ala Tyr Lys Ala Gly Phe Gly Asp Pro His Gly Glu Phe
            245                 250                 255

Trp Leu Gly Leu Glu Lys Val His Ser Ile Thr Gly Asp Arg Asn
            260                 265                 270

Ser Arg Leu Ala Val Gln Leu Arg Asp Trp Asp Gly Asn Ala Glu
            275                 280                 285

Leu Leu Gln Phe Ser Val His Leu Gly Gly Glu Asp Thr Ala Tyr
            290                 295                 300

Ser Leu Gln Leu Thr Ala Pro Val Ala Gly Gln Leu Gly Ala Thr
            305                 310                 315

Thr Val Pro Pro Ser Gly Leu Ser Val Pro Phe Ser Thr Trp Asp
            320                 325                 330

Gln Asp His Asp Leu Arg Arg Asp Lys Asn Cys Ala Lys Ser Leu
            335                 340                 345

Ser Gly Gly Trp Trp Phe Gly Thr Cys Ser His Ser Asn Leu Asn
            350                 355                 360

Gly Gln Tyr Phe Arg Ser Ile Pro Gln Gln Arg Gln Lys Leu Lys
            365                 370                 375

Lys Gly Ile Phe Trp Lys Thr Trp Arg Gly Arg Tyr Tyr Pro Leu
            380                 385                 390

Gln Ala Thr Thr Met Leu Ile Gln Pro Met Ala Ala Glu Ala Ala
            395                 400                 405

Ser

<210> SEQ ID NO 3
<211> LENGTH: 21
<212> TYPE: DNA
<213> ORGANISM: Homo sapiens

<400> SEQUENCE: 3
gtggccaagc ctgcccgaag a                                                   21

<210> SEQ ID NO 4
<211> LENGTH: 21
<212> TYPE: RNA
<213> ORGANISM: Artificial sequence
<220> FEATURE:
<223> OTHER INFORMATION: sequence is synthesized

<400> SEQUENCE: 4
ggccaagccu gcccgaagau u                                                   21

<210> SEQ ID NO 5
<211> LENGTH: 21
<212> TYPE: RNA
<213> ORGANISM: Artificial sequence
<220> FEATURE:
<223> OTHER INFORMATION: sequence is synthesized

<400> SEQUENCE: 5
ucuucgggca ggcuuggcca c                                                   21
```

INHIBITORS OF ANGIOPOIETIN-LIKE 4 PROTEIN, COMBINATIONS, AND THEIR USE

RELATED APPLICATION

This application is a divisional of, and claims priority under 35 USC §120 to U.S. application Ser. No. 11/185,215, filed Jul. 19, 2005 (now U.S. Pat. No. 7,740,846). The Ser. No. 11/185,215 application claims priority under 35 USC §119(e) and the benefit of U.S. Provisional Application Ser. No. 60/589,782, filed Jul. 20, 2004.

FIELD OF THE INVENTION

This invention relates in general to treatment of human diseases and pathological conditions, such as cancer. The invention concerns inhibitors of angiopoietin-like 4 protein (ANGPTL4) and combinations of inhibitors of ANGPTL4 with other therapeutics, and methods of using such compositions for the diagnosis and treatment of diseases or pathological conditions.

BACKGROUND OF THE INVENTION

Cancer is a leading cause of death in the United States. Various types of therapies have been used to treat cancer. For example, surgical methods are used to remove cancerous or dead tissue. Radiotherapy, which works by shrinking solid tumors, and chemotherapy, which kills rapidly dividing cells, are used as cancer therapies.

In 1971, Folkman proposed that anti-angiogenesis might be an effective anticancer strategy. Folkman, *N. Engl. J. Med.* 285, 1182-1186 (1971). Angiogenesis is the development of new vasculature from preexisting blood vessels and/or circulating endothelial stem cells (see, e.g., Ferrara & Alitalo, *Nature Medicine* 5(12)1359-1364 (1999)). Angiogenesis is a cascade of process consisting of 1) degradation of the extracellular matrix of a local venue after the release of protease, 2) proliferation of capillary endothelial cells, and 3) migration of capillary tubules toward the angiogenic stimulus. Ferrara et al. *Endocrine Rev.* 13:18-32 (1992).

The growth of new blood vessels is a prerequisite during normal physiological processes of embryonic and postnatal development, e.g., embryogenesis, wound healing and menstruation. See, e.g., Folkman and Klagsbrun *Science* 235:442-447 (1987). Such proliferation of new blood vessels from pre-existing capillaries additionally plays a key role in the pathological development of a variety of disorders, including but not limited to, e.g., tumors, proliferative retinopathies, age-related macular degeneration, psoriasis, inflammation, diabetes, and rheumatoid arthritis (RA). See, e.g., Ferrara, *Recent Prog. Horm. Res.* 55:15-35 (2000), discussion 35-6.

In view of the remarkable physiological and pathological importance of angiogenesis, much work has been dedicated to the elucidation of the factors capable of regulating this process. It is suggested that the angiogenesis process is regulated by a balance between pro- and anti-angiogenic molecules, and is derailed in various diseases, especially cancer. See, e.g., Carmeliet and Jain *Nature* 407:249-257 (2000).

For example, angiogenesis is dependent on secreted factors like Vascular endothelial growth factor-A (VEGF, also known as vascular permeability factor (VPF)) and fibroblast growth factor (FGF). See, e.g., Ferrara and Davis-Smyth *Endocrine Rev.* 18:4-25 (1997); and, Ferrara *J. Mol. Med.* 77:527-543 (1999). In addition to being an angiogenic factor in angiogenesis and vasculogenesis, VEGF, as a pleiotropic growth factor, exhibits multiple biological effects in other physiological processes, such as endothelial cell survival, vessel permeability and vasodilation, monocyte chemotaxis and calcium influx. Ferrara and Davis-Smyth (1997), supra. Moreover, studies have reported mitogenic effects of VEGF on a few non-endothelial cell types, such as retinal pigment epithelial cells, pancreatic duct cells and Schwann cells. See, e.g., Guerrin et al. *J. Cell Physiol.* 164:385-394 (1995); Oberg-Welsh et al. *Mol. Cell. Endocrinol.* 126:125-132 (1997); and, Sondell et al. *J. Neurosci.* 19:5731-5740 (1999).

VEGF belongs to a gene family that includes placental growth factor (PlGF), VEGF-B, VEGF-C, VEGF-D and VEGF-E. These ligands bind to and ligate to tyrosine kinase receptors expressed on endothelial cells. For example, VEGF tyrosine kinase receptor family includes Flt1 (VEGF-R1) (which binds ligands VEGF, VEGF-B and PlGF), Flk1/KDR (VEGF-R2) (which binds VEGF, VEGF-C, VEGF-D, and, VEGF-E), and Flt4 (VEGF-R3) (which binds VEGF-C and VEGF-D). See, e.g., Ferrara et al., *Nature Medicine* 9(6):669-676 (2003); and, Robinson & Stringer, *Journal of Cell Science,* 14(5):853-65 (2001).

The Angiopoietins are another group of growth factors for the vascular endothelium. See, e.g., Davis et al., *Cell,* 87:1161-1169 (1996); Suri et al., *Cell,* 87:1171-1180 (1996); Maisonpierre et al. *Science* 277:55-60 (1997); and Valenzuela et al., *Proc. Natl. Acad. Sci. USA* 96:1904-1909 (1999). Angiopoietins appear to work in a complementary and coordinate fashion with VEGF, where VEGF acts in vascular development while angiopoietins most likely act by modulating remodeling, maturation and stabilization of the vasculature. See, e.g., Holash et al., *Oncogene* 18:5356-5362 (1999). Angiopoietin 1, Angiopoietin 2, Angiopoietin 3 and Angiopoietin 4 bind to tyrosine kinase Tie2 (also know as Tek) receptors, which are receptors found on endothelial cells. See, e.g., Ward & Dumont, *Seminars in Cell & Developmental Biology,* 13:19-27 (2002). There is also a Tie1 orphan receptor.

Angiogenesis not only depends on growth factors, but is also influenced by cell adhesion molecules (CAMs), including integrins, binding to their ligands present within the extracellular matrix. See, e.g., Ferrara & Alitalo, *Nature Medicine* 5(12)1359-1364 (1999); and, Carmeliet, *Nature Medicine,* 6(3):389-395 (2000). Integrins facilitate cellular adhesion to and migration on the extracellular matrix proteins found in intercellular spaces and basement membranes. The integrin family of cell adhesion proteins is composed of at least 18α and 8β subunits that are expressed in at least 22αβ heterodimeric combinations. See, e.g., Byzova et al., *Mol. Cell.,* 6(4):851-860 (2000); and, Hood and Cheresh, *Nature Reviews,* 2:91-99 (2002). Among these, at least six ($\alpha_v\beta_3$, $\alpha_v\beta_5$, $\alpha_5\beta_1$, $\alpha_2\beta_1$, $\alpha_v\beta_1$ and $\alpha_1\beta_1$) of the combinations have been implicated in angiogenesis (see, e.g., Hynes and Bader, *Thromb. Haemost.,* 78(1):83-87 (1997); and, Hynes et al., *Braz. J. Med. Biol. Res.,* 32(5):501-510 (1999)). Inactivation of various genes encoding specific adhesion receptors or administration of blocking antibodies in animal models had profound effects on the angiogenic response of endothelial cells. See, e.g., Elicieri and Cheresh, *Mol. Med.,* 4:741-750 (1998).

These molecules have been targets for cancer therapies. For example, recognition of VEGF as a primary regulator of angiogenesis in pathological conditions has led to numerous attempts to block VEGF activities. Inhibitory anti-VEGF receptor antibodies, soluble receptor constructs, antisense strategies, RNA aptamers against VEGF and low molecular weight VEGF receptor tyrosine kinase (RTK) inhibitors have all been proposed for use in interfering with VEGF signaling. See, e.g., Siemeister et al. *Cancer Metastasis Rev.* 17:241-248

(1998). Anti-VEGF neutralizing antibodies have been shown to suppress the growth of a variety of human tumor cell lines in nude mice (Kim et al. *Nature* 362:841-844 (1993); Warren et al. *J. Clin. Invest.* 95:1789-1797 (1995); Borgström et al. *Cancer Res.* 56:4032-4039 (1996); and Melnyk et al. *Cancer Res.* 56:921-924 (1996)) and also inhibit intraocular angiogenesis in models of ischemic retinal disorders (Adamis et al. *Arch. Ophthalmol.* 114:66-71 (1996)). Indeed, a humanized anti-VEGF antibody, bevacizumab (AVASTIN®, Genentech) has been approved by the US FDA as a first-line therapy for metastic colorectal cancer. See, e.g., Ferrara et al., *Nature Reviews Drug Discovery*, 3:391-400 (2004).

However, current methods of cancer treatment are not always optimal. Often, a single type of therapy cannot completely suppress a pathological condition. For example, surgical procedures often cannot remove all the cancerous growth. Other cancer treatments, such as chemotherapy, have numerous side effects, and/or therapy becomes ineffective, e.g., because the cancer develops a resistance to the drug or treatment. Inhibition of VEGF or a VEGR receptor, or of the Tie2 receptor system sometimes did not completely suppress tumor growth. See, e.g., Gerber et al., *Cancer Research*, 60:6253-6258 (2000); Ferrara et al., *Nature Reviews: Drug Discovery*, 3:391-400 (2004); Millauer et al., *Nature* 367, 576-579 (1994); Kim et al., *Nature* 362: 841-844 (1993); Millauer et al., *Cancer Res.* 56:1615-1620 (1996); Goldman et al., *Proc. Natl. Acad. Sci. USA* 95:8795-8800 (1998); Asano et al., *Cancer Research*, 55:5296-5301 (1995); Warren et al., *J. Clin. Invest.*, 95:1789-1797 (1995); Fong et al., *Cancer Res.* 59:99-106 (1999); Wedge et al., *Cancer Res.* 60:970-975 (2000); Wood et al. *Cancer Res.* 60:2178-2189 (2000); Siemeister et al., *Cancer Res.* 59:3185-3191 (1999); Lin et al., *J. Clin. Invest.* 103:159-165 (1999); Lin et al., *Proc. Natl. Acad. Sci. USA* 95:8829-8834 (1998); and, Siemeister et al., *Cancer Res.* 59, 3185-3191, (1999).

Thus, there is an urgent need for new and more effective therapies for regulating cancers. The invention addresses these and other needs, as will be apparent upon review of the following disclosure.

SUMMARY OF THE INVENTION

The invention concerns inhibitors of angiopoietin-like 4 protein (ANGPTL4) and methods of using such inhibitors to treat diseases and pathological conditions, e.g., to block or reduce tumor growth or cancer cell growth, to block or reduce relapse tumor growth, etc. The invention provides combinations of inhibitors of ANGPTL4 and anti-cancer agents, and methods of using such combinations to inhibit tumor growth. The invention also provides combinations of inhibitors of ANGPTL4 and inhibitors of angiogenesis and methods of using such combinations to inhibit cancer growth and/or disorders involving angiogenesis, e.g., neoplastic (e.g., tumor growth) and non-neoplastic disorders.

Modulators of ANGPTL4, e.g., antagonists of ANGPTL4 or agonists, are provided. ANGPTL4 antagonists of the invention are molecules that inhibit or reduce the activity of ANGPTL4. An ANGPTL4 inhibitor can include a small molecular weight substance, an polynucleotide, antisense molecules, RNA aptamers, ribozymes against ANGPTL4 or its receptor polypeptides, an polypeptide, antagonist variants of ANGPTL4, an isolated protein, a recombinant protein, an antibody, or conjugates or fusion proteins thereof, that inhibits an ANGPTL4 activity, directly or indirectly. In certain embodiments, an antagonist of ANGPTL4 includes an antibody that binds ANGPTL4. In certain embodiments of the invention, an antagonist ANGPTL4 antibody is an antibody that inhibits or reduces the activity of ANGPTL4 by binding to a specific subsequence or region of the ANGPTL4 protein, e.g., N-terminal, N-terminal coiled-coil domain, C-terminal, C-terminal fibrinogen-like domain, or ANGPTL4 (1-183), ANGPTL4 (23-183), ANGPTL4 (1 to about 162), ANGPTL4 (about 162-406), ANGPTL4 (23-406), or ANGPTL4 (184-406) amino acid subsequence of human ANGPTL4, and/or mANGPTL4 (1-183), mANGPTL4 (23-183), mANGPTL4 (1 to about 165), mANGPTL4 (23 to about 165), mANGPTL4 (23-410) or mANGPTL4 (184-410) amino acid subsequence of the murine ANGPTL4. Other subsequences also include, but not limited to, e.g., 40-183, 60-183, 80-183, 100-183, 120-183, 140-183, 40-406, 60-406, 80-406, 100-406, 120-406, 140-406, and 160-406 of hANGPTL4 and, e.g., 40-183, 60-183, 80-183, 100-183, 120-183, 140-183, 40-410, 60-410, 80-410, 100-410, 120-410, 140-410 and 160-410 of mANGPTL4. In certain embodiments of the invention, an antagonist of ANGPTL4 includes an anti-$\alpha_v\beta_5$ antibody, e.g., an antagonist anti-$\alpha_v\beta_5$ antibody. In certain embodiments, the antibodies of the invention are humanized antibodies. In certain embodiments of the invention, an ANGPTL4 antagonist is a SiRNA molecule. In one embodiment, the SiRNA molecule is an ANGPTL4-SiRNA molecule, where the molecule targets a DNA sequence (e.g., GTGGCCAAGCCTGCCCGAAGA) of a nucleic acid encoding ANGPTL4.

Methods of blocking or reducing tumor growth or growth of a cancer cell are provided. In certain embodiments, the methods include administering to the tumor or cancer cell an effective amount of an angiopoietin-like 4 (ANGPTL4) antagonist. In another embodiment, the ANGPTL4 antagonist is an antagonist anti-$\alpha_v\beta_5$ antibody. The effective amount blocks or reduces tumor growth or growth of the cancer cell. Methods for inhibiting tumor cell migration are also provided. For example, a method includes administering an effective amount of an ANGPTL4 antagonist to tumor cells, thereby inhibiting their migration. In one embodiment of the invention, the administration of the ANGPTL4 antagonist inhibits metastasis.

Additional therapeutic agents, e.g., one or more anti-cancer agents, multiple antibodies to the same or different antigen, one or more anti-angiogenesis agents or inhibitors, pain medication, etc., can be combined and/or administered with an ANGPTL4 antagonist. Additional therapeutic procedures, e.g., surgical procedures, irradiation, etc., can also be performed or administered to the tumor and/or cancer cells in the methods or with compositions of the invention The invention also provides combination compositions, e.g., a composition which includes an anti-cancer agent (e.g., anti-angiogenesis agent, etc.), an ANGPTL4 antagonist, and a carrier (e.g., pharmaceutical acceptable carrier).

An anti-cancer agent includes, but is not limited to, e.g., anti-cancer agents known in the art and those described herein. In certain embodiments, an anti-cancer agent comprises one or more anti-angiogenesis agent, e.g., a VEGF antagonist or inhibitor, etc. In one embodiment, a VEGF antagonist comprises an anti-VEGF antibody or active fragment thereof (e.g., humanized A4.6.1, Avastin®, etc.). In certain embodiments, an anti-cancer agent comprises one or more chemotherapeutic agents.

Combination methods of blocking or reducing tumor growth or growth of a cancer cell are provided. In certain embodiments, the methods include administering to the tumor or the cancer cell an effective amount of an anti-cancer agent, and administering to the tumor or the cancer cell an effective amount of an ANGPTL4 antagonist. Alternatively, or additionally, a combination composition comprising an effective amount of anti-cancer agent (e.g., anti-angiogenesis agent, etc.) and an effective amount of an ANGPTL4 antagonist can be administered. The combined effective amounts block or reduce tumor growth or growth of the cancer cell.

Methods of blocking or reducing relapse tumor growth or a relapse cancer cell growth are also provided. In certain embodiments of the invention, the subject was, or is concurrently undergoing cancer therapy with at least one anti-cancer agent, and the subject is administered an effective amount of an ANGPTL4 antagonist. The administration of the effective amount of the ANGPTL4 antagonist blocks or reduces the relapse tumor growth or relapse cancer cell growth. In certain embodiments, the subject was, or is concurrently undergoing therapy with an ANGPTL4 antagonist, and the subject is administered an effective amount of an anti-cancer agent (e.g., an anti-angiogenesis agent), where the administration of the effective amount of the anti-cancer agent blocks or reduces the relapse tumor growth or relapse cancer cell growth.

Typically, the tumor or the cancer cell is in a subject. In certain embodiments, the subject was, is concurrently or will be undergoing cancer therapy with at least one anti-cancer agent. Typically, the subject is a mammal (e.g., a human). In certain embodiments, the agents of the invention are administered to a subject. The administration or procedure steps can be performed in any order. In one embodiment, they are performed sequentially. In another embodiment, they are performed concurrently. Alternatively, or additionally, the steps can be performed as a combination of both sequentially and concurrently, in any order.

Kits of ANGPTL4 modulators are also provided. In certain embodiments, a kit includes an ANGPTL4 antagonist, a pharmaceutically acceptable carrier, vehicle, or diluent, and a container. In one embodiment, a kit includes a first amount of an anti-cancer agent (e.g., an anti-angiogenesis agent, etc.), a second amount of an ANGPTL4 antagonist and a pharmaceutically acceptable carrier, vehicle, or diluent, and a container. In another embodiment, a kit includes an amount of an anti-cancer agent (e.g., an anti-angiogenesis agent, etc.) and a pharmaceutically acceptable carrier, vehicle, or diluent in a first unit dosage form; an amount of an ANGPTL4 antagonist and a pharmaceutically acceptable carrier, vehicle, or diluent in a second unit dosage form; and a container. Instructions for their use can also be included.

BRIEF DESCRIPTION OF THE FIGURES

FIG. 1 illustrates a nucleic acid sequence of human ANGPTL4 (SEQ ID NO. 1).

FIG. 2 illustrates an amino acid sequence of human ANGPTL4 (SEQ ID NO. 2).

FIG. 3, Panel A illustrates purified recombinant murine ANGPTL4 (23-410) separated on SDS polyacrylamide gel electrophoresis (SDS-PAGE) (4-20%) in the presence (10 mM) or absence of dithiothreitol (DTT). FIG. 3, Panel B illustrates wild type (lane 1) and variant hANGPTL4 (lane 2) separated on a SDS gel and detected by western blotting, where the variant hANGPTL4 has a R162G and R164E substitution.

FIG. 4, Panels A, B, and C schematically illustrate that ANGPTL4 stimulates A673 tumor cell (Panel A and B) and U87MG tumor cell (Panel B) proliferation by transduction of tumor cells with an ANGPTL4 expression construct, and by conditioned media from COS cells (C) transduced with an ANGPTL4 expression construct (2) (Panel C). In Panel B, tumor cells are transduced with either (1) which is AdLacZ expression construct control, (2) which is Ad-ANGPTL4 expression construct or (3) which is Ad-SiRNA ANGPTL4 construct. In Panel C, A673 tumor cell proliferation is performed by conditioned media from Hepa (A), HMVEC (B) or COS cells (C) tranduced with either (1) a LacZ expression construct, (2) an ANGPTL4 expression construct or (3) an ANGPTL3 expression construct.

FIG. 5 schematically illustrates that mANGPTL4 stimulates A673 proliferation when coated onto culture dishes.

FIG. 6, Panels A and B schematically illustrate various forms (Panel A) of ANGPTL4 binding to A673 tumor cells and under various conditions (Panel B).

FIG. 7, Panels A and B schematically illustrate A673 proliferation with media containing ANGPTL4 when grown for 7 days (Panel A) or 4 days (Panel B). In Panel A, (1) is an AdLacZ expression construct control, (2) is an Ad-hANGPTL4 expression construct, and, (3) is an AdLacZ expression construct and rmANGPTL4. In Panel B, (1) is nothing added, (2) is a buffer control, (3) mANGPTL4 (2.5 µg/ml), (4) is hANGPTL4 (2.5 µg/ml), (5) is hIgG-hANGPTL4 (2.5 µg/ml) and (6) hIgG-mANGPTL4 (2.5 µg/ml).

FIG. 8, Panels A, B and C schematically illustrate ANGPTL4 promotes tumor growth in vivo (Panel A and Panel B) and the trend to escape from anti-tumor treatment, e.g., with an anti-VEGF antibody (AVASTIN® (Genentech, South San Francisco)), in tumors with intratumoral administration of adenovirus-Angptl4 constructs (Panel C). Panels A and C illustrate tumor size in $cm^3$ verses days post tumor implantation. Panel B illustrates xenografted A673 tumor weight 20 days after implantation.

FIG. 9 illustrates ANGPTL4 induces cell migration of tumor cells, A673 and 4T-1, where (1) is no serum added, (2) is 10% fetal calf serum (FCS), (3) is PDGF-BB, and (4) ANGPTL4.

FIG. 10, Panels A and B illustrate that anti-hANGPTL4 antibodies inhibits tumor cell growth, e.g., Panel A (HeLa-S3 and Caki cells) and Panel B (U87MG, 293 and A673 cells), where (1) is anti-hANGPTL4 antibodies, (2) is anti-down syndrome critical region 1 protein (Dscr) antibody control, and (3) is nothing added, where the numbers below the bar graph indicated the antibody concentration in (µg/ml).

FIG. 11 illustrate the adhesion of 293-1953 ($\alpha_v\beta_5$) cells to a plate coated with either ANGPTL4 or vitronectin at the concentration indicated at the bottom in (µg/ml), where BSA is used as a control.

FIG. 12 illustrates that anti-$\alpha_v\beta_5$ and anti-hANGPTL4 antibodies abolish ANGPTL4 cell adhesion activity, where (1) is BSA, (2) is vitronectin, and (3) is ANGPTL4.

FIG. 13, Panels A, B and C illustrate binding of ANGPTL4 to integrin $\alpha_v\beta_5$. Panel A illustrates binding of protein (mANGPTL4, hANGPTL4-$N_{terminal}$, or hANGPTL4-$C_{terminal}$) using the amount indicated to $\alpha_v\beta_5$ coated plates. Panel B illustrates inhibition of binding of protein (mANGPTL4, hANGPTL4-$N_{terminal}$, or hANGPTL4-$C_{terminal}$) to a" coated plates with anti-hANGPTL4 antibodies. Panel C illustrates binding of ANGPTL4 and $\alpha_v\beta_5$, where (1) is hANGPTL4-Cterminal coated on the plate, (2) is hANGPTL4-Cterminal coated on plate and incubated with anti-hANGPTL4, (3) is hANGPTL4-Cterminal coated on the plate and incubated anti-Dscr, (4) is Vitronectin coated on the plate and (5) is BSA coated on the plate, before adding $\alpha_v\beta_5$.

DETAILED DESCRIPTION

Definitions

Before describing the invention in detail, it is to be understood that this invention is not limited to particular compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a molecule" optionally includes a combination of two or more such molecules, and the like.

Unless defined otherwise, all scientific and technical terms are understood to have the same meaning as commonly used in the art to which they pertain. For the purpose of the invention, the following terms are defined below.

The term "ANGPTL4 or "Angptl4" refers to angiopoietin-like 4 polypeptide or protein, along with naturally occurring allelic, secreted, and processed forms thereof. For example, ANGPTL4 from human is a 406 amino acid protein, while the mouse ANGPTL4 is a 410 amino acid protein. The term "ANGPTL4" is also used to refer to fragments (e.g., subsequences, truncated forms, etc.) of the polypeptide comprising, e.g., N-terminal fragment, Coiled-coil domain, C-terminal fragment, fibrinogen-like domain, amino acids 1-183, 23-183, 1 to about 162, 23 to about 162, 23-406, 184-406, about 162-406, or 23-184 of the human angiopoietin-like 4 protein, and amino acids 1-183, 23-183, 1 to about 165, 23 to about 165, 23-410, or 184-410 of the murine angiopoietin-like 4 protein. Other fragments include, but are not limited to, e.g., 40-183, 60-183, 80-183, 100-183, 120-183, 140-183, 40-406, 60-406, 80-406, 100-406, 120-406, 140-406, and 160-406 of hANGPTL4 and, e.g., 40-183, 60-183, 80-183, 100-183, 120-183, 140-183, 40-410, 60-410, 80-410, 100-410, 120-410, 140-410 and 160-410 of mANGPTL4. Reference to any such forms of ANGPTL4 can also be identified in the application, e.g., by "ANGPTL4 (23-406)," "ANGPTL4 (184-406)," "ANGPTL4 (23-183)," "mANGPTL4 (23-410)," "mANGPTL4 (184-410)," etc., where m indicates murine sequence. The amino acid position for a fragment native ANGPTL4 are numbered as indicated in the native ANGPTL4 sequence. For example, amino acid position 22(Ser) in a fragment ANGPTL4 is also position 22(Ser) in native human ANGPTL4, e.g., see FIG. 2. Generally, the fragment native ANGPTL4 has biological activity.

The term "ANGPTL4 modulator" refers to a molecule that can activate, e.g., an agonist, ANGPTL4 or its expression, or that can inhibit, e.g., an antagonist (or inhibitor), the activity of ANGPTL4 or its expression. ANGPTL4 agonists include antibodies and active fragments. An ANGPTL4 antagonist refers to a molecule capable of neutralizing, blocking, inhibiting, abrogating, reducing or interfering with ANGPTL4 activities, e.g., cell proliferation or growth, migration, adhesion or metabolic, e.g., lipid, modulation, or its expression including its binding to an ANGPTL4 receptor, e.g., $\alpha_v\beta_5$. ANGPTL4 antagonists include, e.g., anti-ANGPTL4 antibodies and antigen-binding fragments thereof, receptor molecules and derivatives which bind specifically to ANGPTL4 thereby sequestering its binding to one or more receptors, anti-ANGPTL4 receptor antibodies and ANGPTL4 receptor antagonists such as small molecule inhibitors of the receptor. Other ANGPTL4 antagonists also include antagonist variants of ANGPTL4, antisense molecules (e.g., ANGPTL4-SiRNA), RNA aptamers, and ribozymes against ANGPTL4 or its receptor. In certain embodiments, antagonist ANGPTL4 antibodies are antibodies that inhibit or reduce the activity of ANGPTL4 by binding to a specific subsequence or region of ANGPTL4, e.g., N-terminal fragment, Coiled-coil domain, C-terminal fragment, fibrinogen-like domain, amino acids 1-183, 23-183, 1 to about 162, 23 to about 162, 23-406, 184-406, or 23-184 of the human angiopoietin-like 4 protein, and amino acids 1-183, 23-183, 1 to about 165, 23 to about 165, 23-410, or 184-410 of the murine angiopoietin-like 4 protein. Other fragments include, but are not limited to, e.g., 40-183, 60-183, 80-183, 100-183, 120-183, 140-183, 40-406, 60-406, 80-406, 100-406, 120-406, 140-406, and 160-406 of hANGPTL4 and, e.g., 40-183, 60-183, 80-183, 100-183, 120-183, 140-183, 40-410, 60-410, 80-410, 100-410, 120-410, 140-410 and 160-410 of mANGPTL4.

The term "Anti-ANGPTL4 antibody" is an antibody that binds to ANGPTL4 with sufficient affinity and specificity. The anti-ANGPTL4 antibody of the invention can be used as a therapeutic agent in targeting and interfering with diseases or conditions wherein ANGPTL4 activity is involved. Generally, an anti-ANGPTL4 antibody will usually not bind to other ANGPTL4 homologues, e.g., ANGPTL3.

The terms "VEGF" and "VEGF-A" are used interchangeably to refer to the 165-amino acid vascular endothelial cell growth factor and related 121-, 145-, 183-, 189-, and 206-amino acid vascular endothelial cell growth factors, as described by Leung et al. *Science,* 246:1306 (1989), Houck et al. *Mol. Endocrin.,* 5:1806 (1991), and, Robinson & Stringer, *Journal of Cell Science,* 144(5):853-865 (2001), together with the naturally occurring allelic and processed forms thereof. The term "VEGF" is also used to refer to fragments of the polypeptide, e.g., comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)" or "VEGF165." The amino acid positions for a "fragment" native VEGF are numbered as indicated in the native VEGF sequence. For example, amino acid position 17 (methionine) in fragment native VEGF is also position 17 (methionine) in native VEGF. The fragment native VEGF can have binding affinity for the KDR and/or Flt-1 receptors comparable to native VEGF.

An "anti-VEGF antibody" is an antibody that binds to VEGF with sufficient affinity and specificity. The anti-VEGF antibody of the invention can be used as a therapeutic agent in targeting and interfering with diseases or conditions wherein the VEGF activity is involved. An anti-VEGF antibody will usually not bind to other VEGF homologues such as VEGF-B or VEGF-C, nor other growth factors such as PlGF, PDGF or bFGF. See, e.g., U.S. Pat. Nos. 6,582,959, 6,703,020; WO98/45332; WO 96/30046; WO94/10202; EP 0666868B1; US Patent Applications 20030206899, 20030190317, 20030203409, and 20050112126; Popkov et al., *Journal of Immunological Methods* 288:149-164 (2004); and PCT/US04/24662. The anti-VEGF antibody "Bevacizumab (By)", also known as "rhuMAb VEGF" or "Avastin™", is a recombinant humanized anti-VEGF monoclonal antibody generated according to Presta et al. *Cancer Res.* 57:4593-4599 (1997). It comprises mutated human IgG1 framework regions and antigen-binding complementarity-determining regions from the murine anti-h VEGF monoclonal antibody A.4.6.1 that blocks binding of human VEGF to its receptors. Approximately 93% of the amino acid sequence of Bevacizumab, including most of the framework regions, is derived from human IgG1, and about 7% of the sequence is derived from the murine antibody A4.6.1. Bevacizumab has a molecular mass of about 149,000 daltons and is glycosylated. Bevacizumab and other humanized anti-VEGF antibodies are further described in U.S. Pat. No. 6,884,879 issued Feb. 26, 2005.

A "VEGF antagonist" refers to a molecule capable of neutralizing, blocking, inhibiting, abrogating, reducing or interfering with VEGF activities including its binding to one or more VEGF receptors. VEGF antagonists include anti-VEGF antibodies and antigen-binding fragments thereof, receptor molecules and derivatives which bind specifically to VEGF thereby sequestering its binding to one or more receptors, anti-VEGF receptor antibodies and VEGF receptor antagonists such as small molecule inhibitors of the VEGFR tyrosine kinases, and fusions proteins, e.g., VEGF-Trap (Regeneron), $VEGF_{121}$-gelonin (Peregine). VEGF antagonists also include antagonist variants of VEGF, antisense molecules directed to VEGF, RNA aptamers, and ribozymes against VEGF or VEGF receptors.

A "native sequence" polypeptide comprises a polypeptide having the same amino acid sequence as a polypeptide derived from nature. Thus, a native sequence polypeptide can have the amino acid sequence of naturally occurring polypeptide from any mammal. Such native sequence polypeptide can be isolated from nature or can be produced by recombinant or synthetic means. The term "native sequence" polypeptide specifically encompasses naturally occurring truncated or secreted forms of the polypeptide (e.g., an extracellular domain sequence), naturally occurring variant forms (e.g., alternatively spliced forms) and naturally occurring allelic variants of the polypeptide.

A "polypeptide chain" is a polypeptide wherein each of the domains thereof is joined to other domain(s) by peptide bond(s), as opposed to non-covalent interactions or disulfide bonds.

A polypeptide "variant" means a biologically active polypeptide having at least about 80% amino acid sequence identity with the corresponding native sequence polypeptide. Such variants include, for instance, polypeptides wherein one or more amino acid (naturally occurring amino acid and/or a non-naturally occurring amino acid) residues are added, or deleted, at the N- and/or C-terminus of the polypeptide. Ordinarily, a variant will have at least about 80% amino acid sequence identity, or at least about 90% amino acid sequence identity, or at least about 95% or more amino acid sequence identity with the native sequence polypeptide. Variants also include polypeptide fragments (e.g., subsequences, truncations, etc.), typically biologically active, of the native sequence.

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, e.g., digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

The term "ANGPTL4 variant" as used herein refers to a variant as described above and/or an ANGPTL4 which includes one or more amino acid mutations in the native ANGPTL4 sequence. Optionally, the one or more amino acid mutations include amino acid substitution(s). ANGPTL4 and variants thereof for use in the invention can be prepared by a variety of methods well known in the art. Amino acid sequence variants of ANGPTL4 can be prepared by mutations in the ANGPTL4 DNA. Such variants include, for example, deletions from, insertions into or substitutions of residues within the amino acid sequence of ANGPTL4, e.g., a human amino acid sequence encoded by the nucleic acid deposited under ATCC deposit number 209284, or as shown in FIG. 2. Any combination of deletion, insertion, and substitution may be made to arrive at the final construct having the desired activity. The mutations that will be made in the DNA encoding the variant must not place the sequence out of reading frame and preferably will not create complementary regions that could produce secondary mRNA structure. EP 75,444A.

The ANGPTL4 variants optionally are prepared by site-directed mutagenesis of nucleotides in the DNA encoding the native ANGPTL4 or phage display techniques, thereby producing DNA encoding the variant, and thereafter expressing the DNA in recombinant cell culture.

While the site for introducing an amino acid sequence variation is predetermined, the mutation per se need not be predetermined. For example, to optimize the performance of a mutation at a given site, random mutagenesis may be conducted at the target codon or region and the expressed ANGPTL4 variants screened for the optimal combination of desired activity. Techniques for making substitution mutations at predetermined sites in DNA having a known sequence are well-known, such as, for example, site-specific mutagenesis. Preparation of the ANGPTL4 variants described herein can be achieved by phage display techniques, such as those described in the PCT publication WO 00/63380.

After such a clone is selected, the mutated protein region may be removed and placed in an appropriate vector for protein production, generally an expression vector of the type that may be employed for transformation of an appropriate host.

Amino acid sequence deletions generally range from about 1 to 30 residues, optionally 1 to 10 residues, optionally 1 to 5 residues or less, and typically are contiguous.

Amino acid sequence insertions include amino- and/or carboxyl-terminal fusions of from one residue to polypeptides of essentially unrestricted length as well as intrasequence insertions of single or multiple amino acid residues.

Intrasequence insertions (i.e., insertions within the native ANGPTL4 sequence) may range generally from about 1 to 10 residues, optionally 1 to 5, or optionally 1 to 3. An example of a terminal insertion includes a fusion of a signal sequence, whether heterologous or homologous to the host cell, to the N-terminus to facilitate the secretion from recombinant hosts.

Additional ANGPTL4 variants are those in which at least one amino acid residue in the native ANGPTL4 has been removed and a different residue inserted in its place. In one embodiment of the invention, ANGPTL4 variant includes a substitution at 162 and/or 164 of ANGPTL4 or a substitution at 169 of mANGPTL4. Such substitutions may be made in accordance with those shown in Table 1. ANGPTL4 variants can also unnatural amino acids as described herein.

Amino acids may be grouped according to similarities in the properties of their side chains (in A. L. Lehninger, in *Biochemistry*, second ed., pp. 73-75, Worth Publishers, New York (1975)):
(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp. Tyr, Phe.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

"Naturally occurring amino acid residues" (i.e. amino acid residues encoded by the genetic code) may be selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile); leucine (Leu); lysine (Lys); methionine (Met); phenylalanine (Phe); proline (Pro); serine (Ser); threonine (Thr); tryptophan (Trp); tyrosine (Tyr); and valine (Val). A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include, e.g., norleucine, ornithine, norvaline, homoserine and other amino acid residue analogues such as those described in Ellman et al. *Meth. Enzym.* 202:301-336 (1991) & US Patent application publications 20030108885 and 20030082575. Briefly, these procedures involve activating a suppressor tRNA with a non-naturally occurring amino acid residue followed by in vitro or in vivo transcription and translation of the RNA. See, e.g., US Patent application publications 20030108885 and 20030082575; Noren et al. Science 244:182 (1989); and, Ellman et al., supra.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In certain embodiments, the polypeptide will be purified (1) to greater than 95% by weight of polypeptide as determined by the Lowry method, or more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue, or silver stain. Isolated polypeptide includes the polypeptide in situ within recombinant cells since at least one component of the polypeptide's natural environment will not be present. Ordinarily, however, isolated polypeptide will be prepared by at least one purification step.

The term "antibody" is used in the broadest sense and includes monoclonal antibodies (including full length or intact monoclonal antibodies), polyclonal antibodies, multivalent antibodies, multispecific antibodies (e.g., bispecific antibodies), and antibody fragments (see below) so long as they exhibit the desired biological activity.

Unless indicated otherwise, the expression "multivalent antibody" is used throughout this specification to denote an antibody comprising three or more antigen binding sites. The multivalent antibody is typically engineered to have the three or more antigen binding sites and is generally not a native sequence IgM or IgA antibody.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., *Nature* 341, 544-546 (1989)) which consists of a VH domain; (vii) isolated CDR regions; (viii) F(ab')2 fragments, a bivalent fragment including two Fab' fragments linked by a disulphide bridge at the hinge region; (ix) single chain antibody molecules (e.g. single chain Fv; scFv) (Bird et al., *Science* 242:423-426 (1988); and Huston et al., *PNAS* (USA) 85:5879-5883 (1988)); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., *Proc. Natl. Acad. Sci. USA*, 90:6444-6448 (1993)); (xi) "linear antibodies" comprising a pair of tandem Fd segments (VH-CH1-VH-CH1) which, together with complementary light chain polypeptides, form a pair of antigen binding regions (Zapata et al. *Protein Eng.* 8(10):1057 1062 (1995); and U.S. Pat. No. 5,641,870).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. For example, the monoclonal antibodies to be used in accordance with the invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) or Marks et al., *J. Mol. Biol.* 222:581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are, not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies (Vaughan et al. *Nature Biotechnology* 14:309-314 (1996): Sheets et al. *PNAS (USA)* 95:6157-6162 (1998)); Hoogenboom and Winter, *J. Mol. Biol.* 227:381 (1991); Marks et al., *J. Mol. Biol.*, 222:581 (1991)). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10: 779-783 (1992); Lonberg et al., *Nature* 368: 856-859 (1994); Morrison, *Nature* 368:812-13 (1994); Fishwild et al., *Nature Biotechnology* 14: 845-51 (1996); Neuberger, *Nature Biotechnology* 14: 826 (1996); Lonberg and Huszar, *Intern. Rev. Immunol.* 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., *Monoclonal Antibodies and Cancer Therapy*, Alan R. Liss, p. 77 (1985); Boerner et al., *J. Immunol.*, 147 (1):86-95 (1991); and U.S. Pat. No. 5,750,373.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest, 5th Ed.* Public Health Service, National Institutes of Health, Bethesda, Md. (1991)). The constant domains are not involved directly in binding an antibody to an antigen, but exhibit various effector functions, such as participation of the antibody in antibody-dependent cell-mediated cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR"

residues are those variable domain residues other than the hypervariable region residues as herein defined.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into "subclasses" (isotypes), e.g. $IgG_1$ (including non-A and A allotypes), $IgG_2$, $IgG_3$, $IgG_4$, IgA, and $IgA_2$. The heavy-chain constant domains that correspond to the different classes of antibodies are called α, δ, ε, γ and μ, respectively. The subunit structures and three-dimensional configurations of different classes of immunoglobulins are well known.

The light chains of antibodies from any vertebrate species can be assigned to one of two clearly distinct types, called kappa (6) and lambda (8), based on the amino acid sequences of their constant domains.

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The Fc region of an immunoglobulin generally comprises two constant domains, a CH2 domain and a CH3 domain, and optionally comprises a CH4 domain.

By "Fc region chain" herein is meant one of the two polypeptide chains of an Fc region.

The "CH2 domain" of a human IgG Fc region (also referred to as "Cg2" domain) usually extends from an amino acid residue at about position 231 to an amino acid residue at about position 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec. Immunol.* 22:161-206 (1985). The CH2 domain herein may be a native sequence CH2 domain or variant CH2 domain.

The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protroberance" in one chain thereof and a corresponding introduced "cavity" in the other chain thereof; see U.S. Pat. No. 5,821,333, expressly incorporated herein by reference). Such variant CH3 domains may be used to make multispecific (e.g. bispecific) antibodies as herein described.

"Hinge region" is generally defined as stretching from about Glu216, or about Cys226, to about Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions. The hinge region herein may be a native sequence hinge region or a variant hinge region. The two polypeptide chains of a variant hinge region generally retain at least one cysteine residue per polypeptide chain, so that the two polypeptide chains of the variant hinge region can form a disulfide bond between the two chains. The preferred hinge region herein is a native sequence human hinge region, e.g. a native sequence human IgG1 hinge region.

A "functional Fc region" possesses at least one "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature.

A "variant Fc region" comprises an amino acid sequence which differs from that of a native sequence Fc region by virtue of at least one amino acid modification. In certain embodiments, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will typically possess, e.g., at least about 80% sequence identity with a native sequence Fc region and/or with an Fc region of a parent polypeptide, or at least about 90% sequence identity therewith, or at least about 95% sequence or more identity therewith.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Human effector cells" are leukocytes which express one or more FcRs and perform effector functions. Typically, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being generally preferred. The effector cells may be isolated from a native source thereof, e.g. from blood or PBMCs as described herein.

The terms "Fc receptor" and "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976); and Kim et al., *J. Immunol.* 24:249 (1994)).

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

An "affinity matured" antibody is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "flexible linker" herein refers to a peptide comprising two or more amino acid residues joined by peptide bond(s), and provides more rotational freedom for two polypeptides (such as two Fd regions) linked thereby. Such rotational freedom allows two or more antigen binding sites joined by the flexible linker to each access target antigen(s) more efficiently. Examples of suitable flexible linker peptide sequences include gly-ser, gly-ser-gly-ser, ala-ser, and gly-gly-gly-ser.

A "dimerization domain" is formed by the association of at least two amino acid residues (generally cysteine residues) or of at least two peptides or polypeptides (which may have the same, or different, amino acid sequences). The peptides or polypeptides may interact with each other through covalent and/or non-covalent association(s). Examples of dimerization domains herein include an Fc region; a hinge region; a CH3 domain; a CH4 domain; a CH1-CL pair; an "interface" with an engineered "knob" and/or "protruberance" as described in U.S. Pat. No. 5,821,333, expressly incorporated herein by reference; a leucine zipper (e.g. a jun/fos leucine zipper, see Kostelney et al., *J. Immunol.,* 148: 1547-1553 (1992); or a yeast GCN4 leucine zipper); an isoleucine zipper; a receptor dimer pair (e.g., interleukin-8 receptor (IL-8R); and integrin heterodimers such as LFA-1 and GPIIIb/IIIa), or the dimerization region(s) thereof; dimeric ligand polypeptides (e.g. nerve growth factor (NGF); neurotrophin-3 (NT-3), interleukin-8 (IL-8), vascular endothelial growth factor (VEGF), VEGF-C, VEGF-D, PDGF members, and brain-derived neurotrophic factor (BDNF); see Arakawa et al. *J. Biol. Chem.* 269(45): 27833-27839 (1994) and Radziejewski et al. *Biochem.* 32(48): 1350 (1993)), or the dimerization region(s) thereof; a pair of cysteine residues able to form a disulfide bond; a pair of peptides or polypeptides, each comprising at least one cysteine residue (e.g. from about one, two or three to about ten cysteine residues) such that disulfide bond(s) can form between the peptides or polypeptides (hereinafter "a synthetic hinge"); and antibody variable domains. The most preferred dimerization domain herein is an Fc region or a hinge region.

A "functional antigen binding site" of an antibody is one which is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same. For the multimeric antibodies herein, the number of functional antigen binding sites can be evaluated using ultracentrifugation analysis. According to this method of analysis, different ratios of target antigen to multimeric antibody are combined and the average molecular weight of the complexes is calculated assuming differing numbers of functional binding sites. These theoretical values are compared to the actual experimental values obtained in order to evaluate the number of functional binding sites.

An antibody having a "biological characteristic" of a designated antibody is one which possesses one or more of the biological characteristics of that antibody which distinguish it from other antibodies that bind to the same antigen.

In order to screen for antibodies which bind to an epitope on an antigen bound by an antibody of interest, a routine cross-blocking assay such as that described in *Antibodies, A Laboratory Manual*, Cold Spring Harbor Laboratory, Ed Harlow and David Lane (1988), can be performed.

Administration "in combination with" one or more further therapeutic agents includes simultaneous (concurrent) and/or consecutive administration in any order.

"Mammal" for purposes of treatment refers to any animal classified as a mammal, including humans, domestic and farm animals, and zoo, sports, or pet animals, such as dogs, horses, cats, cows, sheep, pigs, etc. Typically, the mammal is a human.

A "disorder" is any condition that would benefit from treatment with the molecules of the invention. This includes chronic and acute disorders or diseases including those pathological conditions which predispose the mammal to the disorder in question. Non-limiting examples of disorders to be treated herein include any form of tumor, benign and malignant tumors; vascularized tumors; hypertrophy; leukemias and lymphoid malignancies; neuronal, glial, astrocytal, hypothalamic and other glandular, macrophagal, epithelial, stromal and blastocoelic disorders; and inflammatory, angiogenic and immunologic disorders, vascular disorders that result from the inappropriate, aberrant, excessive and/or pathological vascularization and/or vascular permeability.

The term "effective amount" or "therapeutically effective amount" refers to an amount of a drug effective to treat a disease or disorder in a mammal. In the case of cancer, the effective amount of the drug may reduce the number of cancer cells; reduce the tumor size; inhibit (i.e., slow to some extent and typically stop) cancer cell infiltration into peripheral organs; inhibit (i.e., slow to some extent and typically stop) tumor metastasis; inhibit, to some extent, tumor growth; and/ or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

"Treatment" refers to both therapeutic treatment and prophylactic or preventative measures. Those in need of treatment include those already with the disorder as well as those in which the disorder is to be prevented.

The term "biological activity" and "biologically active" with regard to ANGPTL4 molecules herein refer to the ability of a molecule to specifically bind to and regulate cellular responses, e.g., proliferation, adhesion, migration, lipid modulation, etc. Cellular responses also include those mediated through an ANGPTL4 receptor, e.g., an $\alpha_v\beta_5$ integrin receptor, including, but not limited to, adhesion, migration, and/or proliferation. In this context, the term "modulate" includes both promotion and inhibition. Molecules of the invention also include agonists and antagonists of an ANGPTL4 receptor, e.g., $\alpha_v\beta_5$ integrin receptor.

"Hypertrophy", as used herein, is defined as an increase in mass of an organ or structure independent of natural growth that does not involve tumor formation. Hypertrophy of an organ or tissue is due either to an increase in the mass of the individual cells (true hypertrophy), or to an increase in the number of cells making up the tissue (hyperplasia), or both.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include kidney or renal cancer, breast cancer, colon cancer, rectal cancer, colorectal cancer, lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, liver cancer, bladder cancer, cancer of the peritoneum, hepatocellular cancer, gastric or stomach cancer including gastrointestinal cancer, pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, urinary tract carcinomas, thyroid carcinomas, Wilm's tumor, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

The term "anti-neoplastic composition" refers to a composition useful in treating cancer comprising at least one active therapeutic agent, e.g., "anti-cancer agent." Examples of therapeutic agents (anti-cancer agents) include, but are limited to, e.g., chemotherapeutic agents, growth inhibitory agents, cytotoxic agents, agents used in radiation therapy, anti-angiogenesis agents, apoptotic agents, anti-tubulin agents, toxins, and other-agents to treat cancer, e.g., anti-VEGF neutralizing antibody, VEGF antagonist, anti-HER-2, anti-CD20, an epidermal growth factor receptor (EGFR) antagonist (e.g., a tyrosine kinase inhibitor), HER1/EGFR inhibitor, erlotinib, a COX-2 inhibitor (e.g., celecoxib), interferons, cytokines, antagonists (e.g., neutralizing antibodies) that bind to one or more of the ErbB2, ErbB3, ErbB4, or VEGF receptor(s), inhibitors for receptor tyrosine kinases for platet-derived growth factor (PDGF) and/or stem cell factor (SCF) (e.g., imatinib mesylate (Gleevec® Novartis)), TRAIL/Apo2, and other bioactive and organic chemical agents, etc. Combinations thereof are also included in the invention.

The term "cytotoxic agent" as used herein refers to a substance that inhibits or prevents the function of cells and/or causes destruction of cells. The term is intended to include radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$P and radioactive isotopes of Lu), chemotherapeutic agents, and toxins such as small molecule toxins or enzymatically active toxins of bacterial, fungal, plant or animal origin, including fragments and/or variants thereof.

A "growth inhibitory agent" when used herein refers to a compound or composition which inhibits growth of a cell in vitro and/or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); lapatinib ditosylate (an ErbB-2 and EGFR dual tyrosine kinase small-molecule inhibitor also known as GW572016); COX-2 inhibitors such as celecoxib (CELEBREX®; 4-(5-(4-methylphenyl)-3-(trifluoromethyl)-1H-pyrazol-1-yl)benzenesulfonamide; and pharmaceutically acceptable salts, acids or derivatives of any of the above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factors (e.g., VEGF, VEGF-B, VEGF-C, VEGF-D, VEGF-E); placental derived growth factor (PIGF); platelet derived growth factors (PDGF, e.g., PDGFA, PDGFB, PDGFC, PDGFD); integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO);

osteoinductive factors; interferons such as interferon-alpha, -beta and -gamma, colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1 alpha, IL-1 beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20-IL-30; secretoglobin/uteroglobin; oncostatin M (OSM); a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

An "angiogenic factor or agent" is a growth factor which stimulates the development of blood vessels, e.g., promotes angiogenesis, endothelial cell growth, stability of blood vessels, and/or vasculogenesis, etc. For example, angiogenic factors, include, but are not limited to, e.g., VEGF and members of the VEGF family, PlGF, PDGF family, fibroblast growth factor family (FGFs), TIE ligands (Angiopoietins), ephrins, ANGPTL3, ANGPTL4, etc. It would also include factors that accelerate wound healing, such as growth hormone, insulin-like growth factor-I (IGF-I), VIGF, epidermal growth factor (EGF), CTGF and members of its family, and TGF-α and TGF-β. See, e.g., Klagsbrun and D'Amore, *Annu. Rev. Physiol.,* 53:217-39 (1991); Streit and Detmar, *Oncogene,* 22:3172-3179 (2003); Ferrara & Alitalo, *Nature Medicine* 5(12):1359-1364 (1999); Tonini et al., *Oncogene,* 22:6549-6556 (2003) (e.g., Table 1 listing angiogenic factors); and, Sato *Int. J. Clin. Oncol.,* 8:200-206 (2003).

An "anti-angiogenesis agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. For example, an anti-angiogenesis agent is an antibody or other antagonist to an angiogenic agent as defined above, e.g., antibodies to VEGF, antibodies to VEGF receptors, small molecules that block VEGF receptor signaling (e.g., PTK787/ZK2284, SU6668). Anti-angiogensis agents also include native angiogenesis inhibitors, e.g., angiostatin, endostatin, etc. See, e.g., Klagsbrun and D'Amore, *Annu. Rev. Physiol.,* 53:217-39 (1991); Streit and Detmar, Oncogene, 22:3172-3179 (2003) (e.g., Table 3 listing anti-angiogenic therapy in malignant melanoma); Ferrara & Alitalo, *Nature Medicine* 5(12):1359-1364 (1999); Tonini et al., *Oncogene,* 22:6549-6556 (2003) (e.g., Table 2 listing antiangiogenic factors); and, Sato *Int. J. Clin. Oncol.,* 8:200-206 (2003) (e.g., Table 1 lists Anti-angiogenic agents used in clinical trials).

The word "label" when used herein refers to a detectable compound or composition which is conjugated directly or indirectly to the polypeptide. The label may be itself be detectable (e.g., radioisotope labels or fluorescent labels) or, in the case of an enzymatic label, may catalyze chemical alteration of a substrate compound or composition which is detectable.

An "isolated" nucleic acid molecule is a nucleic acid molecule that is identified and separated from at least one contaminant nucleic acid molecule with which it is ordinarily associated in the natural source of the polypeptide nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the polypeptide where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

ANGPTL4

Angiopoietin-like 4 protein (ANGPTL4) is a secreted protein and is a member of the angiopoietin family. It is also known as hepatic fibrinogen/angiopoietin-related protein (HFARP) (Kim et al., *Biochem. J.* 346:603-610 (2000)), PGAR (PPARγ angiopoietin related protein) (Yoon, et al., *Mol. Cell Biol.,* 20:5343-5349 (2000)), fasting induced adipose factor (FIAF) (Kerten et al., *J. Biol. Chem.,* 275:28488-

28493 (2000)); angiopoietin-related protein (ARP-4); NL2 (see U.S. Pat. Nos. 6,348,350; 6,372,491; and 6,455,496); and Ang6.

The ANGPTL4 protein from human is a 406 amino acid protein (e.g., U.S. Pat. Nos. 6,348,350, 6,372,491 & 6,455, 496), while the mouse ANGPTL4 is a 410 amino acid protein (Kim et al., *Biochem. J.* 346:603-610 (2000)). The mouse and human share about 75% identity at the amino acid level. Kim et al., *Biochem. J.* 346:603-610 (2000). ANGPTL4 has a signal peptide, three potential N-glycosylation sites, and four cysteines that can be involved in intramolecular disulfide bonding. For example, ANGPTL4 forms higher molecular structures, e.g., as indicated in FIG. 3, Panel A. See also, e.g., Ge et al., *J. Biol. Chem.*, 279(3):2038-2045 (2004); Ge et al., *J. Lipid Res.* 45:2071-2079 (2004); and, Mandard et al., *J. of Biol. Chem.*, 279(33):34411-34420 (2004). ANGPTL4 can also be proteolytically processed. See also, e.g., Ge et al., *J. Biol. Chem.*, 279(3):2038-2045 (2004); and, Mandard et al., *J. of Biol. Chem.*, 279(33):34411-34420 (2004). As described herein, the substitution of R162G and R164E of ANGPTL4 results in the variant ANGPTL4 running at higher molecular weight on an SDS-Gel than the wild type (or native) protein (see FIG. 3, Panel B).

Conserved regions of the angiopoietin family include a coiled-coil domain and a C-terminal fibrinogen (FBN)-like domain. See, e.g., Kim et al., *Biochem. J.* 346:603-610 (2000). It is suggested that ANGPTL4 is proteolytically processed in a regulated way to release a C-terminal fibrinogen-like domain. See, e.g., Ge et al., *J. Biol. Chem.*, 279(3):2038-2045 (2004). Other members of the angiopoietin family include angiopoietin 1, angiopoietin 2 and angiopoietin3/angiopoietin 4, which bind to Tie2 receptor. See, e.g., Davis et al., *Cell* 87, 1161-1169 (1996); Maisonpierre et al., *Science* 277, 55-60 (1997); Valenzuela et al, *Proc. Natl. Acad. Sci. USA* 96, 1904-1909 (1999); and, U.S. Pat. Nos. 5,521,073; 5,650,490; and, 5,814,464. Angiopoietin 1 and 4 appear to be an agonist for the Tie2 receptor, while Angiopoietin 2 and 3 appear to be an antagonist (and possibly an agonist) for the Tie2 receptor. See, e.g., Folkman & D'Amore, *Cell,* 87:1153-1155 (1996); Suri et al., *Cell,* 87:1171-1180 (1996); Masionpierre et al., *Science* 277:55-60 (1997); and, Ward & Dumont, *Seminars in Cell & Developmental Biology,* 13:19-27 (2002).

Another member of the family, angiopoietin-like 3 protein (ANGPTL3) is an angiogeneic factor that binds to integrin $\alpha_v\beta_3$. See, e.g., US patent application 20030215451, published on Nov. 20, 2003, and Camenisch et al., *J. Biol. Chem.,* 277(19):17281-17290 (2002). ANGPTL3 does not appear to bind to receptor Tie2. Camenish et al., *Journal of Biol. Chem.* 277(19):17281-17290 (2002). ANGPTL3 is also a regulator of plasma lipid levels. See, e.g., Koishi et al., *Nat. Genetics* 30:151-157 (2002).

ANGPTL4 binds to integrin $\alpha_v\beta_5$. See, e.g., FIGS. 11, 12 and 13. Integrin $\alpha_v\beta_5$ is a receptor for extracellular matrix proteins including vitronectin, and Del-1 (see, e.g., Stupack and Cheresh, *Journal of Cell Science* 115:3729-3738 (2002)). Alpha v-integrins have been implicated in tumour progression and metastasis. See, e.g., Marshall, J F and Hart, I R *Semin. Cancer Biol.* 7(3): 129-38 (1996). In addition, a role of alpha v-integrins during angiogenesis has also been shown. See, e.g., Eliceiri, B P and Cheresh, D A *Molecular Medicine* 4: 741-750 (1998). For example, a monoclonal antibody for $\alpha_v\beta_5$ was shown to inhibit VEGF-induced angiogenesis in rabbit cornea and the chick chorioallantoic membrane model. See, e.g., M. C. Friedlander, et al., *Science* 270:1500-1502 (1995). Antagonists of $\alpha_v\beta_3$ and $\alpha_v\beta_5$ were also shown to inhibit growth-factor and tumor-induced angiogenesis. See, e.g., Eliceiri and Cheresh, *Current Opinion in Cell Biology,* 13:563-568 (2001).

The invention provides compositions of modulators, e.g., agonists or antagonists, of angiopoietin-like 4 protein (ANGPTL4) and combinations of these modulators with other therapeutic agents. For example, combinations of antagonists of ANGPTL4 with anti-cancer agents and methods of their use in the blocking or reducing tumor growth or growth of cancer cells are provided. The invention also provides methods of blocking or reducing relapse tumor growth or relapse cancer cell growth with antagonists of ANGPTL4 and/or other anti-cancer agents. Compositions of antagonists of ANGPL4 and combinations of anti-angiogenesis agents and methods for their use in blocking or reducing neovascularization of neoplastic or non-neoplastic disorders are also provided.

ANGPTL4 Modulators and Uses Thereof.

Modulators of ANGPTL4 are molecules that modulate the activity of ANGPTL4, e.g., agonists and antagonists. The term "agonist" is used to refer to peptide and non-peptide analogs of ANGPTL4, and to antibodies specifically binding such ANGPTL4 molecules, provided they have the ability to signal through a native ANGPTL4 receptor (e.g., $\alpha_v\beta_5$ integrin). The term "agonist" is defined in the context of the biological role of an ANGPTL4 receptor (e.g., $\alpha_v\beta_5$). In certain embodiments, agonists possess the biological activities of a native ANGPTL4, as defined above, such as the promotion of proliferation, migration, and/or adhesion of cells, and/or modulation of lipid homestasis.

The term "antagonist" is used to refer to molecules that have the ability to inhibit the biological activity of ANGPTL4 regardless of whether they have the ability to bind ANGPTL4 or its receptor, e.g., $\alpha_v\beta_5$. Accordingly, antagonists that have the ability to bind ANGPTL4 or its receptor include anti-ANGPTL4 and anti-$\alpha_v\beta_5$ antibodies. Antagonist ANGPTL4 can be assessed by, e.g., by inhibiting the activity of ANGPTL4, e.g., adhesion, migration, proliferation, and/or modulation of lipid homestasis activity of ANGPTL4. With regard to $\alpha_v\beta_5$ integrin receptor activity, a modulator of an $\alpha_v\beta_5$ integrin receptor can be determined by methods known in the art. For example, the method described by J. W. Smith et al. in *J. Biol. Chem.* 265:12267-12271 (1990) can be used.

Therapeutic Uses

ANGPTL4 is implicated as a cancer target. ANGPTL4, when expressed in some tumor cells, causes tumor cell proliferation, in vitro and in vivo (see, e.g., FIG. 4, FIG. 5, FIG. 7 and FIG. 8, Panel A, and Panel B). When ANGPTL4 is expressed in tumors being treated with an anti-angiogenesis factor, e.g., anti-VEGF antibody, the tumor can maintain the ability to grow (see, e.g., FIG. 8, Panel C). ANGPTL4 also causes tumor cell migration (see, e.g., FIG. 9). It has also been shown to be upregulated in renal cancers. See, e.g., Ser. No. 10/712,892; WO 02/07941; and, Le Jan et al. *American Journal of Pathology,* 162(5):1521-1528 (2003). In addition. ANGPTL4 is a proangiogenic factor (see, e.g., S. Le Jan et al., *Am. J. Pathol.,* 162(5):1521-1528 (2003)), which are targets for cancer therapy. Like VEGF (Shweiki et al., *Proc. Natl. Acad. Sci,* USA 92:768-772 (1995), ANGPTL4 expression is increased in response to hypoxia. See, e.g., Le Jan et al., *American Journal of Pathology,* 162(5):1521-1528 (2003).

ANGPTL4 binds to tumor cells, e.g., A673 cells, under various conditions (e.g., FIG. 6, Panel A and B). As seen in, e.g., FIG. 4, Panel A and Panel B, ANGPTL4 stimulates some tumor cell growth in vitro when cells are transduced with an expression construct expressing ANGPTL4. FIG. 4, Panel C also illustrates that the addition of conditioned media from COS7 cells transduced with ANGPTL4 induces the proliferation of A673 cells. See also, FIG. 7, Panel A and B. ANGPTL4 induces cell proliferation of A673 proliferation when the ANGPTL4 is coated on culture dishes (see, FIG. 5), but does not induce cell proliferation of kidney epithelial cells, renal mesangial cell or HUVEC. ANGPTL4 also induces the cell migration of tumor cells. See, e.g., FIG. 9.

ANGPTL4 is predominately expressed in adipose tissue, placenta, liver and kidney and is also up regulated in ob/ob (leptin knockout) and db/db (leptin receptor knockout) mice. See, e.g., Yoon et al., *Mol. Cell. Biol.* 20:5343-5349 (2000); Kim et al., *Biochem. J.*, 346:603-610 (2000); Kersten et al., *J. Biol. Chem.*, 275:28488-28493 (2000); and, Le Jan et al., *American Journal of Pathology* 162(5):1521-1528 (2003). ANGPTL4 was also reported to be a lipid modulator and inhibitor of lipoprotein lipase. See, e.g., Yu et al., *PNAS USA* 102(5):1767-1772 (2005); Yoshida et al., *J. Lipid Res.* 43:1770-1772 (2002); and, Wiesner et al., *J. Endocrinology* 180:R1-R6 (2004). ANGPTL4 expression is also induced by PPAR gamma and alpha in adipose tissue, and is induced by starvation. It also modulates pre-adipocyte and hepatocyte proliferation, and/or pre-adipocyte cell migration along with modulating triglyceride and cholesterol levels in the serum. See, U.S. provisional patent application 60/589,875, and PCT/US05/25650 filed concurrently, which is incorporated by reference for all purposes. Researchers have reported connections between angiogenesis and adipogenesis. See, e.g., Sierra-Honigmann et al., "Biological Action of Leptin as an Angiogenic Factor" *Science* 281:1683-1686; (1998); Rupnick et al., "Adipose tissue mass can be regulated through the vasculature" *Proc. Nat. Acad. Sci. USA*, 99(16):10730-10735 (2002); and Fukumura et al., "Paracrine Regulation of Angiogenesis and Adipocyte Differentiation During In Vivo Adipogenesis." *Circ. Res.* 93:e88-e97 (2003).

It is contemplated that, according to the invention, the ANGPTL4 modulators and/or combinations of ANGPTL4 modulators and other therapeutic agents can be used to treat various neoplasms or non-neoplastic conditions. In one embodiment, ANGPTL4 modulators, e.g., antagonists of ANGPTL4, are used in the inhibition of cancer cell or tumor growth. For example, as seen in FIG. 10, Panel A and B, anti-ANGPTL4 polyclonal antibodies inhibited tumor cell growth in a dose-dependent manner. ANGPTL4 can cause migration of tumor cells (see, e.g., FIG. 9). It is contemplated that, according to the invention, ANGPTL4 antagonists can also be used to inhibit metastasis of a tumor. ANGPTL4 also induces migration of pre-adipocytes. See, U.S. provisional patent application 60/589,875, and OCT/US05/25650 filed concurrently. In certain embodiments, one or more anti-cancer agents can be administered with ANGPTL4 antagonists to inhibit cancer cell or tumor growth. See section entitled Combination Therapies herein.

Examples of neoplastic disorders to be treated with include, but are not limited to, those described herein under the terms "cancer" and "cancerous." Non-neoplastic conditions that are amenable to treatment with antagonists of the invention include, but are not limited to, e.g., undesired or aberrant hypertrophy, arthritis, rheumatoid arthritis (RA), psoriasis, psoriatic plaques, sarcoidosis, atherosclerosis, atherosclerotic plaques, edema from myocardial infarction, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), obesity, adipose tissue mass growth, hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

Modulators of ANGPTL4, e.g., agonists or activators of ANGPTL4, can be utilized for treatments of pathological disorders. Modulators of ANGPTL4, e.g., agonists of ANGPTL4, can be utilized in the treatment of pathological disorders where angiogenesis or neovascularization and/or hypertrophy is desired, which include, but are not limited to, e.g., vascular trauma, wounds, lacerations, incisions, burns, ulcers (e.g., diabetic ulcers, pressure ulcers, haemophiliac ulcers, varicose ulcers), tissue growth, weight gain, peripheral arterial disease, induction of labor, hair growth, epidermolysis bullosa, retinal atrophy, bone fractures, bone spinal fusions, meniscal tears, etc. See also, U.S. provisional patent application 60/589,875, and PCT/US05/25650 filed concurrently.

Combination Therapies

As indicated above, the invention provides combined therapies in which an ANGPTL4 antagonist is administered with another therapy. For example, ANGPTL4 antagonists are used in combinations with anti-cancer therapeutics or an anti-neovascularization therapeutics to treat various neoplastic or non-neoplastic conditions. In one embodiment, the neoplastic or non-neoplastic condition is characterized by pathological disorder associated with aberrant or undesired angiogenesis. The ANGPTL4 antagonist can be administered serially or in combination with another agent that is effective for those purposes, either in the same composition or as separate compositions. Alternatively, or additionally, multiple inhibitors of ANGPTL4 can be administered.

The administration of the antagonist and/or agents of the invention can be done simultaneously, e.g., as a single composition or as two or more distinct compositions using the same or different administration routes. Alternatively, or additionally, the administration can be done sequentially, in any order. In certain embodiments, intervals ranging from minutes to days, to weeks to months, can be present between the administrations of the two or more compositions. For example, the anti-cancer agent may be administered first, followed by the ANGPTL4 inhibitor. However, simultaneous administration or administration of the ANGPTL4 antagonist first is also contemplated.

The effective amounts of therapeutic agents administered in combination with an ANGPTL4 antagonist will be at the physicians's or veterinarian's discretion. Dosage administration and adjustment is done to achieve maximal management of the conditions to be treated. The dose will additionally depend on such factors as the type of therapeutic agent to be used and the specific patient being treated. Suitable dosages for the anti-cancer agent are those presently used and can be lowered due to the combined action (synergy) of the anti-cancer agent and the ANGPTL4 antagonist. In certain embodiments, the combination of the inhibitors potentiates the efficacy of a single inhibitor. The term "potentiate" refers to an improvement in the efficacy of a therapeutic agent at its common or approved dose. See also the section entitled Pharmaceutical Compositions herein.

Typically, the ANGPTL4 antagonists and anti-cancer agents are suitable for the same or similar diseases to block or reduce a pathological disorder such as tumor growth or growth of a cancer cell. In one embodiment the anti-cancer agent is an anti-angiogenesis agent.

Antiangiogenic therapy in relationship to cancer is a cancer treatment strategy aimed at inhibiting the development of tumor blood vessels required for providing nutrients to support tumor growth. Because angiogenesis is involved in both primary tumor growth and metastasis, the antiangiogenic treatment provided by the invention is capable of inhibiting the neoplastic growth of tumor at the primary site as well as preventing metastasis of tumors at the secondary sites, therefore allowing attack of the tumors by other therapeutics.

Many anti-angiogenic agents have been identified and are known in the arts, including those listed herein, e.g., listed under Definitions, and by, e.g., Carmeliet and Jain, *Nature* 407:249-257 (2000); Ferrara et al., *Nature Reviews Drug Discovery*, 3:391-400 (2004); and Sato *Int. J. Clin. Oncol.*, 8:200-206 (2003). See also, US Patent Application US20030055006. In one embodiment, the ANGPTL4 antagonist is used in combination with an anti-VEGF neutralizing antibody (or fragment) and/or another VEGF antagonist or a VEGF receptor antagonist including, but not limited to, for example, soluble VEGF receptor (e.g., VEGFR-1, VEGFR-2, VEGFR-3, neuropillins (e.g., NRP1, NRP2)) fragments, aptamers capable of blocking VEGF or VEGFR, neutralizing anti-VEGFR antibodies, low molecule weight inhibitors of VEGFR tyrosine kinases (RTK), anti-sense strategies for VEGF, ribozymes against VEGF or VEGF receptors, antagonist variants of VEGF; and any combinations thereof. Alternatively, or additionally, two or more angiogenesis inhibitors may be co-administered to the patient. In certain embodiment, one or more additional therapeutic agents, e.g., anti-cancer agents, can be administered in combination with an ANGPTL4 antagonist and an anti-angiogenesis agent.

In certain aspects of the invention, other therapeutic agents useful for combination tumor therapy with an antagonist of the invention include other cancer therapies, (e.g., surgery, radiological treatments (e.g., involving irradiation or administration of radioactive substances), chemotherapy, treatment with anti-cancer agents listed herein and known in the art, or combinations thereof). Alternatively, or additionally, two or more antibodies binding the same or two or more different antigens disclosed herein can be co-administered to the patient. Sometimes, it may be beneficial to also administer one or more cytokines to the patient.

Chemotherapeutic Agents

In certain aspects, the invention provides a method of blocking or reducing tumor growth or growth of a cancer cell, by administering effective amounts of an antagonist of ANGPTL4 and/or an angiogenesis inhibitor(s) and one or more chemotherapeutic agents to a patient susceptible to, or diagnosed with, cancer. A variety of chemotherapeutic agents may be used in the combined treatment methods of the invention. An exemplary and non-limiting list of chemotherapeutic agents contemplated is provided herein under "Definition."

As will be understood by those of ordinary skill in the art, the appropriate doses of chemotherapeutic agents will be generally around those already employed in clinical therapies wherein the chemotherapeutics are administered alone or in combination with other chemotherapeutics. Variation in dosage will likely occur depending on the condition being treated. The physician administering treatment will be able to determine the appropriate dose for the individual subject.

Relapse Tumor Growth

The invention also provides methods and compositions for inhibiting or preventing relapse tumor growth or relapse cancer cell growth. For example, FIG. 8, Panel C schematically illustrates the ability of a tumor being treated with an anti-VEGF antibody (AVASTIN) to escape from the treatment (e.g., one type of relapse) when the tumor also expresses ANGPTL4.

Relapse tumor growth or relapse cancer cell growth is used to describe a condition in which patients undergoing or treated with one or more currently available therapies (e.g., cancer therapies, such as chemotherapy, radiation therapy, surgery, hormonal therapy and/or biological therapy/immunotherapy, particularly a standard therapeutic regimen for the particular cancer) is not clinically adequate to treat the patients or the patients are no longer receiving any beneficial effect from the therapy such that these patients need additional effective therapy. As used herein, the phrase can also refer to a condition of the "non-responsive/refractory" patient, e.g., which describe patients who respond to therapy yet suffer from side effects, develop resistance, do not respond to the therapy, do not respond satisfactorily to the therapy, etc. In various embodiments, a cancer is relapse tumor growth or relapse cancer cell growth where the number of cancer cells has not been significantly reduced, or has increased, or tumor size has not been significantly reduced, or has increased, or fails any further reduction in size or in number of cancer cells. The determination of whether the cancer cells are relapse tumor growth or relapse cancer cell growth can be made either in vivo or in vitro by any method known in the art for assaying the effectiveness of treatment on cancer cells, using the art-accepted meanings of "relapse" or "refractory" or "non-responsive" in such a context.

The invention provides methods of blocking or reducing relapse tumor growth or relapse cancer cell growth in a subject by administering one or more ANGPTL4 antagonists of the invention to block or reduce the relapse tumor growth or relapse cancer cell growth in subject. In certain embodiments, the ANGPTL4 antagonist can be administered subsequent to the cancer therapeutic. In certain embodiments, the ANGPTL4 is administered simultaneously with cancer therapy. Alternatively, or additionally, the ANGPTL4 antagonist therapy alternates with another cancer therapy, which can be performed in any order. The invention also encompasses methods for administering one or more ANGPTL4 inhibitory antibodies to prevent the onset or recurrence of cancer in patients predisposed to having cancer. Generally, the subject was or is concurrently undergoing cancer therapy. In one embodiment, the cancer therapy is treatment with an anti-angiogenesis agent. The anti-angiogenesis agent includes those known in the art and those found under the Definitions herein. In one embodiment, the anti-angiogenesis agent is an anti-VEGF neutralizing antibody or fragment (e.g., humanized A4.6.1, AVASTIN® (Genentech, South San Francisco, Calif.), Y0317, M4, G6, B20, 2C3, etc.). See, e.g., U.S. Pat. Nos. 6,582,959, 6,884,879, 6,703,020; WO98/45332; WO 96/30046; WO94/10202; EP 0666868B 1; US Patent Applications 20030206899, 20030190317, 20030203409, and 20050112126; Popkov et al., *Journal of Immunological Methods* 288:149-164 (2004); and, Ser. No. 60/580,757. Additional agents can be administered in combination with ANGPTL4 antagonists for blocking or reducing relapse tumor growth or relapse cancer cell growth, e.g., see section entitled Combination Therapies herein.

In one embodiment, ANGPTL4 antagonists of the invention, or other therapeutics that reduce ANGPTL4 expression, are administered to reverse resistance or reduced sensitivity of cancer cells to certain biological, hormonal, radiation and chemotherapeutic agents thereby resensitizing the cancer cells to one or more of these agents, which can then be administered (or continue to be administered) to treat or manage cancer, including to prevent metastasis.

Antibodies

Antibodies of the invention include anti-ANGPTL4 and anti-ANGPTL4 fragment antibodies, antibodies that are anti-angiogenesis agents or angiogenesis inhibitors, antibodies that are anti-cancer agents, antibodies to an ANGPTL4 receptor, e.g., anti-$\alpha_v\beta_5$ antibody, or other antibodies described herein. Exemplary antibodies include, e.g., polyclonal, monoclonal, humanized, fragment, multi specific, heteroconjugated, multivalent, effecto function, etc., antibodies.

Polyclonal Antibodies

The antibodies of the invention can comprise polyclonal antibodies. Methods of preparing polyclonal antibodies are known to the skilled artisan. For example, polyclonal antibodies against a antibody of the invention are raised in animals by one or multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N\!=\!C\!=\!NR$, where R and $R^1$ are different alkyl groups.

Animals are immunized against a molecule of the invention, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with $\frac{1}{5}$ to $\frac{1}{10}$ the original amount of peptide or conjugate in Freund's complete adjuvant by subcutaneous injection at multiple sites. Seven to 14 days later the animals are bled and the serum is assayed for antibody titer. Animals are boosted until the titer plateaus. Typically, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies

Monoclonal antibodies against an antigen described herein can be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that typically contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Typical myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against, e.g., ANGPTL4, $\alpha_v\beta_5$, or an angiogenesis molecule. The binding specificity of monoclonal antibodies produced by hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In another embodiment, antibodies or antibody fragments can be isolated from antibody phage libraries generated using the techniques described in McCafferty et al., *Nature*, 348: 552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Humanized and Human Antibodies

Antibodies of the invention can comprise humanized antibodies or human antibodies. A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.* 151:2623 (1993)).

It is further important that antibodies be humanized with retention of high affinity for the antigen and other favorable biological properties. To achieve this goal, according to a typical method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and Duchosal et al. *Nature* 355:258 (1992). Human antibodies can also be derived from phage-display libraries (Hoogenboom et al., *J. Mol. Biol.*, 227:381 (1991); Marks et al., *J. Mol. Biol.*, 222:581-597 (1991); Vaughan et al. *Nature Biotech* 14:309 (1996)).

Human antibodies can also be produced using various techniques known in the art, including phage display libraries (Hoogenboom and Winter, *J. Mol. Biol.*, 227:381 (1991); Marks et al., *J. Mol. Biol.*, 222:581 (1991)). According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, K S, and Chiswell, D J., *Cur Opin in Struct Biol* 3:564-571 (1993). Several sources of V-gene segments can be used for phage display. For example, Clackson et al., *Nature*, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated, e.g., by essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.* 147(1):86-95 (1991)). Human antibodies may also be generated by in vitro activated B cells (see U.S. Pat. Nos. 5,567,610 and 5,229,275).

Antibody Fragments

Antibody fragments are also included in the invention. Various techniques have been developed for the production of antibody fragments. Traditionally, these fragments were derived via proteolytic digestion of intact antibodies (see, e.g., Morimoto et al. *Journal of Biochemical and Biophysical Methods* 24:107-117 (1992) and Brennan et al., *Science*, 229: 81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. SFv fusion proteins may be constructed to yield fusion of an effector protein at either the amino or the carboxy terminus of an sFv. See *Antibody Engineering*, ed. Borrebaeck, supra. The antibody fragment may also be a "linear antibody", e.g., as described in U.S. Pat. No. 5,641,870 for example. Such linear antibody fragments may be monospecific or bispecific.

Multispecific Antibodies (e.g., Bispecific)

Antibodies of the invention also include, e.g., multispecific antibodies, which have binding specificities for at least two different antigens. While such molecules normally will only bind two antigens (i.e. bispecific antibodies, BsAbs), antibodies with additional specificities such as trispecific antibodies are encompassed by this expression when used herein. Examples of BsAbs include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3; BsAbs with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α(IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); BsAbs which can be used as fibrinolytic agents such as anti-fibrin/anti-tissue plasminogen activator (tPA), anti-fibrin/anti-urokinase-type plasminogen activator (uPA); BsAbs for targeting immune complexes to cell surface receptors such as anti-low density lipoprotein (LDL)/anti-Fc receptor (e.g. FcγRI, FcγRII or FcγRIII); BsAbs for use in therapy of infectious diseases such as anti-CD3/anti-herpes simplex virus (HSV), anti-T-cell receptor: CD3 complex/anti-influenza, anti-FcγR/anti-H1V; BsAbs for tumor detection in vitro or in vivo such as anti-CEA/anti-EOTUBE, anti-CEA/anti-DPTA, anti-p185$^{HER2}$/anti-hapten; BsAbs as vaccine adjuvants; and BsAbs as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase. Examples of trispecific antibodies include anti-CD3/anti-CD4/anti-CD37, anti-CD3/anti-CD5/anti-CD37 and anti-CD3/anti-CD8/anti-CD37. Bispecific antibodies can be prepared as full length antibodies or antibody fragments (e.g. F(ab'), bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the VEGF receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

Heteroconjugate Antibodies

Bispecific antibodies include cross-linked or "heteroconjugate" antibodies, which are antibodies of the invention. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Multivalent Antibodies

Antibodies of the invention include a multivalent antibody. A multivalent antibody may be internalized (and/or catabolized) faster than a bivalent antibody by a cell expressing an antigen to which the antibodies bind. The antibodies of the invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Effector Function Engineering

It may be desirable to modify the antibody of the invention with respect to effector function, so as to enhance the effectiveness of the antibody in treating cancer, for example. For example, a cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Immunoconjugates

The invention also pertains to immunoconjugates comprising the antibody described herein conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate). A variety of radionuclides are available for the production of radioconjugate antibodies. Examples include, but are not limited to, e.g., $^{212}Bi$, $^{131}I$, $^{131}In$, $^{90}Y$ and $^{186}Re$.

Chemotherapeutic agents useful in the generation of such immunoconjugates have been described above. For example, BCNU, streptozoicin, vincristine, 5-fluorouracil, the family of agents known collectively LL-E33288 complex described in U.S. Pat. Nos. 5,053,394, 5,770,710, esperamicins (U.S. Pat. No. 5,877,296), etc. (see also the definition of chemotherapeutic agents herein) can be conjugated to the anti-ANGPTL4, anti-alphaVbeta5 or anti-angiogenesis antibodies or fragments thereof.

For selective destruction of the tumor, the antibody may comprise a highly radioactive atom. A variety of radioactive isotopes are available for the production of radioconjugated anti-ANGPTL4 or anti-angiogenesis antibodies or fragments thereof. Examples include, but are not limited to, e.g., $^{211}At$, $^{131}I$, $^{125}I$, $^{90}Y$, $^{186}Re$, $^{188}Re$, $^{153}Sm$, $^{212}Bi$, $^{32}P$, $^{212}Pb$, $^{111}In$, radioactive isotopes of Lu, etc. When the conjugate is used for diagnosis, it may comprise a radioactive atom for scintigraphic studies, for example $^{99m}tc$ or $^{123}I$, or a spin label for nuclear magnetic resonance (NMR) imaging (also known as magnetic resonance imaging, MRI), such as iodine-123, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $^{99m}tc$ or $^{123}I$, $^{186}Re$, $^{188}Re$ and $^{111}In$ can be attached via a cysteine residue in the peptide. Yttrium-90 can be attached via a lysine residue. The IODOGEN method (Fraker et al (1978) *Biochem. Biophys. Res. Commun.* 80: 49-57 can be used to incorporate iodine-123. See, e.g., *Monoclonal Antibodies in Immunoscintigraphy* (Chatal, CRC Press 1989) which describes other methods in detail.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), momordica charantia inhibitor, curcin, crotin, sapaonaria officinalis inhibitor, gelonin, mitogellin, restrictocin, phenomycin, neomycin, and the tricothecenes. See, e.g., WO 93/21232 published Oct. 28, 1993.

Conjugates of the antibody and cytotoxic agent are made using a variety of bifunctional protein coupling agents such as N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208,020) may be used.

Alternatively, a fusion protein comprising the anti-ANGPTL4, the anti-$\alpha_v\beta_5$, or anti-angiogenesis antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In certain embodiments, the antibody is conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In certain embodiments, an immunoconjugate is formed between an antibody and a compound with nucleolytic activity (e.g., a ribonuclease or a DNA endonuclease such as a deoxyribonuclease; Dnase).

Maytansine and Maytansinoids

The invention provides an antibody of the invention, which is conjugated to one or more maytansinoid molecules. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Anti-ANGPTL4, anti-$\alpha_v\beta_5$, or anti-angiogenesis antibody is conjugated to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and non-patent publications referred to hereinabove. In one embodiment, maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Typical coupling agents include N-succinimidyl-3-(2-pyridyldithio)propionate (SPDP) (Carlsson et al., *Biochem. J.* 173:723-737 [1978]) and N-succinimidyl-4-(2-pyridylthio) pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hyrdoxymethyl, the C-15 position modified with a hydroxyl group, and the C-20 position having a hydroxyl group. The linkage is formed at the C-3 position of maytansinol or a maytansinol analogue.

Calicheamicin

Another immunoconjugate of interest comprises an antibody of the invention conjugated to one or more calicheamicin molecules. The calicheamicin family of antibiotics is capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Antibody Modifications

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules, or in macroemulsions. Such techniques are disclosed in *Remington's Pharmaceutical Sciences*, 16th edition, Oslo, A., Ed., (1980).

Liposomes and Nanoparticles

Polypeptides of the invention can be formulated in liposomes. For example, antibodies of the invention can be formulated as immunoliposomes. Liposomes containing the antibody are prepared by methods known in the art, such as described in Epstein et al., *Proc. Natl. Acad. Sci. USA,* 82:3688 (1985); Hwang et al., *Proc. Natl Acad. Sci. USA.* 77:4030 (1980); and U.S. Pat. Nos. 4,485,045 and 4,544,545. Liposomes with enhanced circulation time are disclosed in U.S. Pat. No. 5,013,556. Generally, the formulation and use of liposomes is known to those of skill in the art.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the invention can be conjugated to the liposomes as described in Martin et al. *J. Biol. Chem.* 257: 286-288 (1982) via a disulfide interchange reaction. A chemotherapeutic agent (such as Doxorubicin) is optionally contained within the liposome. See Gabizon et al. *J. National Cancer Thst.* 81(19)1484 (1989).

Other Uses

The antibodies of the invention have various utilities. For example, anti-ANGPTL4 antibodies may be used in diagnostic assays for ANGPTL4, e.g., detecting its expression in specific cells, tissues, or serum, for cancer detection (e.g., in detecting renal cancer), etc. In one embodiment, ANGPTL4 antibodies are used for selecting the patient population for treatment with the methods provided herein, e.g., for patients with ANGPTL4 expression, elevated ANGPTL4 levels, or cancers sensitive to ANGPTL4 levels. Various diagnostic assay techniques known in the art may be used, such as competitive binding assays, direct or indirect sandwich assays and immunoprecipitation assays conducted in either heterogeneous or homogeneous phases (Zola, *Monoclonal Antibodies: A Manual of Techniques*, CRC Press, Inc. (1987) pp. 147-158). The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature,* 144:945 (1962); David et al., *Biochemistry,* 13:1014 (1974); Pain et al., *J. Immunol. Meth.,* 40:219 (1981); and Nygren, *J. Histochem. And Cytochem.,* 30:407 (1982).

Anti-ANGPTL4 antibodies also are useful for the affinity purification of ANGPTL4 or ANGPTL4 fragments from recombinant cell culture or natural sources. In this process, the antibodies against ANGPTL4 are immobilized on a suitable support, such a Sephadex resin or filter paper, using methods well known in the art. The immobilized antibody then is contacted with a sample containing the ANGPTL4 to be purified, and thereafter the support is washed with a suitable solvent that will remove substantially all the material in the sample except the ANGPTL4, which is bound to the immobilized antibody. Finally, the support is washed with another suitable solvent that will release the ANGPTL4 from the antibody.

Covalent Modifications to Polypeptides of the Invention

Covalent modifications of a polypeptide of the invention, e.g., a polypeptide antagonist fragment, a fusion molecule (e.g., an immunofusion molecule), an antibody of the invention, are included within the scope of this invention. They may be made by chemical synthesis or by enzymatic or chemical cleavage of the polypeptide, if applicable. Other types of covalent modifications of the polypeptide are introduced into the molecule by reacting targeted amino acid residues of the polypeptide with an organic derivatizing agent that is capable of reacting with selected side chains or the N- or C-terminal residues, or by incorporating a modified amino acid or unnatural amino acid into the growing polypeptide chain, e.g., Ellman et al. *Meth. Enzym.* 202:301-336 (1991); Noren et al. *Science* 244:182 (1989); and, & US Patent application publications 20030108885 and 20030082575.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is typically performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl)carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to a polypeptide of the invention. These procedures are advantageous in that they do not require production of the polypeptide in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (1) the amide group of glutamine. These methods are described in WO 87/05330 published 11 Sep. 1987, and in Aplin and Wriston, *CRC Crit. Rev. Biochem.*, pp. 259-306 (1981).

Removal of any carbohydrate moieties present on a polypeptide of the invention may be accomplished chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin, et al. *Arch. Biochem. Biophys.* 259:52 (1987) and by Edge et al. *Anal. Biochem.*, 118:131 (1981). Enzymatic cleavage of carbohydrate moieties, e.g., on antibodies, can be achieved by the use of a variety of endo- and exo-glycosidases as described by Thotakura et al. *Meth. Enzymol.* 138:350 (1987).

Another type of covalent modification of a polypeptide of the invention comprises linking the polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Vectors, Host Cells and Recombinant Methods

The polypeptides of the invention can be produced recombinantly, using techniques and materials readily obtainable.

For recombinant production of a polypeptide of the invention, e.g., an ANGPTL4 or an anti-ANGPTL4 antibody, an anti-$α_vβ_5$ antibody or anti-angiogenesis antibody, e.g., anti-VEGF antibody, the nucleic acid encoding it is isolated and inserted into a replicable vector for further cloning (amplification of the DNA) or for expression. DNA encoding the polypeptide of the invention is readily isolated and sequenced using conventional procedures. For example, a DNA encoding a monoclonal antibody is isolated and sequenced, e.g., by using oligonucleotide probes that are capable of binding specifically to genes encoding the heavy and light chains of the antibody. Many vectors are available. The vector components generally include, but are not limited to, one or more of the following: a signal sequence, an origin of replication, one or more marker genes, an enhancer element, a promoter, and a transcription termination sequence.

Signal Sequence Component

Polypeptides of the invention may be produced recombinantly not only directly, but also as a fusion polypeptide with a heterologous polypeptide, which is typically a signal sequence or other polypeptide having a specific cleavage site at the N-terminus of the mature protein or polypeptide. The heterologous signal sequence selected typically is one that is recognized and processed (i.e., cleaved by a signal peptidase) by the host cell. For prokaryotic host cells that do not recognize and process the native polypeptide signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the polypeptide of the invention.

Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, typically primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding a polypeptide of the invention, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid Yrp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

Promotor Component

Expression and cloning vectors usually contain a promoter that is recognized by the host organism and is operably linked to a nucleic acid encoding a polypeptide of the invention. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the polypeptide of the invention.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic-genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldyhyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Transcription of polypeptides of the invention from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and typically Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419, 446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the rous sarcoma virus long terminal repeat can be used as the promoter.

Enhancer Element Component

Transcription of a DNA encoding a polypeptide of this invention by higher eukaryotes is often increased by inserting an enhancer sequence into the vector. Many enhancer sequences are now known from mammalian genes (globin, elastase, albumin, α-fetoprotein, and insulin). Typically, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the polypeptide-encoding sequence, but is typically located at a site 5' from the promoter.

Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptide of the invention. One useful transcription termination component is the bovine growth hormone polyadenylation region. See WO94/11026 and the expression vector disclosed therein.

Selection and Transformation of Host Cells

Suitable host cells for cloning or expressing DNA encoding the polypeptides of the invention in the vectors herein are the prokaryote, yeast, or higher eukaryote cells described above. Suitable prokaryotes for this purpose include eubacteria, such as Gram-negative or Gram-positive organisms, for example, Enterobacteriaceae such as Escherichia, e.g., E. coli, Enterobacter, Erwinia, Klebsiella, Proteus, Salmonella, e.g., Salmonella typhimurium, Serratia, e.g., Serratia marcescans, and Shigella, as well as Bacilli such as B. subtilis and B. licheniformis (e.g., B. licheniformis 41 P disclosed in DD 266,710 published 12 Apr. 1989), Pseudomonas such as P. aeruginosa, and Streptomyces. Typically, the E. coli cloning host is E. coli 294 (ATCC 31,446), although other strains such as E. coli B, E. coli X1776 (ATCC 31,537), and E. coli W3110 (ATCC 27,325) are suitable. These examples are illustrative rather than limiting.

In addition to prokaryotes, eukaryotic microbes such as filamentous fungi or yeast are suitable cloning or expression hosts for polypeptide of the invention-encoding vectors. Saccharomyces cerevisiae, or common baker's yeast, is the most commonly used among lower eukaryotic host microorganisms. However, a number of other genera, species, and strains are commonly available and useful herein, such as Schizosaccharomyces pombe; Kluyveromyces hosts such as, e.g., K. laths, K. fragilis (ATCC 12,424), K. bulgaricus (ATCC 16,045), K. wickeramii (ATCC 24,178), K. waltii (ATCC 56,500). K. drosophilarum (ATCC 36,906), K. thermotolerans, and K. marxianus; yarrowia (EP 402,226); Pichia pastoris (EP 183,070); Candida; Trichoderma reesia (EP 244, 234); Neurospora crassa; Schwanniomyces such as Schwanniomyces occidentalis; and filamentous fungi such as, e.g., Neurospora, Penicillium, Tolypocladium, and Aspergillus hosts such as A. nidulans and A. niger.

Suitable host cells for the expression of glycosylated polypeptides of the invention are derived from multicellular organisms. Examples of invertebrate cells include plant and insect cells. Numerous baculoviral strains and variants and corresponding permissive insect host cells from hosts such as Spodoptera frugiperda (caterpillar), Aedes aegypti (mosquito), Aedes albopictus (mosquito), Drosophila melanogaster (fruitfly), and Bombyx mori have been identified. A variety of viral strains for transfection are publicly available, e.g., the L-1 variant of Autographa californica NPV and the Bm-5 strain of Bombyx mori NPV, and such viruses may be used as the virus herein according to the invention, particularly for transfection of Spodoptera frugiperda cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/−DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for polypeptide of the invention production and cultured in conventional nutrient media modified as appropriate for inducing promoters, selecting transformants, or amplifying the genes encoding the desired sequences.

Culturing the Host Cells

The host cells used to produce polypeptides of the invention may be cultured in a variety of media. Commercially available media such as Ham's Flo (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Polypeptide Purification

When using recombinant techniques, a polypeptide of the invention, e.g., ANGPTL4, antibodies of the invention, e.g., anti-ANGPTL4 antibody, anti-$\alpha_v\beta_5$ antibody or anti-angiogenesis molecule antibody, can be produced intracellularly, in the periplasmic space, or directly secreted into the medium. Polypeptides of the invention may be recovered from culture medium or from host cell lysates. If membrane-bound, it can be released from the membrane using a suitable detergent solution (e.g. Triton-X 100) or by enzymatic cleavage. Cells employed in expression of a polypeptide of the invention can be disrupted by various physical or chemical means, such as freeze-thaw cycling, sonication, mechanical disruption, or cell lysing agents.

It may be desired to purify a polypeptide of the invention from recombinant cell proteins or polypeptides. The following procedures are exemplary of suitable purification procedures: by fractionation on an ion-exchange column; ethanol precipitation; reverse phase HPLC; chromatography on silica, chromatography on heparin SEPHAROSE™ chromatography on an anion or cation exchange resin (such as a polyaspartic acid column, DEAE, etc.); chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of polypeptides of the invention. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular polypeptide of the invention produced.

For example, an antibody composition prepared from the cells can be purified using, for example, hydroxylapatite chromatography, gel electrophoresis, dialysis, and affinity chromatography, with affinity chromatography being the typical purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification, e.g., those indicated above, are also available depending on the antibody to be recovered. See also, Carter et al., *Bio/Technology* 10:163-167 (1992) which describes a procedure for isolating antibodies which are secreted to the periplasmic space of *E. coli*.

Pharmaceutical Compositions

Therapeutic formulations of polypeptides of the invention, molecules of the invention, and combinations thereof and described herein used in accordance with the invention are prepared for storage by mixing a polypeptide(s) having the desired degree of purity with optional pharmaceutically acceptable carriers, excipients or stabilizers (*Remington's Pharmaceutical Sciences* 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing a polypeptide of the invention, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions. See also, e.g., U.S. Pat. No. 6,699,501, describing capsules with polyelectrolyte covering.

It is further contemplated that an agent of the invention (ANGPTL4, ANGPTL4 agonist or ANGPTL4 antagonist) can be introduced to a subject by gene therapy. Gene therapy refers to therapy performed by the administration of a nucleic acid to a subject. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. See, e.g., Ad-ANGPTL4-SiRNA described herein. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 (1986)). The oligonucleotides can be modified to enhance their uptake, e.g. by substituting their negatively charged phosphodiester groups by uncharged groups. For general reviews of the methods of gene therapy, see, for example, Goldspiel et al. *Clinical Pharmacy* 12:488-505 (1993); Wu and Wu *Biotherapy* 3:87-95 (1991); Tolstoshev *Ann. Rev. Pharmacol. Toxicol.* 32:573-596 (1993); Mulligan *Science* 260:926-932 (1993); Morgan and Anderson *Ann. Rev. Biochem.* 62:191-217 (1993); and May *TIBTECH* 11:155-215 (1993). Methods commonly known in the art of recombinant DNA technology which can be used are described in Ausubel et al. eds. (1993) *Current Protocols in Molecular Biology*, John Wiley & Sons, NY; and Kriegler (1990) *Gene Transfer and Expression, A Laboratory Manual*, Stockton Press, NY.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 (1993)). For example, in vivo nucleic acid transfer techniques include transfection with viral vectors (such as adenovirus, Herpes simplex I virus, lentivirus, retrovirus, or adeno-associated virus) and lipid-based systems (useful lipids for lipid-mediated transfer of the gene are DOTMA, DOPE and DC-Chol, for example). Examples of using viral vectors in gene therapy can be found in Clowes et al. *J. Clin. Invest.* 93:644-651 (1994); Kiem et al. *Blood* 83:1467-1473 (1994); Salmons and Gunzberg *Human Gene Therapy* 4:129-141 (1993); Grossman and Wilson *Curr. Opin. in Genetics and Devel.* 3:110-114 (1993); Bout et al. *Human Gene Therapy* 5:3-10 (1994); Rosenfeld et al. *Science* 252:431-434 (1991); Rosenfeld et al. *Cell* 68:143-155 (1992); Mastrangeli et al. *J. Clin. Invest.* 91:225-234 (1993); and Walsh et al. *Proc. Soc. Exp. Biol. Med.* 204:289-300 (1993).

In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

Dosage and Administration

The molecules of the invention are administered to a human patient, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes, and/or subcutaneous administration.

In certain embodiments, the treatment of the invention involves the combined administration of an ANGPTL4 antagonist and one or more anti-cancer agents, e.g., anti-angiogenesis agents. In one embodiment, additional anti-cancer agents are present, e.g., one or more different anti-angiogenesis agents, one or more chemotherapeutic agents, etc. The invention also contemplates administration of multiple inhibitors, e.g., multiple antibodies to the same antigen or multiple antibodies to different cancer active molecules. In one embodiment, a cocktail of different chemotherapeutic agents is administered with the ANGPTL4 antagonist and/or one or more anti-angiogenesis agents. The combined administration includes coadministration, using separate formulations or a single pharmaceutical formulation, and/or consecutive administration in either order. For example, an ANGPTL4 antagonist may precede, follow, alternate with administration of the anti-cancer agents, or may be given simultaneously therewith. In one embodiment, there is a time period while both (or all) active agents simultaneously exert their biological activities.

For the prevention or treatment of disease, the appropriate dosage of ANGPTL4 antagonist will depend on the type of disease to be treated, as defined above, the severity and course of the disease, whether the inhibitor is administered for preventive or therapeutic purposes, previous therapy, the patient's clinical history and response to the inhibitor, and the discretion of the attending physician. The inhibitor is suitably administered to the patient at one time or over a series of treatments. In a combination therapy regimen, the compositions of the invention are administered in a therapeutically effective amount or a therapeutically synergistic amount. As used herein, a therapeutically effective amount is such that administration of a composition of the invention and/or co-administration of ANGPTL4 antagonist and one or more other therapeutic agents, results in reduction or inhibition of the targeting disease or condition. The effect of the administration of a combination of agents can be additive. In one embodiment, the result of the administration is a synergistic effect. A therapeutically synergistic amount is that amount of ANGPTL4 antagonist and one or more other therapeutic agents, e.g., an angiogenesis inhibitor, necessary to synergistically or significantly reduce or eliminate conditions or symptoms associated with a particular disease.

Depending on the type and severity of the disease, about 1 µg/kg to 50 mg/kg (e.g. 0.1-20 mg/kg) of ANGPTL4 antagonist or angiogenesis inhibitor is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. Typically, the clinician will administered a molecule(s) of the invention until a dosage(s) is reached that provides the required biological effect. The progress of the therapy of the invention is easily monitored by conventional techniques and assays.

For example, preparation and dosing schedules for angiogenesis inhibitors, e.g., anti-VEGF antibodies, such as AVASTIN® (Genentech), may be used according to manufacturers' instructions or determined empirically by the skilled practitioner. In another example, preparation and dosing schedules for such chemotherapeutic agents may be used according to manufacturers' instructions or as determined empirically by the skilled practitioner. Preparation and dosing schedules for chemotherapy are also described in *Chemotherapy Service* Ed., M. C. Perry, Williams & Wilkins, Baltimore, Md. (1992).

Efficacy of the Treatment

The efficacy of the treatment of the invention can be measured by various endpoints commonly used in evaluating neoplastic or non-neoplastic disorders. For example, cancer treatments can be evaluated by, e.g., but not limited to, tumor regression, tumor weight or size shrinkage, time to progression, duration of survival, progression free survival, overall response rate, duration of response, and quality of life. Because the anti-angiogenic agents described herein target the tumor vasculature and not necessarily the neoplastic cells themselves, they represent a unique class of anticancer drugs, and therefore can require unique measures and definitions of clinical responses to drugs. For example, tumor shrinkage of greater than 50% in a 2-dimensional analysis is the standard cut-off for declaring a response. However, the inhibitors of the invention may cause inhibition of metastatic spread without shrinkage of the primary tumor, or may simply exert a tumouristatic effect. Accordingly, approaches to determining efficacy of the therapy can be employed, including for example, measurement of plasma or urinary markers of angiogenesis and measurement of response through radiological imaging.

In one embodiment, the invention can be used for increasing the duration of survival of a human patient susceptible to or diagnosed with a non-neoplastic or neoplastic disorder, e.g., cancer. Duration of survival is defined as the time from first administration of the drug to death. In a one aspect, an ANGPTL4 antagonist of the invention is administered to the human patient in combination with one or more anti-cancer agents, thereby the duration of survival of the patient is effectively increased as compared to a single type of therapy alone, e.g., increased by about 5%, or increased by about 10%, or increased about 20%, or increased about 30%, or increased about 40%, or increased about 50% or more, compared to the a single type of therapy.

In another embodiment, the invention provides methods for increasing progression free survival of a human patient susceptible to or diagnosed with a non-neoplastic or neoplastic disorder, e.g., cancer. Time to disease progression is defined as the time from administration of the drug until disease progression. In a one embodiment, the combination treatment of the invention using ANGPTL4 antagonist and one or more anti-cancer agents significantly increases progression free survival by at least about 2 months, at least about 4 months, at least about 6 months, at least about 8 months, a year or greater, when compared to an anti-cancer treatment with alone.

In yet another embodiment, the treatment of the invention significantly increases response rate in a group of human patients susceptible to or diagnosed with a cancer who are treated with various therapeutics. Response rate is defined as the percentage of treated patients who responded to the treatment. In one embodiment of the invention, the combination treatment of the invention using ANGPTL4 antagonist and one or more anti-cancer agents significantly increases response rate in the treated patient group compared to the group treated with a single type of cancer therapy (e.g., chemotherapy alone), said increase having a Chi-square p-value, e.g., of less than 0.010, or less than 0.005, or less than 0.001.

In one aspect, the invention provides methods for increasing duration of response in a human patient or a group of human patients susceptible to or diagnosed with a cancer. Duration of response is defined as the time from the initial response to disease progression. In certain embodiments of the invention, a combination treatment of the invention using ANGPTL4 antagonist and one or more anti-cancer agents, a statistically significant increase of, e.g., at least 2 months, at least 4 months, at least 6 months, in duration of response can be obtain.

Articles of Manufacture

In another embodiment of the invention, an article of manufacture containing materials useful for the treatment of the disorders described above is provided. The article of manufacture comprises a container, a label and a package insert. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is an ANGPTL4 modulator. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including additional active agents, other buffers, diluents, filters, needles, and syringes.

Deposit of Materials

The following material has been deposited with the American Type Culture Collection, 10801 University Boulevard, Manassas, Va. 20110-2209, USA (ATCC):

| Material | ATCC Deposit No. | Deposit Date |
|---|---|---|
| ANGPTL4 (NL2-DNA 22780-1078) | 209284 | Sep. 18, 1997 |
| Hybridoma cell line producing Antibody A4.6.1 | ATCC HB-10709 | Mar. 29, 1997 |

The deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

EXAMPLES

It is understood that the deposits, examples and embodiments described herein are for illustrative purposes only and that various modifications or changes in light thereof will be suggested to persons skilled in the art and are to be included within the spirit and purview of this application and scope of the appended claims. Commercially available reagents referred to in the examples were used according to manufacturer's instructions unless otherwise indicated.

Example 1

ANGPTL4 Stimulates Tumor Cell Proliferation and Cell Migration

Generation of Adenoviral Vectors and Transduction:

Adenoviral constructs have been constructed by cloning the Not1-Not1 cDNA insert into the polylinker site of the Ad-easy vector construction kits from Stratagene (LaJolla, Calif.), essentially as described by the manufacturer. See, e.g., Hesser et al., *Blood,* 104(1):149-158 (2004).

Generation of hAngptl4(23-406) (PUR9384), mAngptl4 (184-410)-IgG (PUR9388) and mAngptl4(23-410) (PUR9452) Single Flag Tagged Protein:

Harvested cell culture fluid was passed overnight onto anti-flag M2 resin (Sigma#A-2220). The column was washed to base-line with PBS then eluted with 50 mM Na Citrate pH3.0. This volume was concentrated on Amicon-15 10,000MWCO (Millipore #UFC901024). The final step was dialysis into 1 mM HCl/Super Q $H_2O$ and 0.2 um filtration. A 4-20% tris/glycine (Invitrogen#EC6028box) SDS page gel+/−10 mM DTT was used to determine purity. Correct proteins were identified by either Mass Spec or Edman's n-terminal sequencing.

Generation of hAngptl4(184-406)-IgG (PUR 9441) n-Terminal Flag Tag Followed in Series by an n-Terminal hu Fc Tag:

Harvested cell culture fluid was passed overnight onto ProSep A (Amersham #113111835). The column was washed to base-line with PBS. Then a four column volume 0.5M TMAC/PBS pH 7.5 wash step was followed by a PBS wash to base line. The elution step was a 50 mM Na Citrate pH 3.0 bump. This volume was concentrated on Amicon-15 10,000 MWCO (Millipore #UFC901024). The final step was dialysis into 1 mM HCl/Super Q H2O and 0.2 um filtration. A 4-20% tris/glycine (Invitrogen#EC6028box) SDS page gel+/−10 mM DTT is used to determine purity. Correct proteins were identified by either Mass Spec or Edman's n-terminal sequencing: Recombinant proteins can also be made using standard techniques known in the art.

Generation of Ad-ANGPTL4-SiRNA:

4 potential ANGPTL4-SiRNA molecules (Qiagen) were generated based on the full length hANGPTL4 sequence. One ANGPTL4-SiRNA was selected based on the ability of the SiRNA to inhibit hANGPTL4 expression. It targeted the following DNA target sequence GTGGCCAAGCCTGC-CCGAAGA of ANGPTL4, e.g., r(GGCCAAGCCUGC-CCGAAGAUU) and/or r(UCUUCGGGCAGGCUUGGCCAC) The SiRNA was cloned into CMVpShuttle-H1.1 transfer vector with an RNA promoter, e.g., H1 promoter (GenScript). The SiRNA expression cassette was then cloned to generate an adenoviral AdhANGPTL4-SiRNA construct. For example, adenoviral constructs have been constructed by cloning the Not1-Not1 cDNA insert into the polylinker site of the Ad-easy vector construction kits from Stratagene (LaJolla, Calif.), essentially as described by the manufacturer. See, e.g., Hesser et al., *Blood,* 104(1):149-158 (2004).

Expression of ANGPTL4 was verified by Western blotting analysis using an anti-FLAG antibody. One strongly expressing clone was selected and titers were amplified according to the manufactures instruction. Viral preparations were purified by CsCl centrifugation and tested for revertants by PCR. Viral titers were determined by 96 well cell lysis experiments according to the manufacturers instructions. These vectors, along with the supplied pShuttleCMV-lacZ, were recombined, in BJ5183 electro competent bacteria with the AdEasy vector containing the Ad5 genome deleted for E1 and E3 regions. Primary viral stocks were prepared by transiently transfecting the recombined AdEasy plasmids into host HEK293 cells. Adenovirus stocks were further amplified in HEK293 cells and purified using CsCl gradient purification method as described by the manufacturer. Adenovirus working titers were obtained by Elisa assay.

Generation of mANGPTL4:

293 cells were transiently transfected with a construct which contained a nucleic acid encoding the full length mANGPTL4 (1-410). mANGPTL4 was purified from the supernatant and used for experiments.

Tumor Cell Proliferation In Vitro:

ANGPTL4 stimulated human A673 rhabdomyosarcoma tumor cells (HTB 1598) proliferation in vitro. See FIG. 4, Panel A. Adenoviral constructs of Ad-Angptl4, Ad-LacZ, Ad-Angptl3 were generated as described previously (Hesser et al, *Blood,* 104(1):149-158 (2004)). A673 cells were transduced with either a construct comprising the adenovirus-ANGPTL4 construct (Ad-Angptl4), the adenovirus-LacZ construct (Ad-LacZ) as a control or the adenovirus-ANGPTL3 construct (Ad-Angptl3) at the multiplicity of infection (MOI) of 100. After 3 days of growing the A673 cells in 5% FCS high glucose DMEM, the cells were counted. As indicated in FIG. 4, Panel A, the Ad-Angptl4 stimulated tumor cell proliferation. About a greater than 2 fold increase in cell number was seen in cells treated with Ad-Angptl4 as compared to the Ad-LacZ control. Ad-Angptl4 also stimulated the proliferation of MCF7 cells (human breast adenocarcinoma) about 3 fold, TK10 cells (renal cell cancer line) about 2 fold, and A549 cells (human lung carcinoma) about 1.5 fold compared to control. Ad-Angptl4 also stimulated the proliferation of U87MG cells. See, FIG. 4, Panel B, where cells (A673, U87MG, 4T-1, or Caki) were transduced with either a construct comprising the adenovirus-ANGPTL4 construct (Ad-Angptl4 (2)), the adenovirus-LacZ construct (Ad-LacZ (1)) as a control or the adenovirus ANGPTL4-SiRNA construct (3) at the multiplicity of infection (M01) of 500. After 2-3 days of growing the cells in 5% FCS high glucose DMEM, the cells were counted.

Conditioned media from COS cells transduced with ANGPTL4 also induced proliferation of A673 cells. See FIG. 4, Panel C. Conditioned media (supernatant) from Hepatocytes (Hepa) (A), Human microvascular endothelial cells (HMEC) cells (B), or COS7 (C) that were transduced with adenoviral constructs (Ad-Angptl4 (2), Ad-LacZ (1) or Ad-Angptl3(3)) was added to A673 cells. After 4 days of growing the A673 cells in 5% FCS high glucose DMEM, the cells were counted. As indicated in FIG. 4, Panel C, the supernatant from COS cell+Ad-Angptl4 stimulated tumor cell proliferation compared to the controls and other supernatant from other cell types that were used, e.g., Hepa cells and HMVEC cells.

Angptl4 Activity when Coated onto Culture Dishes:

Proliferation of A673 cells by Angptl4 was also examined by coating protein onto cultured dishes. Plates were coated with murine Angptl4, LZ-hANgptl4, Fibronectin, NL4 a control protein, IgG-hAngptl4 (184-406), mAngptl3, hAngptl3, mAngptl4 (23-410), Lz-hAngptl4 (184-406), Fc-hAngptl4 (184-406) or BSA, at various concentrations, e.g., no coating, 0.3 µg/ml, 3.0 µg/ml or 30 µg/ml. 96-well flat-bottomed plates (MaxiSorp, Nunc, Denmark) were coated overnight at 4° C. Human A673 tumor cells were harvested and diluted to $10^5$ cells/ml in HG-DMEM medium containing 5% FCS. Cell suspensions ($10^4$ cells/well) in 200 µl were added to the coated wells and the plates were incubated at 37° C. for selected times. Non-adherent cells were removed by PBS washes and cell attachment was measured using either crystal violet or the PNAG method of Landegren. See, Landegren, U. (1984) *J. Immunol. Methods* 67:379-388. Results are expressed at mean $OD_{550}$ or $OD_{405}$ values of triplicate wells, respectively.

Similarly, human primary umbilical vein endothelial cells (HUVEC) epithelial (epi) and mesangial (mesa) cells isolated from either human umbilical cords or human kidneys (Cambrex) were harvest and tested by using identical conditions. For the proliferation assay, the medium supplied for each cell type by the manufacturer (Cambrex) was used. ANGPTL4 appeared not to induce proliferation of kidney epithelial cells, renal mesangial cells or human umbilical vein endothelial cells (HUVEC), but did induce proliferation of A673 (FIG. 5).

FACS Analysis of ANGPTL4 Binding to A673 Cells:

Binding of ANGPTL4 to human A673 cells was examined by FACS analysis. A673 cells were plated in 10 cm cultured dishes at 500,000 to $1 \times 10^6$ cells/sample well. The cells were split the day before the FACS. The cells were washed once with PBS and then 10 ml of 20 mM EDTA in PBS was added and incubated for 10 to 20 minutes. After 20 minutes, cells were scraped from plate. 10 ml of 5% FCS in PBS was added and cells were transferred to a 50 ml Falcon tube. The cells were spun down at 1.8 K rpm for 5 minutes at 4° C. The supernatant was removed and the cells were resuspended in 1 ml of 5% FCS in PBS. 100 µl of cell suspension was distributed into a 5 ml FACS tubes containing 1 µg of protein and incubated for 30 minutes or greater on ice. The following proteins were used: mAngptl4 (23-410), PUR 9452, 0.428 mg/ml (41/sample); hAngptl4 (23-406), PUR 9384, +/−90 µg/ml (10 µl/sample); hAngptl4 (184-406)-IgG, PUR 9441, 1.5 mg/ml (1 µl/sample); and control FLAG-BAP (Sigma) 0.1 mg/ml (2 µl/sample). After incubation, tubes were filled with 5 ml of 5% FCS in PBS on ice. The cells were spun down for 5 minutes at 2K rpm. The supernatant was removed. Anti-FLAG-FITC antibody (Sigma) was added (2 µl of antibody (100 µg/ml stock) and incubated on ice for 5 minutes or greater. The final antibody concentration was 1 mg/ml. 5 ml of 5% FCS in PBS was added and cells were spun down 5 minutes at 1.8 K rpm at 4° C. The supernatant was removed and cells were resuspended in 0.25 ml PBS with 5% FCS on ice. 0.05% sodium azide may be also present to prevent receptor internalization. 1 µl of 1:50 diluted stock of propidium iodide (PI) can be added per sample. The cells were then subject to FACS. Various forms of ANGPTL4 both human and murine ANGPTL4 bound to A673 cells (FIG. 6, Panel A) under various conditions (FIG. 6, Panel B), normoxia, hypoxia (0% $O_2$, for 24 hours, or PMA (200 nM for 24 hours). For hypoxia experiments, cells were incubated for 24 hours at 37° C. in 5% $CO_2$, 95% $N_2$ incubator for 24 hours. Alternatively, cells were activated in presence of 200 nM phorbol ester (PMA) in a 37° C. incubator, 5% $CO_2$ and normoxic conditions.

Conditioned media from cells expressing ANGPTL4: The proliferation of A673 cells when using conditioned media from cells expressing Angptl4 or adding recombinant Angptl4 was examined. 500 µl of conditioned media (supernatant) from COS7 that were transduced with adenoviral constructs (Ad-Angptl4 (2), Ad-LacZ(1) or Ad-LacZ+rmAngptl4 (23-410) (3) (5 µg/ml)) was added to A673 cells. After cells were grown for 7 days (FIG. 7, Panel A) in media containing 5 FCS, high glucose DMEM, the cells were counted. A673 proliferation was also examined by adding recombinant Angptl4 to the media with 5% FCS and growing the cells for 4 days. Either there was no addition (1), or a buffer control (2), mAngptl4 (23-410) (2.5 µg/ml) (3), hAngptl4 (23-406) (2.5 µg/ml) (4), hIgG-hAngptl4 (184-406) (2.5 µg/ml)(5) or hIgG-mAngptl4 (184-410) (2.5 µg/ml) (6) was added in the media at the indicated concentration. After cells were grown for 4 days (FIG. 7, Panel B) in media containing 5 FCS, high glucose DMEM, the cells were counted. Proliferation of A673 cells by conditioned media from cells expressing ANGPTL4 or recombinant protein added to the media may be cell density dependent. See FIG. 7, Panel A (cell proliferation when grown for 7 days under stated conditions) and Panel B (cell proliferation when grown for 4 days under the stated conditions).

Angptl4 Induces Cell Migration:

We examined Angptl4 ability to induce cell migration of murine 4T-1 tumor cells. Cell motility was measured as described (see, e.g., Camenisch, et al., *J. Biol. Chem.*, 277 (19):17281-17290 (2002)) using HTS Multiwell tissue culture inserts with 3 µm pore size (Becton Dickinson, N.J.). hANGPTL4 (1-406) was diluted in 50/50/0.1% BSA to 5, 1 and 0.2 µg/ml. As a positive control, membranes were incubated with either 10% fetal calf serum (FCS) containing medium or 0.1 µg/ml of recombinant human PDGF-BB (R&D Systems). 50/50/0.1% BSA was used as a negative control. Mouse 4T1 tumor cells were washed three times with PBS, harvested and suspended at about $10^5$ cells/ml in 50/50/0.1% BSA. The following cell preparations were tested, where mANGPTL4 is indicated as NL2.

| 4T-1 | |
| --- | --- |
| 50/50/0.1% BSA | NL2 5 ug |
| +10% FBS | NL2 0.5 ug |
| +10% FBS | NL2 0.2 ug |
| 50/50/0.1% BSA | PDGF-BB 0.1 ug |

The preparations were added to the bottom chamber and the preparations were incubated at 37° C. for 19 hours.

The cell suspension (250 µl) was added to the upper chamber and the cells were allowed to migrate overnight at 37° C.

in a 5% CO$_2$ humidified incubator. After incubation, medium was aspirated from the both top and bottom chambers, and cells that had migrated to the lower surface of the membrane were fixed with methanol (400 µl of MeOH for 30 minutes at 4° C., remove MeOH and air dry for 40 minutes) and stained with YO-PRO-1 iodide (Molecular Probes, OR) (400 µl YO-PRO-1 iodide at 10 µm (1:100 from 1 mM stock)). Migration results are quantitated in terms of the average number of cells/microscopic field at a 20-fold magnification using the Openlab software (Improvision, Mass.).

In another experiment, Angptl4 was found to induce migration of A673 cells along with migration of 4T-1 tumor cells. mANGPTL4 was diluted in 50/50/0.1% BSA to 6, 1.5 and 0.375 µg/ml. As a positive control, membranes were incubated with either 10% fetal calf serum (FCS) containing medium or 0.1 µg/ml of recombinant human PDGF-BB (R&D Systems). 50/50/0.1% BSA was used as a negative control. 4T-1 and A673 cells were harvested and resuspended in 50/50/0.1% BSA ($2\times10^5$ cells/ml). The following cell preparations were tested, where mANGPTL4 is indicated as NL2.

| 4T-1 | | A673 | |
|---|---|---|---|
| 50/50/0.1% BSA | NL2 6 µg | 50/50/0.1% BSA | NL2 6 µg |
| +10% FBS | NL2 1.5 µg | +10% FBS | NL2 1.5 µg |
| +10% FBS | NL2 0.375 µg | +10% FBS | NL2 0.375 µg |
| 50/50/0.1% BSA | PDGF-BB 0.1 µg | 50/50/0.1% BSA | NL2 0.375 µg |

The preparations were added to the bottom chamber in 750 µl and the preparations were incubated at 37° C. for 19 hours.

The cell suspension (250 µl) ($5\times10^4$) was added to the upper chamber and the cells were allowed to migrate for 7 hours at 37° C. in a 5% CO, humidified incubator. After incubation, medium was aspirated from the both top and bottom chambers, and cells that had migrated to the lower surface of the membrane were fixed with methanol (400 µl of MeOH for 30 minutes at 4° C., remove MeOH and air dry for 40 minutes) and stained with YO-PRO-1 iodide (Molecular Probes, OR) (400 µl YO-PRO-1 iodide at 10 µm (1:100 from 1 mM stock)). Migration results are quantitated in terms of the average number of cells/microscopic field at a 20-fold magnification using the Open/ab software (Improvision, Mass.). See, FIG. 9, where (1) is no serum added, (2) is 10% fetal calf serum (FCS), (3) is PDGF-BB, and (4) is ANGPTL4. Using both ANGPTL4 and 10% FCS, A673 and 4T-1 cells migrated. Hence, antagonists to Angptl4 can be used to inhibit metastasis, e.g., without being bound to one theory, by preventing migration of the tumor cells.

ANGPTL4 Increases Tumor Size In Vivo:

Human A673 rhabdomyosarcoma cells (HTB 1598) were cultured as described previously (Kim et al., *Nature* 362:841-844 (1993); and, Gerber et al., *Cancer Research*, 60:6253-6258 (2000)). Five$\times10^6$ A673 cells in 0.1 ml of Matrigel were injected s.c. in the dorsal flank region of beige nude mice (Harlan Sprague Dawley) to establish xenografts. An Adenovirus construct was injected $1\times10^8$ plaque forming units (PFU), intratumoral (IT), q7d at day 1, 7 and 14. Injections were made directly into the tumor mass, from the side and underneath, using a 28-gauge needle and a 0.5 ml tuberculin syringe. The adenovirus constructs were either an adenovirus-ANGPTL4 construct (Ad-Angptl4), an adenovirus-LacZ construct (Ad-LacZ) as a control or an adenovirus-ANGPTL3 construct (Ad-Angptl3). Tumor size was determined at various days post tumor implantation. Tumor size measurements were performed every second day and tumor volume was calculated using the ellipsoid volume formulas (n/6×L× W×H, where L=length, W=width, and H=height; Tomayko & Reynolds, *Cancer Chemother. Pharmacol.*, 24:148-154 (1989)). As seen in FIG. 8, tumor size (Panel A) and weight (Panel B) statistically increased (P<0.0001) in mice injected A673 cells and an adenovirus-ANGPTL4 construct (Ad-Angptl4) compared to the Ad-LacZ or Ad-Angptl3 constructs.

Example 2

Trend to Escape from Anti-VEGF Treatment of Tumors Treated with ANGPTL4

ANGPTL4 stimulated tumor cell proliferation in tumors being treated with an anti-angiogenesis agent, e.g., anti-VEGF (such as AVASTIN® (Genentech, South San Francisco). See FIG. 8, Panel C. Human A673 rhabdomyosarcoma cells (HTB 1598) were cultured as described previously (Kim et al., *Nature* 362:841-844 (1993); and, Gerber et al., *Cancer Research*, 60:6253-6258 (2000)). Five$\times10^6$ A673 cells in 0.1 ml of Matrigel were injected s.c. in the dorsal flank region of beige nude mice (Harlan Sprague Dawley) to establish xenografts. An Adenovirus construct was injected $1\times10^8$ plaque forming units (PFU), intratumoral (IT), q7d at day 1, 7, 14, 21, and 28. The adenovirus constructs were either an adenovirus-ANGPTL4 construct (Ad-Angptl4), an adenovirus-LacZ construct (Ad-LacZ) as a control or an adenovirus-ANGPTL3 construct (Ad-Angptl3). The mice were also treated with Avastin® (Genentech) at a dose of 5 mg/kg, ip, twice weekly. Injections were made directly into the tumor mass, from the side and underneath, using a 28-gauge needle and a 0.5 ml tuberculin syringe. Tumor size measurements were performed every second day and tumor volume was calculated using the ellipsoid volume formulas ($\pi/6\times L\times W\times H$, where L=length, W=width, and H=height; Tomayko & Reynolds, *Cancer Chemother. Pharmacol.*, 24:148-154 (1989)). As seen in FIG. 8, Panel C, tumor size increased in mice injected with an adenovirus-ANGPTL4 construct (Ad-Angptl4) although they were being treated with AVASTIN®, compared to mice injected with cells containing a Ad-LacZ or Ad-Angptl3 construct, in combination with AVASTIN® treatment.

Example 3

Antibodies that Bind to ANGPTL4 Inhibit Tumor Cell Growth

The ability of anti-ANGPTL4 antibodies to inhibit a biological activity of ANGPTL4, e.g., proliferation of tumor cells, was tested. $1\times10^4$ tumor cells (e.g., HeLa-S3, Caki, U87MG, 293, A673, HM7 and Calu 6)/well were plated on 12 well plates in media with 10% FCS. The cells were allowed to incubate overnight at 37° C. in a 5% CO$_2$ humidified incubator. Media was changed to 5% FCS (except for Calu 6 cells which were in 10% FCS) and 1, 2.5, 5, or 10 µg/ml of anti-hANGPTL4 antibody or anti-Dscr or no antibody was added to the wells. Plates were placed at 37° C. in a 5% CO$_2$ humidified incubator. Cells were counted at day 2 or 3 following addition of anti-hANGPTL4 antibody. Anti-ANGPTL4 antibody inhibited cell growth of HeLa-S3, Caki U87MG, 293, A673, and Calu 6, but not HM7 cells. See, FIG. 10, Panel A and B.

Example 4

Preparation of Antibodies that Bind to ANGPTL4

Techniques for producing the polyclonal antibodies and monoclonal antibodies are known in the art and are described herein. Antigens (or immunogens) that may be employed include purified protein of the invention, protein fragments, fusion proteins containing such protein, and cells expressing recombinant protein and/or protein fragments on the cell surface. Selection of the antigen can be made by the skilled artisan without undue experimentation.

Mice, such as Balb/c, are immunized with the antigen emulsified in complete Freund's adjuvant and injected subcutaneously or intraperitoneally in an amount from 1-100 micrograms. Alternatively, the antigen is emulsified in MPL-TDM adjuvant (Ribi Immunochemical Research, Hamilton, Mont.) and injected into the animal's hind food pads. The immunized mice are then boosted 10 to 12 days later with additional antigen emulsified in the selected adjuvant. Thereafter, for several weeks, the mice might also be boosted with additional immunization injections. Serum samples may be periodically obtained from the mice by retro-orbital bleeding for testing ELISA assays to detect the antibodies.

After a suitable antibody titer has been detected, the animals "positive" for antibodies can be injected with a final intravenous injection of the given ligand. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against the antigen. Determination of "positive" hybridoma cells secreting the desired monoclonal antibodies against ANGPTL4 herein is well within the skill in the art.

The positive hybridoma cells can be injected intraperitoneal into syngeneic Balb/c mice to produce ascites containing the anti-ANGPTL4 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

For example, polyclonal rabbit antibodys were generated by immunization of rabbit with 500 µg of recombinant human ANGPTL4 protein (23-406) generated in *E. Coli* on days 1, 40 and 70. Serum was harvested in day 80 and 120 post immunization and antibodies were purified by protein-A sephadex columns.

Example 5

Blocking or Neutralizing Antibodies

Antibodies against the antigens described herein can be identified by a variety of techniques known in the art, e.g., an ELISA. For example, plates can be coated with the polypeptide of interest, e.g., ANGPTL4 or a fragment thereof, and incubated with antibodies generated against that polypeptide, e.g., ANGPTL4 (see, e.g., description in U.S. Pat. Nos. 6,348, 350, 6,372,491 and 6,455,496). Bound antibody can be detected by various methods.

Antagonist (e.g., blocking or neutralizing) antibodies can be identified by competition assays and/or activity assays. For example, expression of ANGPTL4 stimulates tumor cell proliferation, migration, adhesion or binding to $\alpha_v\beta_5$. Determination of a blocking or neutralizing antibody to ANGPTL4 can be shown by the ability of the antibody to block the tumor cell proliferation (see, e.g., FIG. 10, Panel A and B), migration, adhesion (see, e.g., FIG. 12) or binding to $\alpha_v\beta_5$ (USBiological, 37K, Swampscott, Mass.) (see, e.g., FIG. 13, Panel B and C). For example, A673 rhabdomyosarcoma cells can be plated and incubated with supernatant from COS7 cells transduced with Ad-hAngptl4 along with an anti-ANGPTL4 antibody, or a control antibody or PBS. After several days, the cells can be trypsinized and counted. Antibodies that reduce the numbers of cells are identified as blocking or neutralizing antibodies. ANGPTL4 was also shown to induce cell migration of tumor cells and to be a pro-angiogenic factor. See, e.g., Le Jan et al., *American Journal of Pathology*, 164(5): 1521-1528 (2003). Thus, blocking or neutralizing antibodies to ANGPTL4 can be identified by using the antibodies in combination with ANGPTL4 in tumor cell migration assays, and/or angiogenesis assays, e.g., CAM assay.

Blocking or neutralizing antibodies against ANGPTL4 which can be used in the block or reduce tumor growth or block or reduce cancer cell growth can also be identified by using tumor cells in culture as described above and/or in Beige/nude mice studies. For example, nude mice can be injected with tumor cells. At various times after tumor growth is established, the mice can be injected intraperitoneally once or twice a week with various doses of the blocking or neutralizing ANGPTL4 antibody, an antibody control, or PBS. Tumor size can be measured every week, and at the conclusion of the study the tumor can be excised and weighed. Blocking or neutralizing ANGPTL4 antibodies are identified which block or reduce tumor growth in the mice.

Combinations of ANGPTL4 antibodies and anti-angiogenesis agent to block or reduce tumor growth or block or reduce cancer cell growth can be can be identified by using tumor cells in culture as described above and/or Beige/nude mice studies. As indicated above, nude mice can be injected with tumor cells. At various times after tumor growth is established, the mice can be injected intraperitoneally once or twice a week with various doses of the combination of an ANGPTL4 antagonist and an anti-cancer agent, e.g., anti-angiogenesis agent, such as anti-VEGF antibody, or an ANGPTL4 antagonist, or an anti-cancer agent, or an antibody control, or PBS. Tumor size can be measured every week, and at the conclusion of the study the tumor can be excised and weighed. Combination therapies of ANGPTL4 antagonists and anti-cancer agents are identified which block or reduce tumor growth in the mice, or which enhance to block or reduce tumor growth in comparison to a control or by a single agent alone.

Example 6

ANGPTL4 Variant

A variant ANGPTL4 was made using a standard mutagenesis kit (e.g., QuikChange XL Site-Directed Mutagenesis Kit (Invitrogen, Carlsbad, Calif.)) following the manufacturer's protocol. Two amino acid substitutions were made in the human ANGPTL4 sequence (see, e.g., FIG. 2). The substitutions were at position 162 and 164 (R162G and R164E), resulting in a RKR to GKE change. ANGPTL4 protein (L280 plasmid, aa 1-406) or variant ANGPTL4 was isolated from the supernatant of transiently transfected COS-7 cells. For purification, the supernatant was loaded on a nickel column. Protein was detected by Western blot with an anti-FLAG-HRP antibody. See, FIG. 3, Panel B. When the substitutions were made and the variant ANGPTL4 was compared to native or wild type ANGPTL4 protein, the variant ANGPTL4 was found to have a higher molecular weight than native ANGPTL4 by Western blotting. The substitution from RKR to GKE at position 162 and 164 of the native protein prevented proteolytic degradation of ANGPTL4.

Example 7

ANGPTL4 Binds $\alpha_v\beta_5$ Integrin

Angiopoietins are secreted factors that regulate angiogenesis by binding to the endothelial cell specific tyrosine kinase receptor Tie2 via their fibrinogen (FBN)-like domain. The coiled-coil domain present in the family of secreted ligands was found to be necessary for ligant oligomerization (see, e.g., Procopio et al., *J. Biol. Chem.*, 274:30196-201 (1999)).

Similar to the angiopoietins, ANGPTL3 and ANGPTL4 are secreted glycoproteins, each consisting of an N-terminal signal peptide, followed by a coiled-coil domain and a C-terminal FBN-like domain. It was determined that ANGPTL3 binds to $\alpha_v\beta_3$ through the FBN-like domain. We determined that ANGPTL4 binds to $\alpha_v\beta_5$. 293-1953 cell line that is stably transfected with $\alpha_v\beta_5$ integrin was tested for the ability to bind or adhere to ANGPTL4 coated plates. Cells were harvested and diluted to $10^5$ cells/ml in serum-free medium containing, PBS, 1% BSA, 1 mM $CaCl_2$ and 1 mM $MgCl_2$. Cells were preincubated with or without anti-integrin $\alpha_v\beta_5$ antibodies (MAB 1961 (Chemicon, Temecula, Calif.)) or peptides for 15 minutes at 37° C. Recombinant mANGPTL4, BSA or vitronectin (1 µg, 3 µg, 10 µg, or 30 µg/ml) were coated on to Nunc Maxisorp 96-well flat-bottomed microtiter plates overnight at 4° C. and blocked with 200 µl of 3% BSA in phosphate buffer saline (PBS), pH 7.4, for 1.5 hours at 37° C. Cell suspensions ($5\times10^4$ cells/100 µl/well ($5\times10^5$/ml)) were added to the coated wells and the plates were incubated at 37° C. for 5.5 hours. Non-adherent cells were removed by PBS washes and cell attachment was measured by adding 200 µl of CyQuant GD Dye (Molecular Probes (Invitrogen detection Technologies (Carlsbad, Calif.)) (1:400)/cell lysis buffer and incubated for 2-5 minutes. The sample fluorescence was measured using 480 nm excitation and 520 nm emission maxima. The PNAG method of Lanndegren can also be used (see, e.g., Landegren, J. Immunol. Methods, 67:379-388 (1984)). Cells expressing $\alpha_v\beta_5$ displayed adherence to ANGPTL4 and vitronectin (USBiological, Swampscott, Mass.), a positive control, compared to BSA, a negative control. See FIG. 11.

To determine whether the $\alpha_v\beta_5$ integrin was sufficient to mediate ANGPTL4 cell adhesion, blocking antibodies were tested for their ability to inhibit the adhesion in the cell adhesion assay. Functional blocking antibodies (anti-$\alpha_v\beta_5$ antibody (MAB 1961 (Chemicon, Temecula, Calif.)) or anti-hANGPTL4 antibodies) were added to 293-1953 cells prior to incubation with the protein coated (BSA (1), vitronectrin (2) or ANGPTL4(3)) wells. See FIG. 12. Anti-$\alpha_v\beta_5$ and anti-ANGPTL4 antibodies abolished ANGPTL4 cell adhesion activity.

Additional experiments were performed to confirm that ANGPTL4 binds $\alpha_v\beta_5$. ELISA experiments were performed to detect if mANGPTL4, IgG-hANGPTL4-Nterminal (1-183) and/or IgG-hANGPTL4-Cterminal (184-406) binds to $\alpha_v\beta_5$ (USBiological, 37K, Swampscott, Mass.) coated plates. 100 µl/well of integrin $\alpha_v\beta_5$ diluent (1 µg/ml coating buffer (50 mM carbonate/bicarbonate, pH 9.6)) with coating buffer was incubated overnight at 4° C. The plates were washed three times with wash buffer (PBS, pH 7.4, 0.05% Tween-20), and 100 µl/well of blocking buffer (PBS, pH 7.4, 0.5% BSA) was added for 1 hour at room temperature with gentle agitation. Various amounts (0, 0.070 µg, 0.22 µg, 0.66 µg, 2 µg, or 6 µg) of samples, mANGPTL4, IgG-hANGPTL4-Nterminal (1-183) and/or IgG-hANGPTL4-Cterminal (184-406), were prepared in sample buffer (0.5% BSA, 50 mM Tris, pH 7.4, 0.05% Tween 20, 1 mM $MnCl_2$, 50 µM $CaCl_2$, 50 µM $MgCl_2$, 100 mM NaCl) and incubated for 30 minutes. Samples were added to plates (100 µl/well in the amounts incubated above) and incubated for 2 hours at room temperature with gentle agitation. Plates were washed with buffer and 100 µl/well anti-Flag-horseradish peroxidase (HRP) (100 ng/ml) (Jackson, #109-036-098) in assay buffer (PBS, pH7.4, 0.5% BSA, 0.05% Tween 20) was added and incubated for 1 hour at room temperature with gentle agitation. The plates were washed. 100 µl/well of tetramethylbenzidine (TMB) (Moss, Inc.) was added and incubated in the plates until good color was developed at room temperature. 100 µl/well Stop solution (1 M $H_3PO_4$) was added to stop the reaction. The plates were read at 630 nm. mANGPTL4, IgG-hANGPTL4-Nterminal and IgG-hANGPTL4-C-terminal bound to $\alpha_v\beta_5$ coated plates, although slightly more of IgG-hANGPTL4-Cterminal bound to the plates. See, FIG. 13, Panel A.

Anti-ANGPTL4 antibodies inhibit binding of ANGPTL4 to $\alpha_v\beta_5$ coated plates. ELISA experiments were performed. 100 µl/well of integrin $\alpha_v\beta_5$ diluent (1 µg/ml coating buffer (50 mM carbonate/bicarbonate, pH 9.6)) with coating buffer was incubated overnight at 4° C. The plates were washed three times with wash buffer (PBS, pH 7.4, 0.05% Tween-20), and 100 µl/well of blocking buffer (PBS, pH 7.4, 0.5% BSA) was added for 1 hour at room temperature with gentle agitation. 0.6 µg to 6.0 µg of samples, mANGPTL4, IgG-hANGPTL4-Nterminal (1-183) and/or IgG-hANGPTL4-Cterminal (183-406), in sample buffer (0.5% BSA, 50 mM Tris, pH 7.4, 0.05% Tween 20, 1 mM $MnCl_2$, 50 µM $CaCl_2$, 50 µM $MgCl_2$, 100 mM NaCl) were incubated with anti-ANGPTL4 antibodies (1.5 µg) or anti-Dscr (1.5 µg) for 30 minutes. After incubation, 100 µl/well of sample+/−antibody was incubated with the plates for 2 hours at room temperature with gentle agitation. Plates were washed with buffer and 100 µl/well anti-Flag-HRP (100 ng/ml) in assay buffer (PBS, pH7.4, 0.5% BSA, 0.05% Tween 20) was added and incubated for 1 hour at room temperature with gentle agitation. The plates were washed and 100 µl/well of TMB was added and incubated in the plates until good color was developed at room temperature. 100 µl/well Stop solution (1 M $H_3PO_4$) was added to stop the reaction. The plates were read at 630 nm. Anti-ANGPTL4 antibodies reduced the amount of mANGPTL4, IgG-hANGPTL4-Nterminal and IgG-hANGPTL4-Cterminal binding to the $\alpha_v\beta_5$ coated plates compared to anti-Dscr antibody, 5G7 monoclonal antibody or medium. See, FIG. 13, Panel B.

In another experiment, binding of ANGPTL4 and integrin $\alpha_v\beta_5$ was shown by ELISA. In this experiment, 80 µl/well of hANGPTL4-C terminal, vitronectin or BSA (5 µg/ml) was added to plates in coating buffer (50 mM carbonate/bicarbonate, pH 9.6) and incubated overnight at 4° C. The plates were washed (wash buffer: PBS, pH 7.4, 0.05% Tween-20) and 1000/well of blocking buffer (PBS, pH 7.4, 0.5% BSA) with either media, anti-hANGPTL4 antibodies (15 µg/100 µl), or anti-Dscr antibodies (15 µl/100 µg) was added and incubated for 1 hour at room temperature with gentle agitation. The plates were washed and $\alpha_v\beta_5$ 100 µl (3-9 µg/ml) was added and incubated for 2 hours at room temperature with gentle agitation. The plates were washed and 1 µg/ml (1:1000) of anti-$\alpha_v\beta_5$ antibody (Chemicon) (5 μg/100 μl) was added in assay buffer (PBS, pH7.4, 0.5% BSA, 0.05% Tween 20) and incubated for 1 hour at room temperature with gentle agitation. After incubation, the plates were washed and 100 μl/well horseradish peroxidase (HRP) anti-mouse (1:5000) was added in assay buffer. The plates were washed and 100 μl/well tetramethylbenzidine (TMB) was added and incubated at room temperature until there was good color development. The reaction was stopped with 100 μl/well 1 M $H_3PO_4$ and plates were read at 630 nm. $\alpha_v\beta_5$ binds to ANGPTL4 (lane 1) and vitronectin (lane 4) coated plates. The binding is blocked with an anti-ANGPTL4 antibodies (lane 2) but not when a control antibody anti-Dscr is used (lane 3) or a control protein is coated on the plates (lane 5). See, FIG. 13, Panel C.

Hence, these findings demonstrate that recombinant ANGPTL4 binds specifically to the $\alpha_v\beta_5$ integrin.

The specification is considered to be sufficient to enable one skilled in the art to practice the invention. It is understood that the examples and embodiments described herein are for illustrative purposes only. The invention is not to be limited in scope by the construct deposited, since the deposited embodiment is intended as a single illustration of certain aspects of the invention and any constructs that are functionally equivalent are within the scope of the invention. The deposit of material herein does not constitute an admission that the written description is inadequate to enable the practice of any aspect of the invention, including the best more thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

We claim:

1. A composition comprising an ANGPTL4-SiRNA molecule, wherein the ANGPTL4-SiRNA molecule targets GTGGCCAAGCCTGCCCGAAGA (SEQ ID NO:3) within a DNA sequence encoding ANGPTL4.

2. A pharmaceutical composition comprising an anti-angiogenesis agent and a pharmaceutically acceptable carrier, where the anti-angiogenesis agent is the ANGPTL-SiRNA molecule of claim 1.

3. The pharmaceutical composition of claim 2, wherein the carrier is a viral vector.

4. The pharmaceutical composition of claim 2, wherein the carrier is a liposome.

* * * * *